United States Patent
Noriega et al.

(10) Patent No.: US 10,857,222 B2
(45) Date of Patent: Dec. 8, 2020

(54) CONCOMITANT DENGUE AND YELLOW FEVER VACCINATION

(71) Applicant: SANOFI PASTEUR, Lyons (FR)

(72) Inventors: Fernando Noriega, Cresco, PA (US); Betzana Zambrano, Montevideo (UY); Nadia Tornieporth, Wedemark (DE); Mélanie Saville, Saint Didier au Mont D'or (FR); Eric Plennevaux, Marcy L'etoile (FR); Mark Boaz, New York, NY (US); Thomas Papa, Cheltenham (GB)

(73) Assignee: SANOFI PASTEUR, Lyons (FR)

( * ) Notice: Subject to any disclaimer, the term of this patent is extended or adjusted under 35 U.S.C. 154(b) by 0 days.

(21) Appl. No.: 15/740,889

(22) PCT Filed: Jul. 1, 2016

(86) PCT No.: PCT/EP2016/065580
§ 371 (c)(1),
(2) Date: Dec. 29, 2017

(87) PCT Pub. No.: WO2017/005652
PCT Pub. Date: Jan. 12, 2017

(65) Prior Publication Data
US 2018/0193447 A1 Jul. 12, 2018

(30) Foreign Application Priority Data
Jul. 3, 2015 (EP) ..................................... 15306101

(51) Int. Cl.
| A61K 39/12 | (2006.01) |
| A61K 39/295 | (2006.01) |
| C07K 14/18 | (2006.01) |
| A61K 39/00 | (2006.01) |

(52) U.S. Cl.
CPC ............ *A61K 39/12* (2013.01); *A61K 39/295* (2013.01); *C07K 14/1825* (2013.01); *A61K 2039/522* (2013.01); *A61K 2039/5254* (2013.01); *A61K 2039/545* (2013.01); *A61K 2039/70* (2013.01); *C12N 2770/24134* (2013.01); *C12N 2770/24141* (2013.01); *C12N 2770/24171* (2013.01); *Y02A 50/30* (2018.01)

(58) Field of Classification Search
None
See application file for complete search history.

(56) References Cited

U.S. PATENT DOCUMENTS

| 6,696,281 B1 | 2/2004 | Chambers et al. |
| 6,962,708 B1 | 11/2005 | Chambers et al. |
| 7,459,160 B2 | 12/2008 | Monath et al. |
| 7,641,907 B2 | 1/2010 | Kinney et al. |
| 7,641,908 B2 | 1/2010 | Kinney et al. |
| 7,718,357 B2 | 5/2010 | Barban et al. |
| 7,718,358 B2 | 5/2010 | Guy et al. |
| 7,718,359 B2 | 5/2010 | Guy et al. |
| 7,968,102 B2 | 6/2011 | Quentin-Millet |
| 8,067,565 B2 | 11/2011 | Kinney et al. |
| 8,067,566 B2 | 11/2011 | Kinney et al. |
| 8,142,795 B2 | 3/2012 | Francon et al. |
| 8,227,587 B2 | 7/2012 | Quentin-Millet |
| 8,697,353 B2 | 4/2014 | Bouckenooghe et al. |
| 8,795,688 B2 | 8/2014 | Kinney et al. |
| 8,852,914 B2 | 10/2014 | Monath et al. |
| 9,169,298 B2 | 10/2015 | Kinney et al. |
| 2004/0259224 A1 | 12/2004 | Guirakhoo |
| 2005/0002968 A1 | 1/2005 | Monath et al. |
| 2006/0062803 A1 | 3/2006 | Kinney et al. |
| 2006/0292172 A1 | 12/2006 | Kinney et al. |
| 2008/0014219 A1 | 1/2008 | Barban et al. |
| 2008/0085288 A1 | 4/2008 | Guy et al. |
| 2008/0131460 A1 | 6/2008 | Guy et al. |
| 2009/0169581 A1 | 7/2009 | Sandrine |

(Continued)

FOREIGN PATENT DOCUMENTS

| EP | 1958959 | 8/2008 |
| WO | WO1998/037911 | 9/1998 |

(Continued)

OTHER PUBLICATIONS

ClinicalTrials.gov. Study of Yellow Fever Vaccine Administered With Tetravalent Dengue Vaccine in Healthy Toddlers. ClinicalTrials.gov Identifier: NCT01436396. Sponsor: Sanofi Pasteur. First Posted: Sep. 9, 2011; Last updated Apr. 2, 2014.*
Halstead SB. Vaccine. Nov. 7, 2017;35(47):6355-6358. Epub Oct. 10, 2017.*
Flasche S, et. al. PLoS Med. Nov. 29, 2016;13(11):e1002181. eCollection Nov. 2016.*
Konishi E. Trop Med Health. Dec. 2011;39(4 Suppl):63-71. Epub Aug. 6, 2011.*
Monath TP. Dengue and yellow fever—challenges for the development and use of vaccines. N Engl J Med. Nov. 29, 2007;357(22): 2222-5.*

(Continued)

*Primary Examiner* — Benjamin P Blumel
(74) *Attorney, Agent, or Firm* — McDonnell Boehnen Hulbert & Berghoff LLP

(57) ABSTRACT

The present invention relates to a yellow fever (YF) vaccine for use in a method for inducing a protective immune response against yellow fever, wherein said method comprises concomitantly administering said yellow fever vaccine to a human subject together with a tetravalent dengue vaccine which comprises a live attenuated dengue virus of each of serotypes 1 to 4. This invention also pertains to a tetravalent dengue vaccine which comprises a live attenuated dengue virus of each of serotypes 1 to 4 for use in a method of inducing a protective immune response against yellow fever, wherein said method comprises concomitantly administering said tetravalent dengue vaccine to a human subject together with a yellow fever (YF) vaccine.

24 Claims, 4 Drawing Sheets
Specification includes a Sequence Listing.

(56) References Cited

U.S. PATENT DOCUMENTS

| | | |
|---|---|---|
| 2009/0191240 A1 | 7/2009 | Monath et al. |
| 2010/0015180 A1 | 1/2010 | Francon et al. |
| 2010/0158938 A1 | 6/2010 | Guirakhoo |
| 2010/0215692 A1 | 8/2010 | Quentin-Millet |
| 2010/0221285 A1 | 9/2010 | Barban et al. |
| 2010/0239612 A1 | 9/2010 | Guy et al. |
| 2010/0255028 A1 | 10/2010 | Delagrave et al. |
| 2010/0270202 A1 | 10/2010 | Guy et al. |
| 2011/0014229 A1 | 1/2011 | Kleanthous et al. |
| 2011/0150771 A1 | 6/2011 | Kinney et al. |
| 2011/0189226 A1 | 8/2011 | Bouckenooghe et al. |
| 2011/0206730 A1 | 8/2011 | Quentin-Millet |
| 2012/0083584 A1 | 4/2012 | Kinney et al. |
| 2012/0083585 A1 | 4/2012 | Kinney et al. |
| 2013/0028934 A1 | 1/2013 | Francon et al. |
| 2013/0095136 A1 | 4/2013 | Guirakhoo |
| 2013/0149338 A1 | 6/2013 | Stinchcomb et al. |
| 2014/0220073 A1 | 8/2014 | Bouckenooghe et al. |
| 2015/0024004 A1 | 1/2015 | Monath et al. |
| 2015/0031857 A1 | 1/2015 | Kinney et al. |
| 2015/0196631 A1 | 7/2015 | Bouckenooghe et al. |
| 2015/0265695 A1 | 9/2015 | Yao et al. |

FOREIGN PATENT DOCUMENTS

| | | | |
|---|---|---|---|
| WO | WO2001039802 | 6/2001 | |
| WO | WO2002081754 | 10/2002 | |
| WO | WO2008047023 | 4/2008 | |
| WO | WO2011/013097 | 2/2011 | |
| WO | WO2011/146933 | 11/2011 | |
| WO | WO2012/051491 | 4/2012 | |
| WO | WO2014/016360 | 1/2014 | |
| WO | WO2014/016362 | 1/2014 | |
| WO | WO-2014016360 A1 * | 1/2014 | ............. A61K 39/12 |
| WO | WO2017/005654 | 1/2017 | |

OTHER PUBLICATIONS

Anderson et al., "Interference and Facilitation Between Dengue Serotypes in a Tetravalent Live Dengue Virus Vaccine Candidate," Journal of Infectious Diseases, vol. 204, No. 3, (Aug. 1, 2011) pp. 442-450.

Capeding et al., "Clinical efficacy and safety of a novel tetravalent dengue vaccine in healthy children in Asia: a phase 3, randomised, observer-masked, placebo-controlled trial," www.thelancet.com, vol. 384, Oct. 11, 2014, pp. 1358-1365.

Guirakhoo et al., "Safety and Efficacy of Chimeric Yellow Fever-Dengue Virus Tetravalent Vaccine Formulations in Nonhuman Primates," Journal of Virology, vol. 78, No. 9, May 2004, p. 4761-4775.

Sanofi Pasteur, a Sanofi Company, "Immune Response to Different Schedules of a Tetravalent Dengue Vaccine Given With or Without Yellow Fever Vaccine," ClinicalTrials.gov, a service of he U.S. National Institutes of Health, identifier NCT01488890, 4 pages.

Qiao et al., "Priming Effect of Dengue and Yellow Fever Vaccination on the Immunogenicity, Infectivity, and Safety of a Tetravalent Dengue Vaccine in Humans," Am. J. Trop. Med. Hyg., 85(4), 2011, pp. 724-731.

Da Costa et al., "Safety, immunogenicity and efficacy of a recombinant tetravalent dengue vaccine: A meta-analysis of randomized trials," Vaccine 32 (2014) 4885-4892.

Dayan et al., "Immunogenicity and Safety of a Recombinant Tetravalent Dengue Vaccine in Children and Adolescents Ages 9-16 Years in Brazil," Am. J. Trop. Med. Hyg., 89(6), 2013, pp. 1058-1065.

Dobbelaer, CHMP Vaccine Working Party, VWP Conclusions from the Workshop on Co-administration of Vaccines held on Jan. 31-Feb. 1, 2006, European Medicines Agency, London, Jan. 16, 2007, 4 pages.

Fletcher et al., "Vaccines administered simultaneously: directions for new combination vaccines based on an historical review of the literature," International Journal of Infectious Diseases (2004) 8, 328-338.

Querec et al., "Yellow fever vaccine YF-17D activates multiple dendritic cell subsets via TLR2, 7, 8, and 9 to stimulate polyvalent immunity," JEM, The Rockefeller University Press, vol. 203, No. 3, Feb. 20, 2006, pp. 413-424.

Guy et al., "From research to phase III: Preclinical, inudstrial and clinical development of the Sanofi Pasteur tetravalent dengue vaccine," Vaccine, 29 (2011) 7229-7241.

Felsenfeld et al., "Simultaneous Vaccination Against Cholera and Yellow Fever," The Lancet, Mar. 3, 1973, pp. 457-458.

Fisker et al., "Co-administration of live measles and yellow fever vaccines and inactivated pentavelent vaccines is associated with increased mortality compared with measles and yellow fever vaccines only. An observational study from Guinea-Bissau," Vaccine 32 (2014) 598-605.

Gubler, "Epidemic dengue/dengu hemorrhagic fever as a public health, social and economic problem in the 21st century," TRENDS in Microbiology, vol. 10, No. 2, Feb. 2002, pp. 100-103.

Kautner et al., "Dengue virus infection: Epidemiology, pathogenesis, clinical presentation, diagnosis, and prevention," The Journal of Pediatrics, vol. 131, No. 4, pp. 516-524.

Markoff, "In Vitro Processing of Dengue Virus Structural Proteins: Cleavage of the Pre-Membrane Protein," Journal of Virology, vol. 63, No. 8, Aug. 1989, pp. 3345-3352.

Meyer, Jr. et al., "Response of Volta Children to Jet Inoculation of Combined Live Measles, Smallpox and Yellow Fever Vaccines," Bull. Org. mond. Sante, Bulol. Wld Hlth Org., 1964, 30, 783-794.

Monath, "Dengue: The risk to developed and developing countries," Mar. 1994, Proc. Natl. Acad. Sci. USA, vol. 91, pp. 2395-2400.

Rigau-Perez et al., "Dengue and dengue haemorrhagic fever," The Lancet, Vo. 352, Sep. 19, 1998, pp. 971-977.

Schmitz et al., "Next generation dengue vaccines: A review of candidates in preclinical development," Vaccine, 29 (2011) pp. 7276-7284.

Silva et al., "Mutual interference on the immune response to yellow fever vaccine and a combined vaccine against measles, mumps and rubella," Vaccine, 29, (2011) pp. 6327-6334.

Vazquez et al., "Immune response to synthetic peptides of dengue prM protein," Vaccine, 20, (2002) pp. 1823-1830.

Vaughn et al., "Dengue in the Early Febrile Phase: Viremia and Antibody Responses," Oxford Journals, The Journal of Infectious Diseases, vol. 176, No. 2 (Aug. 1997) pp. 322-330.

Villar et al., "Efficacy of a Tetravalent Dengue Vaccine in Children in Latin America," The New England Journal of Medicine, vol. 372, No. 2, Jan. 8, 2015, pp. 113-123.

"SAGE Working Group on Yellow Fever Vaccine: Interference between YF vaccine and other vaccines" Jan. 11, 2012 (available at http://www.who.int/immunization/sage/meetings/2013/april/5_Concomitant_administration_interference_yellow_fever_vaccine_other_vaccines.pdf?ua=1, last accessed May 1, 2018).

Sridhar et al., "Effect of Dengue Serostatus on Dengue Vaccine Safety and Efficacy," New England Journal of Medicine, published Jun. 13, 2019 at NEJM.org.

Villar et al., "Efficacy of a Tetravalent Dengue Vaccine in Children in Latin America," New England Journa of Medicine, published Nov. 3, 2014, at NEJM.org.

Kirstein, Judith et al. "Immunogenicity of the CYD tetravalent dengue vaccine using an accelerated schedule: randomised phase II study in US adults" BMC Infection Diseases (2018) vol. 18(475) 11 pages.

Lopez, Pio et al. "Immunogenicity and safety of Yellow Fever Vaccine (Stamaril) when administered concomitantly with a tetravalent dengue vaccine candidate in health toddlers at 12-13 month of age in Colombia and Peru" The Jediahic Infectious Disease Journal (2016) vol. 35(10), pp. 1140-1147.

Study Results as published on clinicaltrials.gov in respect of the trial with reference NCT01488890; Online, URL https://clinicaltrials.gov/ct2/show/results/NCT01488890 accessed Nov. 4, 2019, 37 pages.

Study Details as published on clinicaltrials.gov in respect of the trial with reference NCT01436396; Online, URL https://clinicaltrials.gov/ct2/show/NCT01436396 accessed Nov. 4, 2019, 14 pages.

(56) References Cited

OTHER PUBLICATIONS

Study Results as published on clinicaltrials.gov in respect of the trial with reference NCT01436396; Online, URL https://clinicaltrials.gov/ct2/show/results/NCT01436396 accessed Nov. 4, 2019, 43 pages.
Gilbert, Peter B. et al. "Bridging Efficacy of a Tetravalent Dengue Vaccine from Children/Adolescents to Adults in Highly Endemic Countries Based on Neutralizing Antibody Response" American Journal of Tropical Medicine and Hygiene (2019) vol. 101(1), pp. 164-179.
Coronel, Diana et al., Abstract submitted to the Annual Meeting of the American Society of Tropical Medicine and Hygiene 2019 (ASTMH), 2 pages.
Dayan, Gustavo et al., Poster submitted to National Foundation for Infectious Diseases (NFID), 22nd Annual Conference on Vaccinology Research 2019.
Dayan, Gustavo et al., Abstract submitted to the Annual Meeting of the American Society of Tropical Medicine and Hygiene 2019 (ASTMH).
Rabaa et al., "Genetic epidemiology of dengue viruses in phase III trials for the CYD tetravalent dengue vaccine and implications for efficacy." eLife 6:e24196 https://doi.org/10.7554/eLife.24196.001.
World Health Organization (WHO), "Guidelines on the Quality, Safety and Efficacy of Dengue Tetravalent Vaccines (Live, Attenuated)," Proposed replacement of TRS 932, Annex 1. WHO Press, Geneva, Switzerland, May 1, 2011 https://www.who.int/biologicals/areas/vaccines/dengue/WHO_DRAFT_Den_24May2011.pdf.
Guy et al, "Development of sanofi pasteur tetravalent dengue vaccine", Human Vaccines, 6:9, 696-705.
Poo et al, "Live-attenuated Tetravalent Dengue Vaccine in Dengue-naive Children, Adolescents, and Adults in Mexico City—Randomized Controlled Phase 1 Trial of Safety and Immunogenicity", The Pediatric Infectious Disease Journal, vol. 30, No. 1, Jan. 2011, pp. 1-9.
Lanata et al, "Immunogenicity and safety of tetravalent dengue vaccine in 2-11 year-olds previously vaccinated against yellow fever Randomized, controlled, phase II study in Piura,I Peru", Vaccine 30 (2012) 5935-5941.
Guy et al, "A recombinant live attenuated tetravalent vaccine for the prevention of dengue", Expert Review of Vaccines, 2017, vol. 16, No. 7, 671-683.
Sabchareon et al, "Protective efficacy of the recombinant, live-attenuated, CYD tetravalent dengue vaccine in Thai schoolchildren: a randomised, controlled phase 2b trial", Lancet, 2012, 380:1559-67.
World Health Organization, Immunization, Vaccines and Biologicals: Questions and Answers on Dengue Vaccines http://www.who.int/immunization/research/development/dengue_q_and_a/en/.
Blaney et al., "Recombinant, Live-Attenuated Tetravalent Dengue Virus Vaccine Formulations Induce a Balanced, Broad, and Protective Neutralizing Antibody Response against Each of the Four Serotypes in Rhesus Monkeys"; Journal of Virology, (2005), vol. 79(9), p. 5516-5528; https://doi.org/10.1128/JVI.79.9.5516-5528.2005 (published May 2005).
Park et al, Immunogenicity and safety of a dengue vaccine given as a booster in Singapore: a randomized Phase II, placebo-controlled trial evaluating its effects 5-6 years after completion of the primary series; Human Vaccines & Immunotherapeutics; 2020, vol. 16, No. 3, 523-529; https://doi.org/10.1080/21645515.2019.1661204 (published Nov. 5, 2019).
Limkittikul et al, Long-term safety follow-up of children from a randomized controlled phase llb proof of concept efficacy study of the live attenuated tetravalent dengue vaccine (CYD-TDV) in Thailand; Asian Pacific Journal of Tropical Medicine 2019; vol. 12(9); p. 396-403; https://doi.org/10.4103/1995-7645.267582 (published Sep. 30, 2019).
Reynales et al, Secondary Analysis of the Efficacy and Safety Trial Data of the Tetravalent Dengue Vaccine in children and Adolescents in Colombia; The Pediatric Infectious Disease Journal (2020), vol. 39(4), p. e30-e36; https://doi.org/10.1097/INF.0000000000002580 (published Apr. 2020).
Carpp et al, Microneutralization assay titer correlates analysis in two Phase 3 trials of the CYD-TDV tetravalent dengue vaccine in Asia and Latin America; PLoS ONE (2020), vol. 15(6); https://doi.org/10.1371/journal.pone.0234236 (published Jun. 15, 2020).
Durbin et al., "A Single Dose of Any of Four Different Live Attenuated Tetravalent Dengue Vaccines is Safe and Immunogenic in Flavivirus-Naive Adults: A Randomized, Double-Blind Clinical Trial," J Infect Dis., 207(6): 957-965 Mar. 15, 2013). https://doi.org/10.1093/infdis/jis936 (published Jan. 17, 2013).
Durbin et al., "Next-generation dengue vaccines: novel strategies currently under development", -Viruses, 3(10), pp. 1800-1814 (E-pub Sep. 26, 2011). https://doi.org/10.3390/v3101800 (published Sep. 26, 2011).
George, S.L., "Prospects for a Dengue Vaccine: Progress and Pitfalls," Missouri Medicine, 111(4): 337-342 (Jul./Aug. 2014). https://pubmed.ncbi.nlm.nih.gov/25211865/ (published Jul.-Aug. 2014).
Gilbert, Peter B. et al. "Bridging Efficacy of a Tetravalent Dengue Vaccine from Children/Adolescents to Adults in Highly Endemic Countries Based on Neutralizing Antibody Response" American Journal of Tropical Medicine and Hygiene (2019) vol. 101(1), pp. 164-179. https://doi.org/10.4269/ajtmh.18-0534 (published May 20, 2019).
Guy et al, "Cell-mediated immunity induced by chimeric tetravalent dengue vaccine in naive or flavivirus-primed subjects," Vaccine. 26(45):5712-21 (2008). https://doi.org/10.1016/j.vaccine.2008.08.019.
Houlton, "Sanofi Ordered to Pull Dengue Vaccine" Chemistry World, 3 pages, Dec. 15, 2017. https://www.chemistryworld.com/news/sanoti-ordered-to-pull-dengue-vaccine/3008436.article.
Kirstein, Judith et al. "Immunogenicity of the CYD tetravalent dengue vaccine using an accelerated schedule: randomised phase II study in US adults" BMC Infection Diseases (2018) vol. 18(475) 11 pages. https://doi.org/10.1186/s12879-018-3389-x (published Sep. 21, 2018).
Roehrig, "Current status of dengue vaccine development," SAGE/Immunization Meeting, Apr. 2013. https://docplayer.net/21438920-Current-status-of-dengue-vaccine-development.html.
Sridhar et al., "Effect of Dengue Serostatus on Dengue Vaccine Safety and Efficacy" New England Journal of Medicine, published Jun. 13, 2018 at NEJM.org; https:doi.org/10.1056/NEJMoa1800820 (published Jul. 26, 2018).
Tran et al, "Long-term immunogenicity and safety of tetravalent dengue vaccine (CYD-TDV) in healthy populations in Singapore and Vietnam: 4-year follow-up of randomized, controlled, phase II trials"; Human Vaccines & Immunotherapeutics (2019); vol. 15(10); p. 2315-2327; https://doi.org/10.1080/21645515.2019.1578595.
Arredondo-Garcia et al., "Four-year safety follow-up of the tetravalent dengue vaccine efficacy randomized controlled trials in Asia and Latin America"; Clinical Microbiology & Infection (2018), vol. 24(7), p. 755-763; https://doi.org/10.1016/j.cmi.2018.01.018.
Guy et al, "Dengue vaccine: hypotheses to understand CYD-TDV-induced protection", Nat Rev Microbiol. Jan. 2016;14(1):45-54. doi: 10.1038/nrmicro.2015.2. Epub Dec. 7, 2015. Review.
Gailhardou et al, Safety Overview of a Recombinant Live-Attenuated Tetravalent Dengue Vaccine: Pooled Analysis of Data from 18 Clinical Trials. PLoS Negl Trop Dis. Jul. 14, 2016;10(7):e0004821. doi: 10.1371/journal.pntd.0004821. eCollection Jul. 2016.
Vigne et al, "Integrated immunogenicity analysis of a tetravalent dengue vaccine up to 4 y after vaccination", Hum Vaccin Immunot Sep. 2, 2017;13(9):2004-2016. doi: 10.1080/21645515.2017.1333211. Epub Jun. 9, 2017.
Olivera-Botello et al, "CYD-TDV Vaccine Trial Group. Tetravalent Dengue Vaccine Reduces Symptomatic and Asymptomatic Dengue Virus Infections in Healthy Children and Adolescents Aged 2-16 Years in Asia and Latin America", J Infect Dis., Oct. 1, 2016, 214(7):994-1000, doi: 10.1093/infdis/jiw297. Epub Jul. 14, 2016.
Coudeville L et al, "Potential impact of dengue vaccination: Insights from two large-scale phase III trials with a tetravalent dengue vaccine", Vaccine, Dec. 7, 2016, 34(50):6426-6435, doi: 10.1016/j.vaccine.2016.08.050. Epub Sep. 3, 2016.
Study of a Novel Tetravalent Dengue Vaccine in Healthy Children Aged 2 to 14 Years in Asia; ClinicalTrials.gov Identifier: NCT01373281;

(56) References Cited

OTHER PUBLICATIONS see Study Details, Tabular View & Study Results; https://clinicaltrials.gov/ct2/show/record/NCT01373281.
Study of a Novel Tetravalent Dengue Vaccine in Healthy Children and Adolescents Aged 9 to 16 Years in Latin America; ClinicalTrials.gov identifier: NCT01374516; see Study Details, Tabular View & Study Results; https://clinicaltrials.gov/ct2/show/NCT01374516.
clinicaltrials.gov Efficacy and safety of dengue vaccine in healthy children, see Study Details, Tabular View & Study Results; https://clinicaltrials.gov/ct2/show/NCT00842530.
Twiddy et al., "Phylogenetic relationships and differential selection pressures among genotypes of dengue-2 virus," Virology. 298(1):63-72 (2002) https://doi.org/10.1006/viro.2002.1447.
Deauvieau et al., "Innate immune responses in human dendritic cells upon infection by chimeric yellow-fever dengue vaccine serotypes 1-4," Am J Trap Med Hyq. 76(1):144-54 (2007).
DelAngel et al, "Dengue Vaccines: Strong Sought but Not a Reality Just Yet" PLOS 9(10): 61003551 (2013).
Dorigatti et al. "Refined efficacy estimates of the Sanofi Pasteur dengue vaccine CYD-TDV using machine learning", Nat Commun. 2018; 9: 3644; https://dx.doi.org/10.1038%2Fs41467-018-06006-6.
Hadinegoro et al., "Efficacy and Long-Term Safety of a Dengue Vaccine in Regions of Endemic Disease," N. Engl J Med. 373(13):1195-206 (2015) https://doi.org/10.1056/nejmoa1506223.
Moodie et al, "Neutralizing Antibody Correlates Analysis of Tetravalent Dengue Vaccine Efficacy Trials in Asia and Latin America," The Journal of Infectious Diseases 217: 742-753 (2018) https://doi.org/10.1093/infdis/jix609.
Morrison et al., "A novel tetravalent dengue vaccine is well tolerated and immunogenic against all 4 serotypes in flavivirus-naive adults," J Infect Dis. 201 (3):370-7 (2010) https://doi.org/10.1086/649916.
Osorio et al., "Development of DENVax: a chimeric dengue-2 PDK-53-based tetravalent vaccine for protection against dengue fever," Vaccine. 29(42):7251-60 (2011) https://www.ncbi.nlm.nih.gov/pmc/articles/PMC4592106/pdf/nihms724192.pdf.
Monath, Thomas P. M.D., "Dengue and Yellow Fever—Challenges for the Development and Uses of Vaccines", The New England J of Med., 357;22; Nov. 29, 2007; pp. 2222 to 2225.
Krogr, Andrew T, et al., "General Recommendations for Vaccination & Immunoprophylaxis", CDC; Chapter2 the Pre-Travel Consultation—Jul. 10, 2015; pp. 1-10.
Silva, Juliana R.M., et al., "Mutual Interference on the Immune Response to Yellow Fever Vaccine and a Combined Vaccine against Measles, Mumps and Rubella", Elsevier, Vaccine 29 (2011) 6327-6334.
Dayan et al., "Assessment of the long-term efficacy of a dengue vaccine against symptomatic, virologically-confirmed dengue disease by baseline dengue serostatus", Vaccine 38 (2020, 3551-3536, published Mar. 20, 2020).
Guy et al., "When Can One Vaccinate with a Live Vaccine after Wild-Type Dengue Infection?", Vaccines, 2020, 8 174 (published Apr. 9, 2020).
Crevat et al., "Safety and Immunogenicity of a Tetravalent Dengue Vaccine in Flavivirus-Naive and -Immune Pediatric Populations with Two Vaccination Regimens", Abstract 395 from American Journal of Tropical Medicine & Hygiene, vol. 81, 5(1), Nov. 1, 2009, p. 113 (cited in Mar. 3, 2020) Office Action in JP 2017-511914.
JP 2017-511914 English translation of office action—JPO dated Mar. 3, 2020, 2 pages.
DiazGranados et al., "CYD-TDV dengue vaccine performance by baseline immune profile (monotypic/multitypic) in dengue seropositive individuals", Clinical Infectious Diseases—ciaa304 (published Mar. 21, 2020), 26 pages.
Guy et al., "Immunogenicigty of sanofi pasteur tetravalent dengue vaccine", Jounal of Clinical Virology, 46, S2 (2009) 16-19.

\* cited by examiner

CONCOMITANT DENGUE AND YELLOW FEVER VACCINATION

CROSS-REFERENCE TO RELATED APPLICATIONS

This application is a U.S. national phase application under 35 USC 371 of International Patent Application no. PCT/EP2016/065580, filed Jul. 1, 2016, which claims the benefit of European Application no. 15306101.5, filed Jul. 3, 2015.

FIELD OF THE INVENTION

This invention relates to the field of multivalent vaccines.

BACKGROUND OF THE INVENTION

Dengue is the second most important infectious tropical disease after malaria with approximately one-half of the world's population living in areas where there is a risk of epidemic transmission. There are estimated to be 50-100 million cases of dengue fever every year resulting in 500,000 patients being hospitalized for hemorrhagic dengue fever and resulting in approximately 25,000 deaths. Dengue fever virus infections are endemic in more than 100 tropical countries and hemorrhagic dengue fever has been documented in 60 of these countries (Gubler, 2002, TRENDS in Microbiology, 10: 100-103; Monath, 1994, Proc. Natl. Acad. Sci., 91: 2395-2400).

Dengue fever is caused by four viruses of the flavivirus genus which are of similar serological type but differ antigenically (Gubler et al., 1988, in: Epidemiology of arthropod-borne viral disease. Monath T P M, editor, Boca Raton (Fla.): CRC Press: 223-60; Kautner et al., 1997, J. of Pediatrics, 131: 516-524; Rigau-Perez et al., 1998, Lancet, 352: 971-977; Vaughn et al., 1997, J. Infect. Dis., 176: 322-30). "Dengue fever viruses" or "dengue viruses" are positive single-strand RNA viruses belonging to the Flavivirus genus of the family of flaviviridae. The genomic sequence and organization of the dengue viral genome is well characterized in the art, see, e.g., Sughrue et al. (1997) J. General Virology 78(8): 1861-1866. Dengue virus particles are composed of three structural proteins: a genome associated capsid protein (nucleocapsid), a membrane associated protein (M) that is derived during virus maturation by internal cleavage from a glycosylated precursor protein (prM) and a membrane anchored hemagglutinating envelope protein (E). 180 copies of each the E and mature M proteins form a glycoprotein shell around the nucleocapsid. It is believed that E is the major antigenic determinant for serotype specificity, Markoff, J. (1989) J Virol. 63(8):3345-3352. However, the product of the prM gene, the glycosylated M protein and fragments thereof also possesses antigenic capacity capable of eliciting a specific immune response, Vasquez, et al. (2002) Vaccine 20: 1823-1830. The dengue virus genome comprises a 5' type I end but lacks a 3' poly-A tail. The organization of the genome is as follows: a 5' non-coding region (NCR), a region encoding the structural proteins (capsid (C), pre-membrane/membrane (prM/M), envelope (E)) and a region encoding non-structural proteins (NS1-NS2A-NS2B-NS3-NS4A-NS4B-NS5) and a 3' NCR. Typical of flaviviruses, the dengue viral genome encodes an uninterrupted coding region which is translated into a single polyprotein which is post-translationally processed.

Infection with one serotype of dengue may be asymptomatic or may produce a spectrum of clinical disease from non-specific viral syndrome to severe fatal hemorrhagic disease. Dengue fever is characterized by a two-phase fever, headaches, pains in various parts of the body, prostration, eruptions and lymphadenopathy (Kautner et al., 1997, J. of Pediatrics, 131: 516-524; Rigau-Perez et al., 1998, Lancet, 352: 971-977). The viremic period is of the same length as the febrile period (Vaughn et al., 1997, J. Infect. Dis., 176: 322-30). Cure of dengue fever is complete after 7 to 10 days, but prolonged asthenia is normal. Reduced leukocyte and platelet numbers frequently occur.

The effects of dengue virus infection are often more severe in children. Although the availability of multiple pediatric vaccines has alleviated the threat of multiple diseases in the pediatric population, the recommended administration regimen of these vaccines has created an increasingly complex and crowded schedule of vaccinations.

To date, there is no specific treatment for dengue disease. Treatment for dengue disease is symptomatic, with bed rest, control of the fever and pain through antipyretics and analgesics, and adequate drinking. The treatment of DHF requires balancing of liquid losses, replacement of coagulation factors and the infusion of heparin.

Since dengue prevention measures, such as mosquito control and personal protection from bites, are limited in efficacy, difficult to enforce and expensive, a safe and efficacious dengue vaccine appears as being one of the best mode of prevention. While no licensed dengue vaccine is yet available, several vaccine candidates are currently being evaluated in clinical studies (Schmitz J. et al., Vaccine, 29 (2011) 7276-7284).

The vaccine candidate currently at the most advanced clinical development stage is a live attenuated tetravalent dengue vaccine developed by Sanofi Pasteur (chimeric yellow fever dengue-tetravalent dengue vaccine or CYD-TDV). The safety and efficacy of this CYD-TDV in preventing dengue disease, based on a vaccination schedule of three doses given 6 months apart, has been demonstrated during the active phases of two Phase III clinical trials in Asia and Latin America (Capeding et al., The Lancet, 384(9951), 1358-1365 (2014) and Villar et al., NEJM, 372(2), 113-123).

The addition of a dengue vaccination to the already crowded childhood vaccination schedule raises issues of compliance, particularly in those areas of the world where regular healthcare is difficult to obtain. Unfortunately, these same areas are where the threat of dengue fever is particularly acute. One option is to combine multiple vaccines by concomitant administration to enhance compliance with the recommended vaccination schedule. However, the administration of multiple vaccines at a single time also creates issues for effective vaccination. Whenever a multivalent vaccine is administered (or multiple vaccines are concomitantly administered), each individual antigen of the combination induces an immunological response. It is possible to inhibit the immune system's ability to adequately respond to all of the antigens administered (e.g. via interference between two different antigens) and to not provide a durable protective response to one or more of the antigens. This effect is especially magnified in the case of live vaccines, which include live attenuated vaccines, since live vaccines must replicate in the host.

The Yellow Fever (YF) virus is considered the prototype of the Flaviviridae family, also represented by several other medically important viruses that cause serious diseases such as Dengue, Japanese Encephalitis and West Nile Fever. According to the World Health Organization (WHO), more than 200,000 cases of YF infection, including 30,000 deaths, occur annually worldwide. The safest strategy for disease prevention remains vaccination, since there is still no effective treatment for YF. Over the past 70 years more than 400 million people globally have been vaccinated with YF-attenuated virus (17DD) and it is considered to be very safe and effective. Despite the success of mass vaccination with 17DD, which is capable of inducing both lasting neutralizing antibody responses and cytotoxic T cell responses, rare adverse severe events (as a result of vaccination) have been reported in the literature [reviewed in (Liu, 2003)].

The YF virus is endemic, that is, continuously present with low levels of infection in some tropical areas of Africa and the Americas, where it regularly amplifies into epidemics. Other parts of the world, including coastal regions of South America, the Caribbean islands, and Central and North America, are infested with the mosquito vector capable of transmitting the virus and are therefore considered at risk for yellow fever epidemics (World Health Organization Fact Sheet No. 100, revised December, 2001). Although yellow fever cases have not been reported in Asia, "this region is at risk because the appropriate primates and mosquitoes are present" (Id.).

In the so-called "jungle" or "sylvan cycle", the YF virus is enzootic, maintained and transmitted by canopy breeding mosquitoes to monkeys in the rainforests. The "urban cycle" begins when humans become infected by entering the rainforests and are bitten by YF-infected mosquitoes. The "urban cycle" continues with peridomestic transmission from humans to mosquitoes and thence to other humans, and can result in yellow fever epidemics in villages and cities. Illness ranges in severity from a self-limited febrile illness to severe hepatitis and fatal hemorrhagic disease.

For the reasons above, there is a need in the art for vaccine strategies for generating an immune protection against both dengue virus and yellow fever virus.

When associating live virus vaccines, studies recommend that there is an interval of 30 days between the different vaccines in order to limit any possible interference (Advisory Committee on Immunization Practices (ACIP)—Center for Diseases Control (CDC). General Recommendations on immunization; MMWR Morb Mortal wkly Rep, 1994, Vol. 43(RR-1): 1-38). According to this ACIP-CDC report, the immune response to one live-virus vaccine may be impaired if administered within 30 days of another live-virus vaccine.

Regarding tetravalent dengue vaccines (which contain a vaccinal strain of each of the four serotypes of dengue), interference may occur between the different strains comprised within the vaccine. For example, association of DENV-2 and DENV-4 in a tetravalent vaccine demonstrated lower immunogenicity as compared with the equivalent monovalent formulations, as was evidenced by geometric mean titers (GMT) (Anderson et al., 2011, Journal of Infectious Diseases, Vol. 204: 442-450). Thus, even when concomitantly administering viral vectors of the same disease type, but from distinct virus serotypes, interference leading to lower immunogenicity may occur.

An interference effect has been reported following concomitant administration of a yellow fever vaccine with another vaccine.

For example, interference was reported following concomitant vaccination with (i) a yellow fever vaccine (YFV) and (ii) a combined vaccine against measles, mumps and rubella (MMR) (Silva et al., 2011, Vaccine, Vol. 29: 6327-6334). The authors showed that subjects concomitantly injected with YF and MMR vaccines had lower seroconversion rates as compared with those vaccinated 30 days apart. The authors further stated that the observed interference between YFV and MMR was consistent with previous observations from other live vaccines. Silva et al. (2011) believed that the results that they had obtained were likely to affect the recommendations regarding primary vaccination with yellow fever vaccine and MMR.

Significant reduction in the response to YF vaccine in children was also observed after administration of combined vaccine against smallpox and measles (Meyer et al., 1964, Bull World Health Organ, Vol. 30: 783-794). Similarly, significant reduction in the response to YF vaccine in children was observed after administration of combined vaccine against cholera (Felsenfeld et al., 1973, Lancet, Vol. 1: 457-458; Gateff et al., 1975, Ann Microbiol (Paris), Vol. 126(2): 231-2246). Yet further, significant reduction in the response to yellow fever vaccine in children was observed after administration of combined vaccine against hepatitis B (Yvonnet et al., J. of Med. Virol., 1986, Vol. 19: 307-311).

Beyond the interference effect that is discussed above, increased adverse effects may also be observed when performing concomitant vaccination. Illustratively, Silva et al. (2011) had shown that, in a concomitant vaccination with (i) a yellow fever vaccine and (ii) a combined vaccine against measles, mumps and rubella, the proportion of adverse effects was higher in the group vaccinated simultaneously, especially for fever. Also, Fisker et al. (2014, Vaccine, Vol. 32(5): 598-605) reported that co-administration of inactivated diphtheria-tetanus pertussis (DTP) vaccine and live attenuated measles vaccines (MV) is associated with increased mortality, as compared with subjects receiving MV only. These authors showed that the same increased mortality was observed when the pentavalent (DTP-H. Influenza type B-Hepatitis B) replaced DTP in a combination with MV.

In concomitant vaccination, even if the vaccines are administered to sites that are anatomically separate, there is still the potential for interference among the different vaccine agents. The immune system may be overstimulated or inhibited and as a result, may not adequately or optimally respond to the vaccination.

Thus, it flows from the teachings of the prior art that there is high uncertainty of the chance of inducing safe and effective immune protection simultaneously against a plurality of pathogenic viruses by concomitant vaccination. Moreover, the degree of uncertainty is further increased when a simultaneous immune protection against both yellow fever virus and dengue virus is sought, since the various drawbacks of concomitant vaccination involving either yellow fever virus or dengue virus are well known in the art.

SUMMARY OF THE INVENTION

The present invention relates to a yellow fever (YF) vaccine for use in a method for inducing a protective immune response against yellow fever, wherein said method comprises concomitantly administering said yellow fever vaccine to a human subject together with a tetravalent dengue vaccine which comprises a live attenuated dengue virus of each of serotypes 1 to 4.

This invention also relates to a tetravalent dengue vaccine which comprises a live attenuated dengue antigen of each of serotypes 1 to 4, for use in a method for inducing a protective immune response against yellow fever, wherein said method comprises concomitantly administering said tetravalent dengue vaccine to a human subject together with a yellow fever (YF) vaccine.

In some embodiments, the tetravalent dengue vaccine is administered according to a three-dose vaccination schedule, the first dose of the tetravalent dengue vaccine being concomitantly administered with the Yellow fever (YF) vaccine.

This invention also relates to a vaccine composition comprising a mixture of a yellow fever vaccine and of a live attenuated tetravalent dengue vaccine a tetravalent dengue vaccine which comprises a live attenuated dengue virus of each of serotypes 1 to 4.

In some embodiments, the yellow fever (YF) vaccine comprises a live attenuated yellow fever virus strain.

The present invention further relates to vaccine composition for use in a method for inducing a protective immune response against dengue disease, wherein said method comprises administering to a human subject at least one composition comprising a tetravalent dengue vaccine which comprises a live attenuated dengue antigen of each of serotypes 1 to 4, and wherein said method comprises administering said composition in a first dose, a second dose and a third dose and wherein said second dose is to be administered about two months after said first dose and wherein said third dose is to be administered about six months after said first dose.

In some embodiments, the tetravalent dengue vaccine comprises a recombinant chimeric virus of each of the four serotypes of dengue with each virus comprising a yellow fever genomic backbone wherein the preM-E region is the preM-E region of dengue virus.

As previously mentioned, the tetravalent dengue vaccine comprises a live attenuated dengue virus of each of serotypes 1 to 4.

AEs, adverse events; SAEs, serious adverse events.

Group 1. 1st injection: yellow fever vaccine+CYD-TDV injection at enrollment (Month 0). 2nd injection: CYD-TDV injection at Month 6. 3rd injection: CYD-TDV injection at Month 12.

Group 2. 1st injection: yellow fever vaccine+placebo at enrollment (Month 0). 2nd injection: CYD-TDV injection at Month 6. 3rd injection: CYD-TDV injection at Month 12.

y axis: percent of participants x axis, or each group of bars, from left bar to right bar:
first (left) bar: immediate AEs,
second bar: Solicited injection site reactions (Day 0-7),
third bar: Solicited systemic reactions (Day 0-14), and
fourth (right) bar: Unsolicited AEs (Day 0-28).

Figure 3:
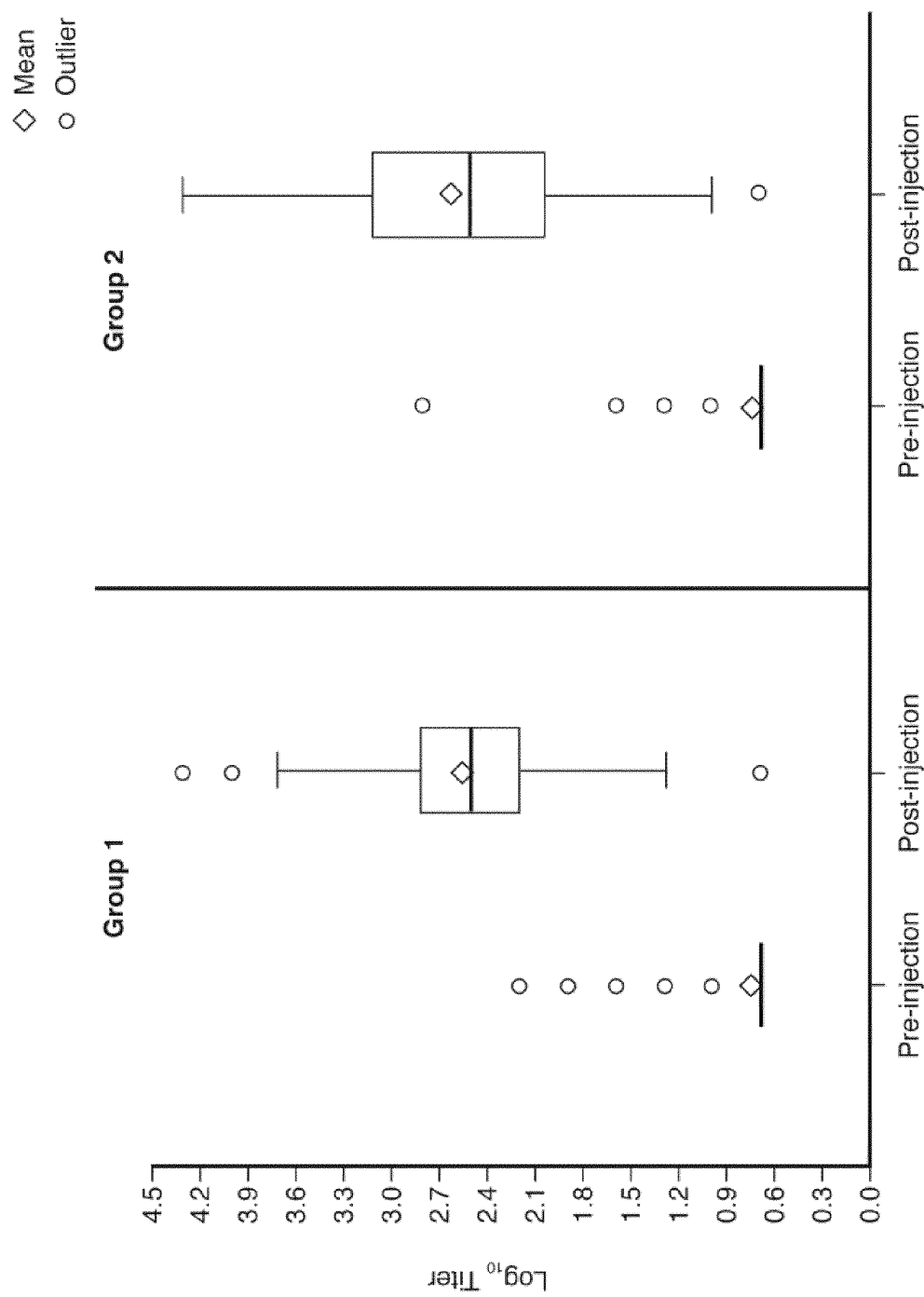

FIG. 3: Box plots for yellow fever $\log_{10}$ antibody titers before and 28 days after administration of the yellow fever vaccine concomitantly with a dengue vaccine candidate (Group 1—left part of FIG. 3) or concomitantly with a placebo (Group 2—right part of FIG. 3) (intent-to-treat set).

y axis: $\log_{10}$ yellow fever antibody titer x axis: left data points, pre-injection; right data points, post-injection.

◇: Mean value

○: Outlier value

Figure 4:
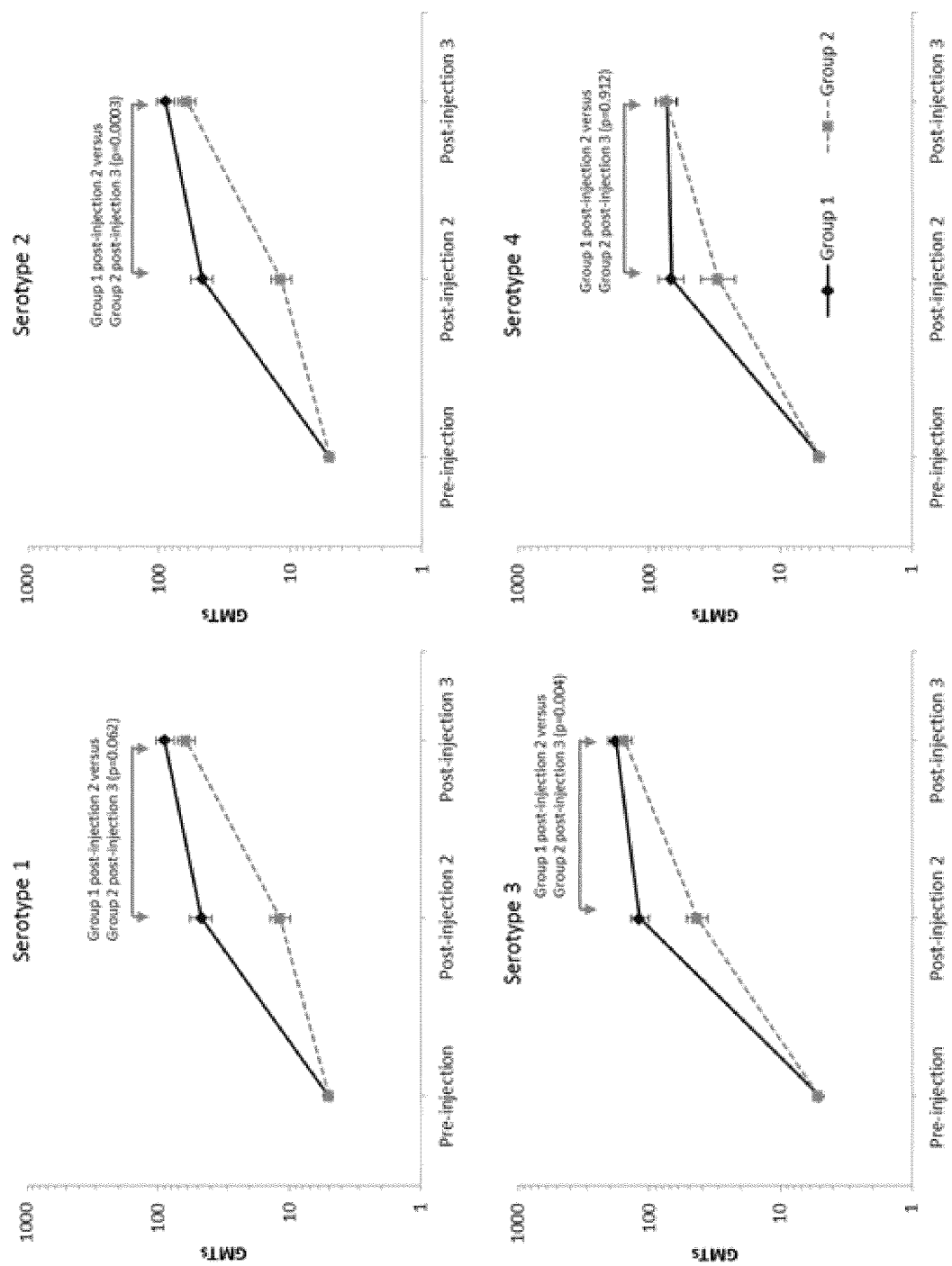

FIG. 4: Geometric mean titers for dengue serotypes 1, 2, 3 and 4, 30 days after the second dengue vaccination (Groups 1 and 2) and third dengue vaccination (Group 1), (intent-to-treat set—dengue immunogenicity). Statistical comparison shown following two doses of CYD-TDV Upper left part of FIG. 3: Dengue serotype 1, wherein Group 1 post-injection 2 versus Group 2 post-injection 3 reveals a p of 0.062, Upper right part of FIG. 3: Dengue serotype 2, wherein Group 1 post-injection 2 versus Group 2 post-injection 3 reveals a p of 0.0003, Bottom left part of FIG. 3: Dengue serotype 3, wherein Group 1 post-injection 2 versus Group 2 post-injection 3 reveals a p of 0.004, and Bottom right part of FIG. 3: Serotype 4, wherein Group 1 post-injection 2 versus Group 2 post-injection 3 reveals a p of 0.912.

y axis: geometric mean titers (GMTs)

x axis, from left to right, respectively: (i) pre-injection, (ii) post-injection 2, (iii) post-injection 3.

black ♦: Group 1 of patients grey ■: Group 2 of patients

DETAILED DESCRIPTION OF THE INVENTION

The present inventors have shown that, unexpectedly, the administration of a yellow fever (YF) vaccine concomitantly with a tetravalent dengue vaccine which comprises a live attenuated dengue virus of each of serotypes 1 to 4 provides protective immunity against yellow fever. Further, the inventors have shown that the concomitant administration of a yellow fever vaccine with a tetravalent dengue vaccine which comprises a live attenuated dengue virus of each of serotypes 1 to 4 does not affect the immunogenicity and the safety of the yellow fever vaccine and the tetravalent dengue vaccine.

It has also been shown by the inventors that concomitant administration of a yellow fever vaccine with a tetravalent dengue vaccine which comprises a live attenuated dengue virus of each of serotypes 1 to 4 results in a good antibody response against yellow fever, thus fulfilling the prospective statistical criteria of non-inferiority along with no clinically relevant impact on the safety profile of the yellow fever vaccine in humans, especially in small children.

Further, it has been shown herein that concomitant administration of a yellow fever vaccine with a tetravalent dengue vaccine which comprises a live attenuated dengue virus of each of serotypes 1 to 4 results in a good antibody response against dengue, thus fulfilling the prospective statistical criteria of non-inferiority along with no clinically relevant impact on the safety profile of the dengue vaccine in humans, especially in small children.

The induction of protective immunity against yellow fever virus has been shown herein, including in embodiments wherein the yellow fever virus is concomitantly administered with a tetravalent dengue vaccine which comprises a live attenuated chimeric yellow fever-dengue virus of each of serotypes 1 to 4, i.e. a chimeric yellow fever virus which comprises the genomic backbone of a yellow fever virus in which the sequences encoding the envelope (E) protein (and more preferably the pre-membrane (prM) and E proteins) have been replaced by nucleic acid sequences encoding the corresponding structural proteins of a dengue virus. It has thus unexpectedly been shown herein that the yellow fever protein backbone of the chimeric dengue virus does not generate an interaction or an interference with the expected immune response generated by a yellow fever vaccine which is concomitantly administered therewith.

Accordingly, it is shown herein that the concomitant administration of yellow fever vaccine with a tetravalent dengue vaccine which comprises a live attenuated dengue virus of each of serotypes 1 to 4 results in a good yellow fever antibody response, with no clinically relevant impact on the immunogenicity or safety profile of the yellow fever vaccine. Both vaccines may therefore be administered to children at the same visit, offering benefits to public health whilst minimizing healthcare resources.

This invention relates to:
- a yellow fever (YF) vaccine for use in a method for inducing a protective immune response against yellow fever, wherein said method comprises concomitantly administering said yellow fever vaccine to a human subject together with a tetravalent dengue vaccine which comprises a live attenuated dengue virus of each of serotypes 1 to 4,
- a yellow fever vaccine for use in a method for inducing a protective immune response against dengue, wherein said method comprises concomitantly administering said yellow fever vaccine to a human subject together with a tetravalent dengue vaccine which comprises a live attenuated dengue virus of each of serotypes 1 to 4,
- a yellow fever vaccine for use in a method for inducing a protective immune response against both yellow fever and dengue, wherein said method comprises concomitantly administering said yellow fever vaccine to a human subject together with a tetravalent dengue vaccine which comprises a live attenuated dengue virus of each of serotypes 1 to 4,
- a yellow fever vaccine for use in a method for inducing a neutralizing antibody response against both yellow fever and dengue, wherein said method comprises concomitantly administering said yellow fever vaccine to a human subject together with a tetravalent dengue vaccine which comprises a live attenuated dengue virus of each of serotypes 1 to 4,
- a yellow fever vaccine for use in a method for inducing a protective immune response against yellow fever and a neutralizing antibody response against each of the four serotypes of dengue, wherein said method comprises concomitantly administering said yellow fever vaccine to a human subject together with a tetravalent dengue vaccine which comprises a live attenuated dengue virus of each of serotypes 1 to 4,
- a tetravalent dengue vaccine which comprises a live attenuated dengue virus of each of serotypes 1 to 4 for use in a method for inducing a protective immune response against both dengue and yellow fever, wherein said method comprises concomitantly administering said tetravalent dengue vaccine to a human subject together with a yellow fever vaccine,
- a tetravalent dengue vaccine which comprises a live attenuated dengue antigen of each of serotypes 1 to 4, for use in a method for inducing a neutralizing antibody response against both dengue and yellow fever, wherein said method comprises concomitantly administering said tetravalent dengue vaccine to a human subject together with a yellow fever (YF) vaccine,
- a tetravalent dengue vaccine which comprises a live attenuated dengue antigen of each of serotypes 1 to 4, for use in a method for inducing a neutralizing antibody response against yellow fever, wherein said method comprises concomitantly administering said tetravalent dengue vaccine to a human subject together with a yellow fever (YF) vaccine,
- a tetravalent dengue vaccine which comprises a live attenuated dengue antigen of each of serotypes 1 to 4, for use in a method for inducing a neutralizing antibody response against dengue, wherein said method comprises concomitantly administering said tetravalent dengue vaccine to a human subject together with a yellow fever (YF) vaccine,
- a tetravalent dengue vaccine which comprises a live attenuated dengue antigen of each of serotypes 1 to 4, for use in a method for inducing a protective immune response against yellow fever, wherein said method comprises concomitantly administering said tetravalent dengue vaccine to a human subject together with a yellow fever (YF) vaccine,
- a tetravalent dengue vaccine which comprises a live attenuated dengue antigen of each of serotypes 1 to 4, for use in a method for inducing a protective immune response against yellow fever and a neutralizing antibody response against each of the four serotypes of dengue, wherein said method comprises concomitantly administering said tetravalent dengue vaccine to a human subject together with a yellow fever (YF) vaccine,
- the use of a yellow fever antigen for the manufacture of a yellow fever vaccine for protecting a human subject against yellow fever, wherein the said yellow fever vaccine is intended for use in a method for inducing a protective immune response against yellow fever, which method comprises concomitantly administering to said human subject said yellow fever vaccine and a tetravalent dengue vaccine which comprises a live attenuated dengue virus of each of serotypes 1 to 4,
- the use of a yellow fever antigen for the manufacture of a yellow fever vaccine for protecting a human subject against yellow fever, wherein the said yellow fever vaccine is intended for use in a method for inducing a protective immune response against dengue, which method comprises concomitantly administering to said human subject said yellow fever vaccine and a tetravalent dengue vaccine which comprises a live attenuated dengue virus of each of serotypes 1 to 4
- the use of a yellow fever antigen for the manufacture of a yellow fever vaccine for protecting a human subject against yellow fever, wherein the said yellow fever vaccine is intended for use in a method for inducing a protective immune response against both yellow fever and dengue, which method comprises concomitantly administering to said human subject said yellow fever vaccine and a tetravalent dengue vaccine which comprises a live attenuated dengue virus of each of serotypes 1 to 4,
- the use of a yellow fever antigen for the manufacture of a yellow fever vaccine for protecting a human subject against yellow fever, wherein the said yellow fever vaccine is intended for use in a method for inducing a neutralizing antibody response against dengue, which method comprises concomitantly administering to said human subject said yellow fever vaccine and a tetravalent dengue vaccine which comprises a live attenuated dengue virus of each of serotypes 1 to 4,
- the use of live attenuated dengue viruses of each of serotypes 1 to 4 for the manufacture of a tetravalent dengue vaccine for protecting a human subject against dengue virus, wherein the said dengue vaccine is intended for use in a method for inducing a protective immune response against dengue, which method comprises concomitantly administering to said subject said tetravalent dengue vaccine and a yellow fever vaccine,
- the use of live attenuated dengue viruses of each of serotypes 1 to 4 for the manufacture of a tetravalent dengue vaccine for protecting a human subject against dengue virus, wherein the said dengue vaccine is intended for use in a method for inducing a protective immune response against yellow fever, which method comprises concomitantly administering to said subject said tetravalent dengue vaccine and a yellow fever vaccine, the use of live attenuated dengue viruses of each of serotypes 1 to 4 for the manufacture of a tetravalent dengue vaccine for protecting a human subject against dengue virus, wherein the said dengue vaccine is intended for use in a method for inducing a protective immune response against both yellow fever and dengue, which method comprises concomitantly administering to said subject said tetravalent dengue vaccine and a yellow fever vaccine, and to the use of live attenuated dengue viruses of each of serotypes 1 to 4 for the manufacture of a tetravalent dengue vaccine, wherein the said dengue vaccine is intended for use in a method for inducing a neutralizing antibody response against dengue in a human subject, which method comprises concomitantly administering to said subject said tetravalent dengue vaccine and a yellow fever vaccine.

This invention also concerns a method for inducing a protective immune response against yellow fever which comprises concomitantly administering to a human subject a yellow fever vaccine and a tetravalent dengue vaccine which comprises a live attenuated dengue virus of each of serotypes 1 to 4.

This invention also relates to a method for inducing a protective immune response against yellow fever and a neutralizing antibody response against each of the four serotypes of dengue, which comprises concomitantly administering to a human subject a yellow fever vaccine and a tetravalent dengue vaccine which comprises a live attenuated dengue virus of each of serotypes 1 to 4.

The expressions "inducing a neutralizing antibody response against each of the four serotypes of dengue", "inducing neutralizing antibodies against all four serotypes 1 to 4 of dengue" and "inducing the production of neutralizing antibodies against all four serotypes 1 to 4 of dengue" can be used interchangeably in the present text as they have the same meaning.

The same applies between the terms "against all four serotypes 1 to 4 of dengue" and "against each of the four serotypes of dengue".

This invention also pertains to a method for inducing a protective immune response against yellow fever which comprises:

(i) concomitantly administering to a human subject a yellow fever vaccine and a first dose of a tetravalent dengue vaccine which comprises a live attenuated dengue virus of each of serotypes 1 to 4, and (ii) administering a second dose of a tetravalent dengue vaccine which comprises a live attenuated dengue virus of each of serotypes 1 to 4 in a time period ranging from 1 month to 9 months following the administration of the first dose of a dengue vaccine.

This invention further relates to a method for inducing a protective immune response against yellow fever which comprises:

(i) concomitantly administering to a human subject a yellow fever vaccine and a first dose of a tetravalent dengue vaccine which comprises a live attenuated dengue virus of each of serotypes 1 to 4, (ii) administering a second dose of a tetravalent dengue vaccine which comprises a live attenuated dengue virus of each of serotypes 1 to 4 in a time period ranging from 1 month to 9 months following the administration of the first dose of a tetravalent dengue vaccine, and (iii) administering a third dose of a tetravalent dengue vaccine which comprises a live attenuated dengue virus of each of serotypes 1 to 4 in a time period ranging from 1 month to 9 months following the administration of the second dose of a tetravalent dengue vaccine.

This invention further pertains to:

a kit comprising a yellow fever vaccine together with instructions for concomitantly administering to a human subject a yellow fever vaccine and a tetravalent dengue vaccine which comprises a live attenuated dengue virus of each of serotypes 1 to 4, and to a kit comprising a tetravalent dengue vaccine which comprises a live attenuated dengue virus of each of serotypes 1 to 4 together with instructions for concomitantly administering to a human subject a tetravalent dengue vaccine and a yellow fever vaccine.

Besides, the present inventors have shown that, unexpectedly, the administration to a human subject of at least one composition comprising a tetravalent dengue vaccine which comprises a live attenuated dengue antigen of each of serotypes 1 to 4, and wherein said administration is based on a three-dose vaccination schedule "0-2-6 months", namely wherein a second dose is to be administered about two months after the first dose and wherein a third dose is to be administered about six months after the first dose, (1) provides a balanced neutralising antibody response against all four serotypes of dengue (which is non-inferior to the antibody response provided by a 0-6-12 three-dose vaccination schedule) and (2) does not affect the safety of the tetravalent dengue vaccine.

This result is totally unexpected in view of the knowledge of the man skilled in the art. Indeed, the results displayed notably in Rosario Z. et al. (Vaccine 29 (2011) 3863-3872) and in Morrison et al. (The Journal of Infectious Diseases 2010; 201: 370-7), directed the development of the immunization schedule towards a three-dose vaccination schedule, 6 months apart (i.e. 0-6-12), which was hypothesized to limit short-term viral interference between doses and/or allows a better maturation of immune memory.

Therefore, a three dose vaccination schedule "0-2-6 months" goes against the conclusions from notably Rosario Z. et al. and Morrison et al. and thus from the general knowledge of the man skilled in the art.

By "concomitant administration" or "concomitantly administering" is meant the action of administering at least two products substantially at the same time—that is within 3 days or less and most preferably on the same day, preferably within an interval of a few minutes. If necessary, the at least two products may also be administered some hours apart. For example, concomitant administration means administering the at least two products within 3 days, 2 days, 24 hours, 12 hours, 6 hours, 3 hours, 2 hours, 1 hour, 30 minutes, 15 minutes or simultaneously. Advantageously, the at least two products are administered at anatomically separate body sites. In the context of the present invention, two anatomical sites are separate if they are drained by different lymph nodes. For example, the right arm and the left arm are considered to be separate sites. The following separate sites may also be mentioned by way of non-limiting examples: right arm/right thigh; left arm/left thigh; left arm/right thigh. The at least two products may alternatively be mixed together before administration and the resulting mixture is administered at the selected body site, e.g. in the left arm or in the right arm. As a further alternative, the at least two products may be concomitantly administered to the selected body site using a double-barreled syringe.

Hereinafter, the term "dose" refers to a volume of a vaccine or vaccine composition comprising an "immunoeffective amount" of the antigenic material(s) (i.e. vaccinal virus (yellow fever vaccine strain or dengue serotypes 1 to 4). An immunoeffective amount is an amount of the antigenic material(s) that is sufficient to induce a neutralizing antibody response after the completion of the immunization regime.

A dose, composition or vaccine is termed "monovalent" when in addition to a pharmaceutically acceptable excipient, it contains an antigen(s) derived from a single strain or serotype of a microorganism, which is designed to elicit a neutralizing antibody response against that particular strain or serotype of microorganism. A dose, composition or vaccine is termed "multivalent" when it contains antigens from multiple strains or serotypes of a microorganism or antigens from multiple microorganisms. A multivalent dose, composition or vaccine is designed to elicit neutralizing antibodies against multiple strains or serotypes of a microorganism or neutralizing antibodies against different organisms. The nomenclature used is consistent with conventional nomenclature. For example, a dose, composition or vaccine is considered bivalent, trivalent or tetravalent when it contains antigens designed to elicit neutralizing antibodies against two, three or four serotypes of a microorganism or two, three or four different microorganisms respectively. Multivalent compositions may be prepared by simple mixing of monovalent compositions. As used herein, a "tetravalent dengue composition" or "tetravalent dengue vaccine" comprises antigens which induce neutralizing antibodies against all four serotypes 1 to 4 of dengue.

In the context of the present invention, the term "vaccinal dengue composition" refers to a composition comprising live attenuated vaccinal dengue viruses.

In the context of the present invention, "a tetravalent dengue vaccine" refers to a dengue vaccine which is capable of inducing neutralizing antibodies against each of the serotypes 1 to 4 of dengue virus by the administration of such dengue vaccine to an immunocompetent mammal, e.g. a human. Examples of vaccinal dengue viruses useful in a tetravalent dengue vaccine of the invention include live attenuated dengue viruses. A particular example of a live attenuated dengue virus is a live attenuated chimeric dengue virus.

A "live attenuated virus" is a virus which replicates in a permissive host cell but the replicative efficiency of which is reduced relative to the wild-type virus in the same host cell type. Attenuated viruses can replicate in a host, but do not induce a disease state associated with the wild-type virus in said host. Examples of attenuated viruses are known in the art. An attenuated virus may be prepared, for example, from a wild-type virus by recombinant DNA technology, site directed mutagenesis, genetic manipulation, serial passage, chemical treatment, chemical mutagenesis or electromagnetic radiation. An attenuated virus useful in the present invention may generate side effects of moderate intensity (i.e. medium to slight, or none) in the majority of vaccinated subjects, while retaining its ability to induce neutralizing antibodies in a mammal.

Although attenuated viruses replicate to a lesser degree than wild-type viruses in typical host cells, such attenuated viruses may be produced efficiently in cells which are able to complement functions disrupted in the attenuated virus ("producer cells"). Producer cells may be naturally occurring variants of permissive host cells or may be generated by other means such recombinant DNA technology. In preparing engineered producer cells using recombinant DNA technology, the cell may be modified by the insertion of exogenous nucleic acids which complement the functions which are disrupted in the attenuated virus. Such exogenous nucleic acids may be incorporated into the genome of the cell or may be maintained extra-chromosomally.

A tetravalent dengue vaccine used in the context of the practice of the present invention comprises a live attenuated dengue virus of each of serotypes 1, 2, 3 and 4. In one embodiment, the tetravalent live attenuated dengue virus is a live attenuated dengue virus that possesses a replicative efficiency in a permissive cell type is at least one order of magnitude less than the wild type virus in the same cell type. In other embodiments, the attenuated dengue virus is attenuated for replication to a degree of at least two orders of magnitude, three orders of magnitude, four orders of magnitude, five orders of magnitude, six orders of magnitude, seven orders of magnitude or more relative to the wild type virus in the same cell type.

In one embodiment, the growth of the live attenuated dengue virus of each of serotypes 1 to 4 at 37° C. or 39° C. in Huh-7, VERO and/or C6/36 liver cells results in a maximum titer which is at least 10 times less than maximum titer obtained with the wild parent strain under the same culture conditions and as measured using a given method for determining titer. Examples of live attenuated dengue viruses useful in the practice of the present invention include the VDV1 strain, the VDV2 strain, and the strains described for example in applications WO 2002/66621, WO 00/57904, WO 00/57908, WO 00/57909, WO 00/57910, WO 2002/0950075 and WO 2002/102828.

"VDV" or "Vero dengue vaccine" designates an attenuated dengue virus capable of replication in Vero cells and capable of inducing a specific humoral response, including the induction of neutralizing antibodies, in a mammal. VDV1 is a virus derived from a live attenuated dengue virus of serotype 1 known as 16007/PDK13, also called LAV1. LAV1 was derived from the wild-type DEN-1 (dengue virus serotype 1) 16007 strain by submitting the wild type strain to 13 passages through primary dog kidney (PDK) cells. LAV1 has been described in EP1159968 and has been filed with the National Microorganisms Cultures Collection (CNCM, Institut Pasteur, Paris, France) under number 1-2480. VDV1 was derived from LAV1 by subsequent adaptation to Vero cells; in this regard, the RNA from LAV1 was extracted and purified before being transfected into Vero cells. The VDV1 strain has subsequently been obtained by plate purification and amplification in Vero cells. The VDV1 strain has 3 additional mutations in comparison with LAV1. The complete nucleotide sequence of the VDV1 strain, as well as a process for preparing and characterizing the VDV1 strain have been described in international patent publication WO 2006/134433.

"VDV2" is a strain derived from a live attenuated dengue virus of serotype 2 known as 16681/PDK53, also called LAV2. LAV2 was derived from the wild-type DEN-2 (dengue virus serotype 2) 16681 strain by submitting the wild type strain to 53 passes through PDK cells. LAV2 has been described in EP1159968 and has been filed with the National Microorganisms Cultures Collection (CNCM, Institut Pasteur, Paris, France) under number 1-2481. VDV2 was derived from LAV2 by subsequent adaptation to Vero cells; in this regard, the RNA from LAV2 was extracted and purified before being transfected in Vero cells. The VDV2 strain was subsequently obtained by plate purification and amplification in Vero cells. The VDV2 strain has 10 additional mutations in comparison with the LAV2 strain, including 3 silent mutations and 1 mutation in a non-coding region. The complete nucleotide sequence of the VDV2 strain, as well as a process for preparing and characterizing the VDV2 strain have been described in the international patent publication WO 2006/134443.

A live attenuated dengue virus of the present invention may also be a live attenuated chimeric dengue virus.

In the context of the invention, "chimeric dengue virus" or "dengue chimera" means a recipient flavivirus in which the genetic backbone has been modified by exchanging the sequence of at least the envelope (E) protein of the recipient flavivirus by the corresponding sequence of a dengue virus. Alternatively, and more preferably, the genetic backbone of the recipient flavivirus is modified by exchanging the nucleic acid sequences encoding both the pre-membrane (prM) and E proteins of the recipient flavivirus by the corresponding sequences of a dengue virus. Typically, the recipient flavivirus may be attenuated. The recipient flavivirus may be a yellow fever (YF) virus, in which case, the chimera is referred to herein as a "chimeric YF/dengue virus". Preferably, the YF backbone of a chimeric YF/dengue virus according to the present invention is from an attenuated YF virus. The recipient flavivirus may also be a dengue virus and in that case, the chimeric dengue virus is referred to herein as a "chimeric dengue/dengue virus", the dengue virus serotype characteristic of the E or the prM and E proteins being identical or different from the recipient dengue virus serotype characteristic of the genetic backbone. When the recipient flavivirus is a dengue virus, said dengue virus is preferably attenuated. When the serotypes of the recipient and donor dengue viruses are identical, the recipient dengue virus and the donor dengue virus from which the prM and E protein encoding sequences originate are two different virus strains of the same serotype. For use in the present invention, chimeric dengue viruses are typically chimeric YF/dengue viruses. Examples of chimeric viruses useful in the practice of the present invention include the dengue/YF chimeric viruses described in patent application WO 98/37911 and the dengue/dengue fever chimeras such as those described in patent applications WO 96/40933 and WO 01/60847.

In one embodiment, the chimeric YF/dengue virus comprises the genomic backbone of the attenuated yellow fever virus strain YF17D (Theiler M. and Smith H. H. (1937) J. Exp. Med., 65, p. 767-786) (viruses YF17D/DEN-1, YF17D/DEN-2, YF17D/DEN-3, YF 1 7D/DEN-4). Examples of YF17D strains which may be used include YF17D204 (YF-VAX®, Sanofi-Pasteur, Swiftwater, Pa., USA; Stamaril®, Sanofi-Pasteur, Marcy I'Etoile, France; ARILVAX™, Chiron, Speke, Liverpool, UK; FLAVIMUN®, Berna Biotech, Bern, Switzerland; YF17D-204 France (X15067, X15062); YF17D-204,234 US (Rice et al., 1985, Science, 229: 726-733), or again the related strains YF17DD (Genbank access number U17066), YF17D-213 (Genbank access number U17067) and the strains YF17DD described by Galler et al. (1998, Vaccines, 16(9/10): 1024-1028). Any other attenuated yellow fever virus strain which may be used in man may be used to construct chimeras in the context of this invention.

One example of a chimeric YF/dengue virus suitable for use in the practice of the present invention is the "Chimerivax™ dengue" or "CYD", a chimeric yellow fever (YF) virus which comprises the genomic backbone of an attenuated YF virus in which the sequences coding for the pre-membrane (prM) and envelope (E) proteins have been replaced by nucleic acid sequences encoding the corresponding structural proteins of a dengue virus. Construction of chimeric Chimerivax virus may be achieved in substantial accordance with the teaching of Chambers et al. (1999) J Virology 73(4):3095-3101. A chimeric dengue virus containing the prM and E sequences of a serotype 1 dengue fever strain (DEN-1) is referred to as "CYD-1 or CYD DEN1". A chimeric YF containing the prM and E sequences of a DEN-2 strain is referred as "CYD-2 or CYD DEN2". A chimeric YF virus containing the prM and E sequences of a DEN-3 strain is referred to as "CYD-3 or CYD DEN3". A chimeric dengue virus containing the prM and E sequences of a DEN-4 strain is referred to as "CYD-4 or CYD DEN4". The preparation of these dengue Chimerivax™ viruses have been described in detail in international patent applications WO 98/37911 and WO 03/101397, to which reference may be made for a precise description of the processes for their preparation. The chimeras may be generated by using prM and E sequences from strains DEN 1 PUO359 (TYP1140), DEN2 PUO218, DEN3 PaH881/88 and DEN 4 1228 (TVP 980). Alternatively, other dengue fever virus strains may be used as a source of nucleic acids to facilitate construction of chimeric viruses useful in the practice of the present invention. The sequences SEQ ID NOs 1 to 4 corresponding to the nucleotide sequences of the prM-E regions of the chimeras of serotypes 1 to 4 described in the examples are set out in the Table below. The sequence SEQ ID N° 5, corresponding to the nucleotide sequence of the prM-E region of different serotype 2 strain (MD1280), is set out in the Table below under the designation "CYD-2V". Sequences having at least 90% sequence identity to the sequences of SEQ ID NOs 1-5 may be used as a source of nucleic acids to facilitate construction of chimeric viruses useful in the practice of the present invention. Use of CYD-2V in combination with chimeric YF/DEN strains of serotypes 1, 3 and 4 which are respectively based on the prM-E sequences of SEQ ID NOs 1, 3 and 4 results in a tetravalent dengue vaccine that produces a more balanced neutralising immune response across the four serotypes (as described in WO 2014/016, 362).

Alternatively, other dengue fever virus strains may be used as a source of nucleic acids to facilitate construction of chimeric viruses useful in the practice of the present invention.

An example of a live attenuated dengue virus of serotype 1 useful in the present invention may for example be the strain VDV1, a Chimerivax™ DEN-1 or a YF17D/DEN-1 chimeric virus comprising the prM and E genes of the DEN-1 16007/PDK13 strain. An example of a live attenuated dengue virus of serotype 2 useful in the present invention is the strain VDV2, a Chimerivax™ DEN-2 or a YF17D/DEN-2 chimeric virus comprising prM and E genes of the DEN-2 16681/PDK53 strain. An example of a live attenuated dengue virus of serotype 3 useful in the present invention is a Chimerivax™ DEN-3 or a YF17D/DEN-3 chimeric virus. An example of a live attenuated virus of serotype 4 useful in the present invention is a Chimerivax™ DEN-4 or a YF17D/DEN-4 chimeric virus. The skilled artisan may refer to the aforementioned published international patent applications for a detailed description of the strains mentioned, the processes for obtaining them and the construction of these chimeric viruses. The SEQ ID NOs 6 and 7 corresponding to the nucleotide sequences of the above-mentioned VDV1 and VDV2 strains are set out in the Table below.

The ability of a vaccine composition of the present invention to provoke an immune response in a human subject (i.e. induce the production of neutralizing antibodies) can be assessed, for example, by measuring the neutralizing antibody titre raised against the dengue virus serotype(s) comprised within the composition. The neutralizing antibody titre may be measured by the Plaque Reduction Neutralization Test (PRNT$_{50}$ or PRNT$_{80}$), as described in the Examples. It has been commonly considered that seroconversion occurs when the titre is superior or equal to 10 (l/dil). As PRNT tests may slightly vary from a laboratory to another the LLOQ may also slightly vary. Accordingly, in a general manner, it is considered that seroconversion occurs when the titre is superior or equal to the LLOQ of the test.

For use in the present invention, a yellow fever (YF) vaccine may be any YF commercialized vaccine, which are all composed of a live attenuated YF virus strain, in particular the 17D-204 strain. The YF virus strain is cultured in specified pathogen-free chick embryos. The virus is collected, purified and then lyophilized using a stabilizing medium. The lyophilized powder is extemporaneously reconstituted with an excipient before use.

The immunogenicity of the YF vaccine may be assessed while measuring the YF neutralizing antibody in a plaque reduction neutralization test (PRNT), as described in the Examples.

A YF vaccine dose usually contains not less than 1000 LD50 units of the virus (the statistically determined lethal dose in 50% of animals tested) in a volume of from 0.1 to 1 ml, preferably 0.5 ml.

The YF vaccine for use in the present invention may be administered according to any route conventional in the vaccine field, for example parenterally, in particular, intradermally, subcutaneously or intramuscularly. Preferably, the YF vaccine is administered subcutaneously or intramuscularly.

In some embodiments, this invention relates to a combined vaccine composition comprising a mixture of a yellow fever vaccine and of a tetravalent dengue vaccine which comprises a live attenuated dengue virus of each of serotypes 1 to 4. Various embodiments of a yellow fever vaccine and of a tetravalent dengue vaccine which comprises a live attenuated dengue virus of each of serotypes 1 to 4 are described elsewhere in the present specification.

In some embodiments, the said combined vaccine composition comprises a mixture of:
a yellow fever vaccine in an amount sufficient for inducing a protective immune response in a human subject, and
a tetravalent dengue vaccine which comprises a live attenuated dengue virus of each of serotypes 1 to 4 in an amount sufficient for a first dose of a dengue vaccine adapted for a three-dose dengue vaccination schedule in a human subject.

In some embodiments, the said combined vaccine composition is manufactured as a ready-to-use vaccine. In some other embodiments, the said combined vaccine is prepared a short time period, e.g. one hour or less, before administration to a subject, for example by simply mixing a dose of a tetravalent dengue vaccine which comprises a live attenuated dengue virus of each of serotypes 1 to 4 with a dose of a yellow fever vaccine and then administering the resulting vaccine mixture to the said subject, whereby the yellow fever vaccine and the tetravalent dengue vaccine are subject to concomitant administration.

This invention also relates to a combined vaccine composition comprising a yellow fever vaccine and a tetravalent dengue vaccine which comprises a live attenuated dengue virus of each of serotypes 1 to 4 for use in a method of inducing a protective immune response against yellow fever in a human subject, wherein said method comprises administering the said combined vaccine to said human subject.

As it shall be readily understood form the whole disclosure herein, the said combined vaccine is used only once in a method for inducing a protective immunity of a human subject against both yellow fever and dengue. Typically, the combined vaccine composition is used for the first injection, i.e. the step of concomitant administration, in the vaccination schedule, which is followed by one or two further administrations of a tetravalent dengue vaccine which comprises a live attenuated dengue virus of each of serotypes 1 to 4, in a time schedule that is specified elsewhere in the present specification.

The exact quantity of a live attenuated dengue virus or a live attenuated chimeric dengue virus of the present invention to be administered may vary according to the age and the weight of the human subject being vaccinated, the frequency of administration as well as the other ingredients in the composition. Generally, the quantity of a live attenuated dengue virus (e.g. VDV1 or VDV2) comprised in a dose of a vaccine composition as used in a method as described herein lies within a range of from about $10^3$ to about $10^6$ $CCID_{50}$, for example within a range of from about $5 \times 10^3$ to about $5 \times 10^5$, for example about $10^4$ $CCID_{50}$. The quantity of a live attenuated chimeric dengue virus (such as a chimeric YF/dengue virus or a Chimerivax® (CYD) virus) comprised in a vaccine composition as used in the method of the present invention lies within a range of about $10^5$ $CCID_{50}$ to about $10^6$ $CCID_{50}$. The quantity of a live attenuated dengue virus or live attenuated chimeric dengue virus of each of serotypes 1 to 4 comprised in a tetravalent dosage form according to the present invention is preferably equal. The term $CCID_{50}$ refers to the quantity of virus infecting 50% of the cell culture. The $CCID_{50}$ assay is a limit dilution assay with statistical titer calculation (Morrison D., et al., J. Infect. Dis. (2010), 201(3): 370-377).

According to a particular embodiment of a yellow fever vaccinal composition, the said vaccinal composition contains an attenuated yellow fever virus of 4.74 $\log_{10}$ plaque forming units (PFU) or more per dosage unit. In some embodiments, the said attenuated yellow fever virus is the yellow fever strain 17D-204. In some embodiments, the yellow fever vaccinal composition is a product marketed under the name YF VAX® by the company Sanofi Pasteur.

The vaccinal compositions of the present invention may also include one or more pharmaceutically acceptable vehicles. The term "vehicle" refers to compounds commonly used in the formulation of pharmaceuticals and vaccines to enhance stability, sterility and deliverability of the active agent. Suitable vehicles and their preparation are described, for example, in Remington's Pharmaceutical Sciences, 16th Edition, A. Osol, Ed., Mack Publishing Co., Easton, Pa. (1980), and Remington's Pharmaceutical Sciences, 19th Edition, A. R. Gennaro, Ed., Mack Publishing Co., Easton, Pa. (1995). When the vaccinal composition is formulated as a solution or suspension, the immunologically active agent is provided in a pharmaceutically acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques including sterile filtration via a 0.2 micron pore filter. The resulting aqueous solutions may be packaged for use. Alternatively, the aqueous solutions may be lyophilized, the lyophilized preparation being reconstituted with a sterile aqueous solution prior to administration.

The vaccinal compositions may optionally contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorption monolaurate, triethanolamine oleate, human serum albumin, essential amino acids, nonessential amino acids, L-arginine hydrochlorate, saccharose, D-trehalose dehydrate, sorbitol, tris (hydroxymethyl) aminomethane and/or urea. In addition, the vaccinal composition may optionally comprise pharmaceutically acceptable additives including, for example, diluents, binders, stabilizers, and preservatives. A preferred example of a stabilizing solution which may be used in the context of the tetravalent live attenuated dengue vaccine as described herein is disclosed in WO 2010/003670.

Unit dosage formulations of the vaccinal compositions of the present invention may be included in a kit of products containing the vaccinal virus in lyophilized form and a solution for reconstitution of the lyophilized product. Recombinant viruses of the present invention may be lyophilized by conventional procedures and reconstituted. Such solutions for reconstitution of the lyophilized vaccinal composition may be aqueous solvents comprising buffers, organic or inorganic salts, and agents to assist in solubilization.

The concomitant administration of the vaccinal compositions of the present invention may be achieved by transcutaneous, subcutaneous, intramuscular or intradermal injection. The vaccinal compositions may be administered using conventional hypodermic syringes or safety syringes such as those commercially available from Becton Dickinson Corporation (Franklin Lakes, N.J., USA) or jet injectors. For intradermal administration, conventional hypodermic syringes may be employed using the Mantoux technique or specialized intradermal delivery devices such as the BD Soluvia™ microinjection system (Becton Dickinson Corporation, Franklin Lakes, N.J., USA), may also be employed.

Preferably a human subject according to the present invention is at least 12 months old. Preferably said human subject is at least 2 years old. Preferably said human subject is at least 5 years old. Preferably said human subject is at least 7 years old. Preferably said human subject is at least 9 years old. Preferably said human subject is at least 12 years old. Preferably said human subject is aged between 12 months and 60 years old. Preferably said human subject is aged between 2 and 60 years old. Preferably said human subject is aged between 6 and 60 years old. Preferably said human subject is aged between 7 and 60 years old. Preferably said human subject is aged between 9 and 60 years old. Preferably said human subject is aged between 9 and 45 years old. Preferably said human subject is aged between 12 and 60 years old. Preferably said human subject is aged between 2 and 16 years old. Preferably said human subject is aged between 5 and 16 years old. Preferably said human subject is aged between 9 and 16 years old. Preferably said human subject is dengue immune and/or said human subject resides in a dengue endemic area. As used herein, a "dengue immune" subject refers to a subject who has been infected by a dengue virus or immunized by a dengue vaccine before administration of the vaccine composition of the present invention, i.e. a serum sample taken from said subject will produce a positive result in a dengue ELISA or $PRNT_{50}$ assay. Dengue endemic areas are well-known to a person of skill in the art and include, according to the present invention, most of the tropics and sub-tropics, for instance any country identified as an endemic country by the WHO. A dengue endemic area may be defined herein as an area in which the population is at least 50% dengue immune or at least 60% dengue immune. More preferably, a dengue endemic area may be defined as an area in which the population is at least 70% dengue immune, at least 80% dengue immune or at least 90% dengue immune. An area can also be defined as dengue-endemic based on vector presence, the co-circulation of multiple serotypes in the area and the sustained transmission of the disease indicated through routine surveillance data. For example, a dengue endemic area may be defined as an area in which the population is dengue immune as described above, wherein the dengue vector is present and wherein there is sustained transmission of the disease, optionally with co-circulation of multiple serotypes.

In one embodiment, the invention relates to a vaccine composition for use in a method for inducing neutralising antibodies against the four serotypes of dengue, e.g. a protective immune response against dengue disease, wherein said method comprises administering to a human subject at least one composition comprising a tetravalent dengue vaccine which comprises a live attenuated dengue antigen of each of serotypes 1 to 4. In other words, said embodiment does not consider any concomitant administration of a tetravalent dengue vaccine with a yellow fever (YF) vaccine. In this embodiment, the invention provides a multi-step dosage regimen. An initial administration of a tetravalent dengue vaccine composition which comprises a live attenuated dengue virus of each of serotypes 1 to 4 is performed at a time T0 and may be enhanced by the administration of a second dose of the tetravalent vaccinal dengue composition of four serotypes at a date approximately 1, 2, 3, 4, 5, 6, 7, 8, or 9 months following T0 (this second administration being administered on a date termed T1). In another embodiment, a third administration of the tetravalent vaccinal dengue composition of four serotypes of dengue may be administered at a date approximately 1, 2, 3, 4, 5, 6, 7, 8, or 9 months following T1 (this third administration being administered on a date termed T2). Preferred three dose regimens include 0-6-12 and 0-2-6 (i.e. a first dose of the tetravalent dengue vaccinal composition at T0, followed by a second dose of the tetravalent dengue vaccinal composition at T1, which is 2 or 6 months after T0 and a third dose of the tetravalent dengue vaccinal composition at T2, which is 6 or 12 months after T0). The most preferred three dose regimens include 0-2-6 (i.e. a first dose of the tetravalent dengue vaccinal composition at T0, followed by a second dose of the tetravalent dengue vaccinal composition at T1, which is 2 months after T0 and a third dose of the tetravalent dengue vaccinal composition at T2, which is 6 months after T0.

In another embodiment, the invention provides a multi-step dosage regimen. An initial co-administration of a tetravalent dengue vaccine composition which comprises a live attenuated dengue virus of each of serotypes 1 to 4 and a yellow fever vaccinal composition is performed at a time T0 and may be enhanced by the administration of a second dose of the tetravalent vaccinal dengue composition of four serotypes at a date approximately 1, 2, 3, 4, 5, 6, 7, 8, or 9 months following T0 (this second administration being administered on a date termed T1). In another embodiment, a third administration of the tetravalent vaccinal dengue composition of four serotypes of dengue may be administered at a date approximately 1, 2, 3, 4, 5, 6, 7, 8, or 9 months following T1 (this third administration being administered on a date termed T2). Preferred two dose regimens include 0-3 and 0-6 (i.e. a first dose of the tetravalent dengue vaccinal composition concomitantly administered with YF vaccine at T0, followed by a second dose of the tetravalent dengue vaccinal composition at T1, which is 3 or 6 months after T0). Preferred three dose regimens (i.e. three-dose dengue vaccination schedules) include 0-6-12 and 0-2-6 (i.e. a first dose of the tetravalent dengue vaccinal composition concomitantly administered with YF vaccine at T0, followed by a second dose of the tetravalent dengue vaccinal composition at T1, which is 2 or 6 months after T0 and a third dose of the tetravalent dengue vaccinal composition at T2, which is 6 or 12 months after T0.

Booster administrations of the tetravalent vaccinal dengue compositions and/or yellow fever vaccine may be administered subsequent to the foregoing dosage regimen to maintain robust immunoprotection in the human. Such booster administrations may occur at time points of approximately 1 year, 2 years, 3 years, 4 years, 5 years, 10 years, or longer after T2.

According to another aspect, this invention has as its object a kit.

The kit according to the invention comprises vaccinal compositions as described in relation to the method described herein. The kit according to the invention therefore comprises a box containing various containers holding the compositions or vaccines and advantageously an explanatory brochure including useful information for administration of the said compositions or vaccines. The term container includes conventional sealed vials and pre-filled syringes. According to one embodiment, this invention therefore relates to a kit for immunization against dengue serotypes 1, 2, 3, and 4, as well as yellow fever virus, comprising a box containing at least (a) a first container holding a yellow fever vaccine, and (b) a second container holding a tetravalent dengue vaccine which comprises a live attenuated dengue virus of each of serotypes 1 to 4. The vaccinal compositions which may be used in the kit according to the invention include the vaccinal compositions described herein in relation to the method according to the invention.

If the vaccinal compositions are provided in lyophilized form, the kit will advantageously comprise at least one additional container holding a solution which can be used to reconstitute a lyophilized vaccinal composition suitable for administration by intradermal, transcutaneous, subcutaneous, or intramuscular administration. Pharmaceutically acceptable diluents and carriers may be used for reconstitution and are described herein.

According to a particular embodiment, the kit according to the invention comprises a tetravalent vaccine comprising $10^5$ to $10^6$ $CCID_{50}$ of Chimerivax™ DEN-1, 2, 3 and 4. The container in which the pharmaceutical formulation is packaged prior to use can comprise a hermetically sealed container enclosing an amount of the lyophilized formulation or a solution containing the formulation suitable for a pharmaceutically effective dose thereof, or multiples of an effective dose. The pharmaceutical formulation is packaged in a sterile container, and the hermetically sealed container is designed to preserve sterility of the pharmaceutical formulation until use.

Optionally, the container can be associated with administration means and or instruction for use. Examples of administration means may include syringes for parenteral administration or delivery systems to facilitate intradermal administration.

Regarding the pharmaceutical dosage forms, the volume of vaccinal composition administered will depend on the method of administration. In the case of subcutaneous injections, the volume is generally between 0.1 and 1.0 ml, preferably approximately 0.5 ml.

This invention is further illustrated by, without in any way being limited to, the examples below.

EXAMPLES

Example 1

Yellow Fever (YF) and Dengue Vaccination with a Three Injection Administration Schedule at M0, After 6 Months (M6) and After 12 Months (M12) in Toddlers A. Materials and Methods
A.1. Study Design and Participants This was a randomized, observer-blind, controlled, multicenter, phase III trial conducted in 792 toddlers in Colombia and Peru between 7 Sep. 2011 and 2 Sep. 2013. The study was conducted in accordance with the ethical principles of the Declaration of Helsinki and the International Conference on the Harmonization-Good Clinical Practice. The study was approved by each study site's institutional review board and local ethics committee, and written informed consent was obtained from all participants' parents/guardians before study entry.

Eligible participants were toddlers aged 12 months (or up to the first day of the 13th month after birth) in good health and who were born at full term (≥37 weeks pregnancy) with a birth weight ≥2.5 kg. The toddlers had to have received all vaccinations in the national immunization schedule, with the exception of the seasonal influenza vaccine. Participants were excluded if they had previous history of yellow Fever (YF) or dengue infection or if they had previous vaccinations against YF (including previous maternal vaccination against YF), measles, mumps, rubella and hepatitis A. Other exclusion criteria included: known or suspected congenital or acquired immunodeficiency; receipt of blood or blood-derived products in the past three months which might interfere with assessment of the immune response; receipt of immunosuppressive therapy such as anti-cancer chemotherapy or radiation therapy within the preceding six weeks, or long-term systemic corticosteroid therapy (for more than two consecutive weeks within the previous three months); seropositivity to human immunodeficiency virus; history of central nervous system disorder or disease, including seizures; thrombocytopenia, bleeding disorders or receipt of anticoagulants in the three weeks preceding inclusion; and known systemic hypersensitivity to any of the components of the vaccines.

Figure 1:
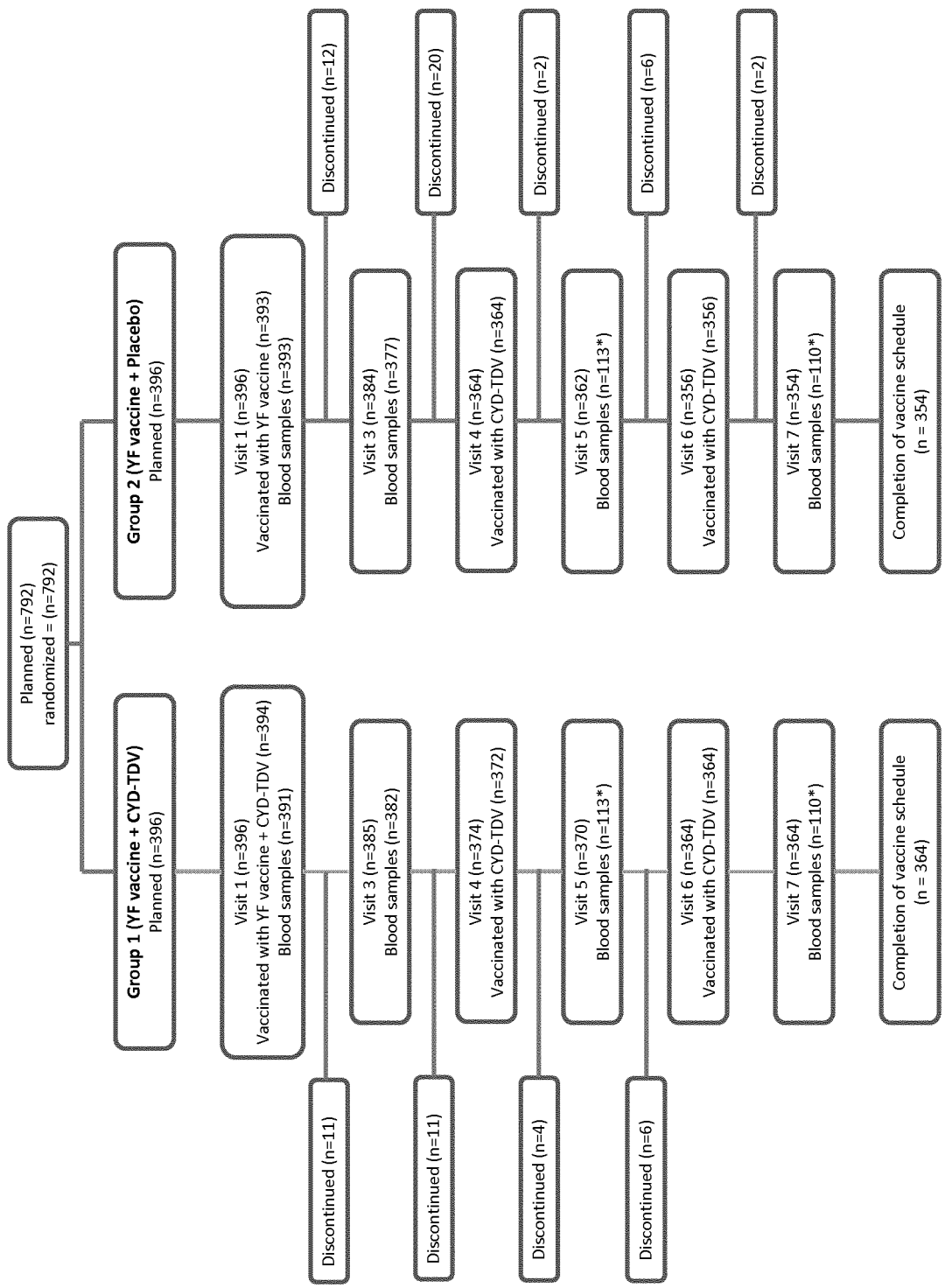
FIG. 1 is a flow chart that depicts the participant vaccination disposition.

A total of 792 participants were enrolled and randomized; 472 (59.6%) in Colombia and 320 (40.4%) in Peru. The flow of participants through the study is shown in FIG. 1. Six (0.8%) participants did not meet at least one inclusion criterion or had at least one exclusion criterion. Four participants, one in Group 1 and three in Group 2, did not complete their vaccination schedule according to the official immunization calendar for Colombia or Peru. One participant from Group 1 had a history of central nervous system disorder or disease, including seizure and a second participant in Group 1 had received one vaccine in the 4 weeks preceding the first trial vaccination.

The two groups were well balanced in terms of baseline characteristics (Table 1).

A.2. Random Assignment and Blinding

An interactive voice recognition system or interactive web response system (IVRS/IWRS) was used to assign participants an enrollment number and for random allocation in a 1:1 ratio to two study groups using permuted block randomization (blocks of 4) stratified by center. Both treatment allocation and dose numbers were randomized, thereby ensuring that dose numbers could not be used to distinguish between treatment groups. A designated, unblinded staff member at each site not involved in data collection or safety assessments (i.e. observer-blind) used the centralized IVRS/IWRS to obtain the product code assigned, reconstituted the vaccine, and administered the assigned vaccine or placebo.

Vaccination and Vaccines

YF vaccine (Stamaril; Sanofi Pasteur S.A., France) was supplied as powder and solvent for suspension for injection. Each 0.5 mL injection of reconstituted vaccine contained 1000 LD50 units of the virus. The solvent consisted of NaCl 0.4%. Live attenuated tetravalent chimeric yellow fever-dengue vaccine CYD-TDV (Sanofi Pasteur S.A., France—the four strains of serotypes 1 to 4 in the vaccine were each constructed using a YF17D genomic backbone in which the YF prM-E sequence was replaced with a prM-E sequence as set out in one of SEQ ID NOs 1-4) was supplied as powder and solvent for suspension for injection. Each 0.5 mL injection of reconstituted vaccine contained 5±1 log 10 cell-culture infectious dose 50% (CCID50) of each attenuated, recombinant dengue serotype 1, 2, 3 and 4 virus. The solvent consisted of NaCl 0.4%. The placebo was 0.5 mL injection of NaCl 0.9%.

Group 1 received the YF vaccine and the first CYD-TDV injection at enrollment (M0), followed by the second and third CYD-TDV injections after 6 (M6) and 12 (M12) months (i.e., at 18 and 24 months of age). Group 2 received the YF vaccine and a placebo at enrollment (M0), followed by the first and second CYD-TDV injection at M6 and M12, respectively.

The YF vaccine, CYD-TDV and placebo vaccines were administered as subcutaneous injections in the deltoid region of the upper arm; at M0 the vaccine(s) or placebo were administered in opposite arms. Toddlers also received the Measles, Mumps, and Rubella (MMR) vaccine and pneumococcal conjugated vaccine in their national immunization schedule one month after the first set of study injections (M1, at 13 to 14 months of age). Since there were slight differences in the official vaccination calendars for other vaccines between the two countries, to offer an equal benefit to all participants in the trial, the following vaccines were also offered to all participants: hepatitis A vaccine one month after the first set of study injections (M1); a pentavalent vaccine for diphtheria, tetanus, acellular pertussis, polio and *Haemophilus influenzae* type b (DTaP-IPV//Hib) one month after the second study injections (M7, at 19 to 20 months of age); and a hepatitis A vaccine one month after the third study injections (M13, at 25 to 26 months of age). No safety or immunogenicity data were recorded for the MMR, pneumococcal conjugated, hepatitis A or DTaP-IPV//Hib vaccines.

A.3. Immunogenicity

All participants provided one blood sample (3 mL) before the first vaccination for assessment of baseline FV immune status (YF and dengue) and one blood sample (3 mL) 28 days after the first set of study injections for assessment of YF neutralizing antibodies titers. In participants who received CYD-TDV injections, blood samples (3 mL) were also obtained 28 days after the second and third set of study injections for assessment of dengue neutralizing antibody titers. YF and dengue neutralizing antibody titers were determined using a 50% plaque reduction neutralization test ($PRNT_{50}$) with constant challenge doses of YF virus and parental dengue virus strains of CYD-TDV constructs, respectively, as described in Example 2. Both assays had a lower limit of quantitation titer of 10 (l/dil). A threshold titer of 10 (l/dil) was used to assess the immunogenic response to both vaccines; for YF, titers above this threshold were considered as seroconverted.

A.4. Safety and Reactogenicity

Participants were kept under observation for 30 minutes after each trial vaccination to assess the occurrence of any immediate adverse events/reactions. Parents/guardians were provided with rulers, digital thermometers, and diary cards to record daily temperature and any solicited local injection site reactions (tenderness, redness, and swelling) during the 7-day period following each study vaccination, and systemic symptoms (fever, vomiting, abnormal crying, drowsiness, loss of appetite and irritability) for 14 days. Parents/guardians also recorded the use of medication to alleviate symptoms or action taken (e.g. contact with healthcare provider for prescription or hospitalization). Parents/guardians also graded the intensity of subjective solicited reactions and unsolicited adverse reactions using a three point grading scale of increasing severity (Grades 1-3) previously described (Tregnaghi et al., Pediatr. Infect. Dis. J., (2012), 31(1): e24-30). Measurable adverse reactions of erythema, swelling and fever were also graded using the same scale of increasing severity during statistical analysis as previously described (Poo et al., Pediatr. Infect. Dis. J., (2011), 30: e9-e17). Occurrence of unsolicited (i.e., spontaneously reported) non-serious adverse events were recorded for up to 28 days following each injection. The study investigators assessed the causal relationship of each unsolicited systematic adverse event to vaccination as either unrelated or related. Serious adverse events were recorded throughout the trial and up to six months after the last vaccination, and assessed for causal relationship to vaccination by the study investigators.

Adverse events of special interest monitored were hypersensitivity/allergic reactions within seven days of injection, viscerotropic or neurotropic disease reported as a serious adverse event within 30 days after the injection, and suspected serious dengue disease at any time during the study. Suspected serious dengue disease was defined as an acute febrile illness (temperature ≥38° C.) on at least two consecutive days and with sign(s) of severity requiring hospitalization. In such cases, two blood samples were collected: an acute sample (0-5 days after fever onset) and a convalescent sample (7-14 days after the acute sample). Virological confirmation of dengue was defined as detection of wild type dengue virus by NS1 antigen enzyme-linked immunosorbent assay and/or amplified genomic sequences by reverse transcription polymerase chain reaction (RT-PCR).

A.5. Sample Size Determination and Statistical Analyses

The primary objective of this study was to test the non-inferiority of the antibody response (in terms of seroconversion rates) against YF in toddlers receiving one injection of YF vaccine administered concomitantly with the first injection of CYD-TDV compared to those receiving the YF vaccine administered concomitantly with placebo, assuming a non-inferiority delta margin (clinically significant difference) of 10%. Based on simulations using the Wilson score method (without continuity correction) and, assuming a 15% drop out rate, an alpha=2.5% (one-sided), a seroconversion rate of 80% (Stefano et al., Vaccine (1999), 17(9-10): 1042-1046) and a 90% power, then a total of 792 participants (396 per group) would need to be enrolled (336 per group evaluable).

A non-inferiority test was performed using the 95% two-sided CI of the difference in the YF seroconversion rates 28 days after vaccination between the two groups in participants who were FV seronegative at baseline. The 95% CI was calculated based on the Wilson score method without continuity correction as described by Newcombe (Stat. Med., (1998), 17(8): 873-890. Non-inferiority was demonstrated if the lower limit of the two-sided 95% CI was greater than −10%.

The primary immunogenicity analyses were performed on the per-protocol set defined as those participants who met all protocol-specified inclusion criteria and without any protocol-specified exclusion criteria, received the YF vaccine injection and the first CYD-TDV or placebo injection, provided a pre and post-injection serum sample within the specified times and with valid test results, and who were Flavivirus seronegative at baseline. The intent-to-treat set (defined as participants who received the YF vaccine injection along with CYD-TDV or placebo injection, provided post-injection blood sample with valid test results) was used for the secondary YF immunogenicity analyses. For the dengue immunogenicity analyses, the intent-to-treat set was defined as participants who received at least one CYD-TDV injection, provided post-injection blood sample with valid test results. The safety analysis set consisted of all participants who received at least one injection of YF vaccine, CYD-TDV or placebo, analyzed according to the treatment received at the first injection. The incidences of adverse events were calculated along with the 95% CIs by allocated group.

Results

Example 1-1

Safety of the Combined Yellow Fever and Dengue Vaccination

Figure 2:
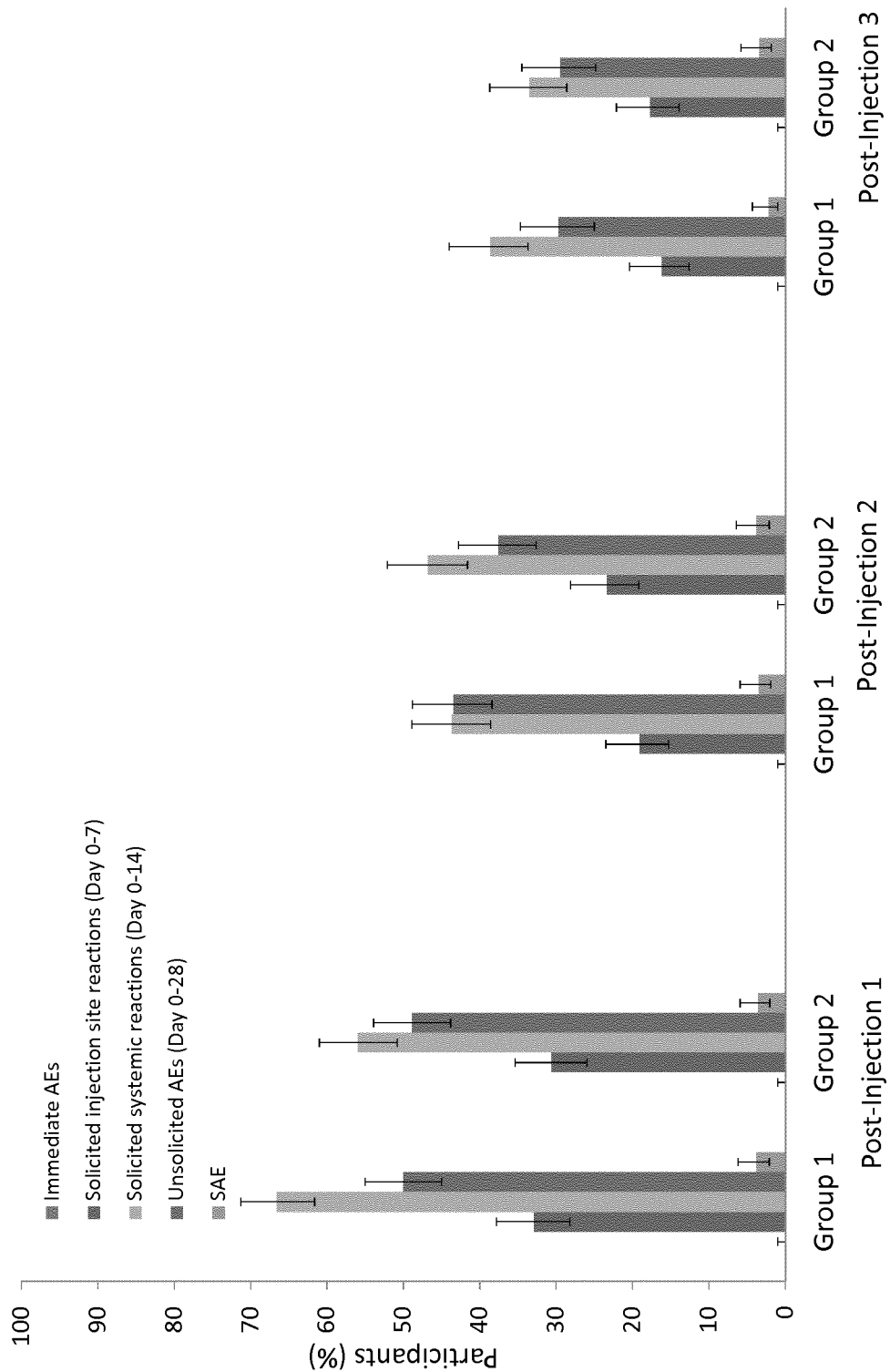
FIG. 2 illustrates the comparative safety results between vaccination against dengue alone or in combination with vaccination against yellow fever.

There were no immediate unsolicited adverse events or reactions. A summary of the safety overview is presented in FIG. 2. There were no safety concerns following concomitant administration of YF vaccine with CYD-TDV during the study period, however, fever was more frequent following concomitant administration of YF vaccine with CYD-TDV compared with YF vaccine and placebo (26.7% versus 16.5%; p<0.001). Most solicited reactions were of grade 1 intensity occurring within 3 days after any injection. Details of injection site and systemic reactions are summarized in Table 2.

A total of eight participants experienced adverse events that led to study discontinuation: three in Group 1 and five in Group 2. Overall, 73 participants experienced 83 serious adverse events at any time during the study with no differences between study groups: 35 (8.9%) in Group 1 and 38 (9.7%) in Group 2 reported 41 and 42 serious adverse events, respectively. All serious adverse events (except one, see below) were considered as not-related to the study treatments by both the study investigators and sponsor. Of these serious adverse events, five led to study discontinuation: two in Group 1 (both febrile seizures with one occurring one day after the first study injections, which was considered possibly related to study injections by the study sponsor, and the other occurred 84 days after the first study injections); and three in Group 2 (viral meningitis [diagnosis based upon clinical features and cerebrospinal fluid leak characteristics] 27 days after the first study injection, febrile convulsion episode 97 days after the first CYD-TDV injection, and a traumatic brain injury caused by a fall 23 days after the second CYD-TDV injection).

Few participants reported non-serious adverse events of special interest: 11 (2.8%) in Group 1 and 7 (1.8%) in Group 2. All but one of these adverse events of special interest (one episode of urticaria in Group 1 which started on the day of injection, lasted for 6 days and spontaneously resolved) were considered as not related to the study injections. There was one virologically-confirmed (NS1 antigen and PCR-RT screening both positive) hospitalized dengue case (serotype not identified) reported in Group 2 during the study (20 days after the third study injection).

Example 1-2

Immune Response to the Combined Yellow Fever and Dengue Vaccination

Yellow Fever Vaccine Immune Response

YF seroconversion rates 28 days after the first study injections in the per-protocol analysis are summarized (Table 3)—administration of the YF vaccine concomitantly with CYD-TDV was non-inferior to the immune response following concomitant administration of YF and placebo in FV seronegative toddlers. The difference in seroconversion rates ($PRNT_{50} \geq 1:10$) between the two groups was 0.33% (95% CI—0.98; 1.87). A similar result was also observed in the intent-to-treat cohort (Table 3).

$Log_{10}$ YF antibody titers before and 28 days after the first study injections are illustrated in box plots for both groups in the intent-to-treat set (FIG. 3).

CYD-TDV Immune Response

The proportion of dengue immune subjects at baseline was low and similar in both groups, with 23 subjects (6.0%) in Group 1 and 22 subjects (5.8%) in Group 2. GMTs of the antibodies against the four dengue serotypes pre-injection and after the second and third set of study injections for the intent-to-treat set (Dengue Immunogenicity) are summarized in FIG. 4. For dengue serotype 1, participants who received 3 CYD-TDV injections (Group 1) had a higher GMT than those who received only 2 injections (Group 2) (p<0.001). GMTs for dengue serotype 2, 3 and 4 were similar in participants in Group 1 who received 3 dengue injections and Group 2 following only 2 dengue injections (p>0.05).

After the second CYD-TDV injection, the percentage of participants with dengue titres above 10 (l/dil) were 91.2-100% and 97.2-100% across the four serotypes in Group 1 and Group 2, respectively. After the third CYD-TDV injection in Group 1 the percentage of participants with dengue titres above 10 (l/dil) were 97.3-100% across the four serotypes.

Conclusion

The concomitant administration of YF vaccine with CYD-TDV results in a good YF antibody response, with no clinically relevant impact on the immunogenicity or safety profile of the YF vaccine. Both vaccines may therefore be administered concomitantly.

Safety Follow-Up

Two years after the completion of the trial, a safety follow-up at the Colombia site was carried out to identify cases of severe dengue in trial subjects. 427 of the 467 subjects who had participated in the trial were found and contacted. Only one subject had presented with a case of dengue (not severe, not hospitalized) and that subject recovered with routine supportive treatment.

TABLE 1

Baseline characteristics of the participants (Intent-to-treat set)

| | Group 1 (N = 381) | Group 2 (N = 377) |
|---|---|---|
| Males, n (%) | 191 (50.1) | 181 (48.0) |
| Mean age ± SD (months) | 12.2 ± 0.25 | 12.2 ± 0.25 |
| Mean BMI ± SD (kg/m$^2$) | 17.3 ± 1.63 | 17.4 ± 3.84 |
| Ethnic origin, n (%) | | |
| Black | 35 (9.2) | 30 (8.0) |
| Hispanic | 346 (90.8) | 347 (92.0) |
| Flavivirus seropositive (n, %) | 54 (14.2) | 53 (14.1) |
| Yellow fever seropositive (n, %) | 34 (8.9) | 34 (9.0) |
| Dengue seropositive (n, %) | 23 (6.0) | 22 (5.8) |

TABLE 2

Overall summary of safety and reactogenicity following concomitant administration of yellow fever and dengue vaccines (Group 1) or yellow fever and placebo (Group 2) after 1st, 2nd and 3rd injections (Safety Analysis Set).

|  |  | Post-injection 1 | | Post-injection 2 |
|---|---|---|---|---|
|  |  | Group 1 (N = 394) % (95 CI) | Group 2 (N = 393) % (95 CI) | Group 1 (N = 372) % (95 CI) |
| Any solicited reaction |  | 71.5 (66.7; 76.0) | 63.5 (58.4; 68.3) | 49.6 (44.4; 54.8) |
| Solicited injection site reaction | Any | 32.9 (28.2; 37.8) | 30.6 (26.0; 35.4) | 19.1 (15.3; 23.5) |
|  | Grade 3 | 0.03 (0.0, 1.4) | 0.03 (0.0, 1.4) | 0 (0.0; 1.0) |
| Tenderness YF | Any | 25.4 (21.1, 30.0) | 17.6 (13.9, 21.8) | NA |
| Tenderness CYD-TDV | Any | 24.9 (20.6, 29.5) | NA | 17.0 (13.3, 21.2) |
| Tenderness Placebo | Any | NA | 19.7 (15.8, 24.0) | NA |
| Erythema YF | Any | 8.3 (5.7, 11.5) | 9.8 (7.1, 13.3) | NA |
| Erythema CYD-TDV | Any | 8.8 (6.2, 12.1) | NA | 5.1 (3.1, 7.9) |
| Erythema Placebo | Any | NA | 10.9 (8.0, 14.4) | NA |
| Swelling YF | Any | 4.7 (2.8, 7.3) | 4.4 (2.6, 7.0) | NA |
| Swelling CYD-TDV | Any | 4.7 (2.8, 7.3) | NA | 2.7 (1.3, 4.9) |
| Swelling Placebo | Any | NA | 4.9 (3.0, 7.6) | NA |
| Solicited systemic reaction | Any | 66.6 (61.6; 71.3) | 56.0 (50.8; 61.0) | 43.7 (38.6; 48.9) |
|  | Grade 3 | 6.2 (4.0, 0.1) | 4.9 (3.0, 7.6) | 0.8 (0.2; 2.3) |
| Fever[a] | Any | 26.7 (22.3, 31.5) | 16.5 (12.9, 20.7) | 21.2 (17.1, 25.8) |
|  | Grade 3 | 1.1 (0.3, 2.7) | 0.3 (0.0, 1.5) | 0.0 (0.0, 1.0) |
| Vomiting | Any | 16.1 (12.5, 20.1) | 17.1 (13.5, 21.2) | 12.4 (9.2, 16.2) |
|  | Grade 3 | 0.5 (0.1, 1.9) | 1.0 (0.3, 2.6) | 0.5 (0.1, 1.9) |
| Crying abnormal | Any | 32.9 (28.2, 37.8) | 32.1 (27.5, 37.0) | 19.7 (15.8, 24.1) |
|  | Grade 3 | 0.5 (0.1, 1.9) | 1.3 (0.4, 3.0) | 0.0 (0.0, 1.0) |
| Drowsiness | Any | 24.4 (20.2, 29.0) | 22.0 (18.0, 26.5) | 12.7 (9.5, 16.5) |
|  | Grade 3 | 0.5 (0.1, 1.9) | 0.0 (0.0, 1.0) | 0.0 (0.0, 1.0) |
| Appetite lost | Any | 39.6 (34.7, 44.7) | 33.7 (29.0, 38.6) | 27.0 (22.5, 31.8) |
|  | Grade 3 | 4.4 (2.6, 7.0) | 3.1 (1.6, 5.4) | 0.3 (0.0, 1.5) |
| Irritability | Any | 38.6 (33.7, 43.7) | 34.7 (30.0, 39.7) | 17.3 (13.5, 21.5) |
|  | Grade 3 | 1.6 (0.6, 3.4) | 1.3 (0.4, 3.0) | 0.0 (0.0, 1.0) |
| Unsolicited AE (Days 0-28) |  | 50 (45.0; 55.0) | 48.9 (43.8; 53.9) | 43.5 (38.4; 48.8) |
| Unsolicited AR (Days 0-28) |  | 0.3 (0.0; 1.4) | 0.3 (0.0; 1.4) | 0.3 (0.0, 1.5) |
| SAE |  | 3.8 (2.1; 6.2)[a] | 3.6 (2.0; 5.9)[a] | 3.5 (1.9, 5.9)[b] |

|  |  | Post-injection 2 | Post-injection 3 | |
|---|---|---|---|---|
|  |  | Group 2 (N = 364) % (95 CI) | Group 1 (N = 364) % (95 CI) | Group 2 (N = 356) % (95 CI) |
| Any solicited reaction |  | 52.3 (47.1; 57.6) | 43.1 (38.0; 48.4) | 39.2 (34.0; 44.4) |
| Solicited injection site reaction | Any | 23.4 (19.2; 28.1) | 16.2 (12.6; 20.4) | 17.7 (13.9; 22.1) |
|  | Grade 3 | 0 (0.0; 1.0) | 0.3 (0.0; 1.5) | 0 (0.0; 1.0) |
| Tenderness YF | Any | NA | NA | NA |
| Tenderness CYD-TDV | Any | 20.4 (16.4, 24.9) | 14.6 (11.1, 18.6) | 16.3 (12.6, 20.6) |
| Tenderness Placebo | Any | NA | NA | NA |
| Erythema YF | Any | NA | NA | NA |
| Erythema CYD-TDV | Any | 8.0 (5.4, 11.3) | 3.6 (1.9, 6.0) | 4.2 (2.4, 6.9) |
| Erythema Placebo | Any | NA | NA | NA |
| Swelling YF | Any | NA | NA | NA |
| Swelling CYD-TDV | Any | 8.0 (5.4, 11.3) | 1.6 (0.6, 3.6) | 2.8 (1.4, 5.1) |
| Swelling Placebo | Any | NA | NA | NA |
| Solicited systemic reaction | Any | 46.8 (41.6; 52.1) | 38.7 (33.3; 44.0) | 33.5 (28.6; 38.7) |
|  | Grade 3 | 1.1 (0.3; 2.8) | 0.5 (0.1; 2.0) | 1.4 (0.5; 3.3) |
| Fever[a] | Any | 22.2 (17.9, 26.9) | 20.3 (16.2, 25.0) | 17.8 (13.8, 22.3) |
|  | Grade 3 | 0.3 (0.0, 1.6) | 0.3 (0.0, 1.6) | 0.3 (0.0, 1.7) |
| Vomiting | Any | 8.8 (6.1, 12.2) | 7.4 (4.9, 10.6) | 7.3 (4.8, 10.5) |
|  | Grade 3 | 0.6 (0.1, 2.0) | 0.0 (1.5) | 0.6 (0.1, 2.0) |
| Crying abnormal | Any | 21.8 (17.6, 26.4) | 15.1 (11.6, 19.2) | 14.6 (11.1, 18.8) |
|  | Grade 3 | 0.0 (0.0, 1.0) | 0.0 (0.0, 1.0) | 0.0 (0.0, 1.0) |
| Drowsiness | Any | 16.5 (12.9, 20.8) | 11.3 (8.2, 15.0) | 10.7 (7.7, 14.4) |
|  | Grade 3 | 0.0 (0.0, 1.0) | 0.0 (0.0, 1.0) | 0.0 (0.0, 1.0) |
| Appetite lost | Any | 23.1 (18.9, 27.8) | 19.8 (15.8, 24.2) | 18.6 (14.7, 23.0) |
|  | Grade 3 | 0.3 (0.0, 1.5) | 0.0 (0.0, 1.0) | 0.3 (0.0, 1.6) |
| Irritability | Any | 22.3 (18.1, 27.0) | 14.3 (10.9, 18.3) | 16.1 (12.4, 20.3) |
|  | Grade 3 | 0.0 (0.0, 1.0) | 0.0 (0.0, 1.0) | 0.3 (0.0, 1.6) |
| Unsolicited AE (Days 0-28) |  | 37.6 (32.6, 42.8) | 29.7 (25.0, 34.7) | 29.5 (24.8, 34.5) |
| Unsolicited AR (Days 0-28) |  | 0.3 (0.0, 1.5) | 0.3 (0.0, 1.5) | 0.0 (0.0, 1.0) |
| SAE |  | 3.8 (2.1, 6.4)[b] | 2.2 (1.0, 4.3)[c] | 3.4 (1.8, 5.8)[c] |

TABLE 3

Non-inferiority of yellow fever seroconversion rate at 28 days post 1st injections

| | Group 1 | | Group 2 | | Difference | | |
|---|---|---|---|---|---|---|---|
| | n/M | (%) | n/M | (%) | (%) | 95% CI for difference | Non-inferiority |
| Per protocol analysis set | 296/296 | 100 | 298/299 | 99.7 | 0.334 | (−0.976, 1.87) | Yes |
| Intent-to-treat set | 373/378 | 98.7 | 375/376 | 99.7 | −1.06 | (−2.81, 0.383) | Yes | n, number of subjects meeting the specified criteria
M, number of subjects available for the endpoint
Seroconversion is defined as yellow fever antibodies ≥10 (1/dil) in flavivirus seronegative participants
Group 1: Yellow fever vaccine + CYD dengue vaccine at first injections
Group 2: Yellow fever vaccine + placebo at first injections
Non-inferiority is demonstrated (Yes) if the lower limit of the 95% CI is greater than −10
95% CI for the difference is based on the Wilson score method without continuity correction Example 2

Yellow Fever (YF) and Dengue Vaccination with an Administration Schedule in Three Injections at M00, After 2 Months (M02) and After 6 Months (M06) in Adults Aged 18 to 45 Years Materials and Methods A.1. Study Design and Participants This was a Phase II, randomized, open-label, multicenter study conducted in 390 healthy adults aged ≥18 years to ≤45 years in the US between 6 Dec. 2011 and 27 Sep. 2013.

Screening Criteria

There were no screening criteria.

Inclusion Criteria

A potential subject had to meet all of the following criteria to be considered for trial enrollment:

1) Aged ≥18 to ≤45 years on the day of inclusion ("18 to 45 years" means from the day of the 18th birthday to the day before the (45+1)th birthday), 2) Informed consent form has been signed and dated, 3) Able to attend all scheduled visits and to comply with all trial procedures, 4) For subjects classified as YF+ to be included in Groups 1 and 2, previous vaccination (3 months to 10 years) with YF vaccine confirmed by acceptable documentation.

Exclusion Criteria

A potential subject meeting any of the following criteria was ineligible for trial enrollment:

1) Subject is pregnant, or lactating, or of childbearing potential (to be considered of non-childbearing potential, a female must be post-menopausal for at least 1 year, surgically sterile, or using an effective method of contraception or abstinence from at least 4 weeks prior to the first vaccination and until at least 4 weeks after the last vaccination), 2) Participation in the 4 weeks preceding the first trial vaccination, or planned participation during the present trial period, in another clinical trial investigating a vaccine, drug, medical device, or medical procedure, 3) Receipt of any vaccine in the 4 weeks preceding the first trial vaccination or planned receipt of any vaccine in the 4 weeks following each trial vaccination, 4) For all subjects classified as YF−, any previous vaccination against FV diseases (including Japanese Encephalitis, tick-borne encephalitis, and YF), 5) For subjects classified as YF+, previous vaccination against FV diseases except YF (including Japanese Encephalitis and tick-borne encephalitis), 6) For all subjects, any FV vaccination planned during the trial period outside the study protocol, 7) Receipt of immune globulins, blood or blood-derived products in the past 3 months, 8) Known or suspected congenital or acquired immunodeficiency; or receipt of immunosuppressive therapy such as anti-cancer chemotherapy or radiation therapy within the preceding 6 months; or long-term systemic corticosteroid therapy (prednisone or equivalent for more than 2 consecutive weeks within the past 3 months), 9) Self-reported seropositivity for human immunodeficiency virus (HIV), hepatitis B, or hepatitis C, 10) Self-reported history of FV infection (e.g., JE, Dengue, YF, West Nile), confirmed either clinically or serologically, 11) Known systemic hypersensitivity to any of the vaccine components, or history of a life-threatening reaction to the vaccine(s) used in the trial or to a vaccine containing any of the same substances, including dry natural latexa, 12) Deprived of freedom by an administrative or court order, or in an emergency setting, or hospitalized involuntarily, 13) Current alcohol abuse or drug addiction, 14) Chronic illness that, in the opinion of the investigator, is at a stage where it might interfere with trial conduct or completion, 15) Identified as an employee of the Investigator or study center, with direct involvement in the proposed study or other studies under the direction of that Investigator or study center, as well as family members (i.e., immediate, husband, wife and their children, adopted or natural) of the employee or the Investigator, 16) Moderate or severe acute illness/infection (according to investigator judgment) on the day of vaccination or febrile illness (temperature ≥38.0° C. [≥100.4° F.]). A prospective subject should not be included in the study until the condition has resolved or the febrile event has subsided, 17) Previous residence (>12 months) in, or travel in the last 30 days to FV endemic regions, 18) History of thymic pathology (thymoma), thymectomy, or myasthenia.

A.2. Random Assignment

CYD dengue vaccine and/or YF vaccine was to be administered to subjects in the 3 vaccination groups as follows in Table 4:

TABLE 4

| Vaccination Group | 00 | 02 | 06 | 12 | Number of subjects per Group |
|---|---|---|---|---|---|
| 1 | CYD Dengue Vaccine | — | CYD Dengue Vaccine | CYD Dengue Vaccine | 120* |
| 2 | CYD Dengue Vaccine | CYD Dengue Vaccine | CYD Dengue Vaccine | — | 120* |
| 3 | YF vaccine and CYD Dengue Vaccine | CYD Dengue Vaccine | CYD Dengue Vaccine | — | 120 |
| 4 | YF vaccine | — | — | — | 30 |

*Included subjects who were YF+ or YF− at baseline

Vaccination and Vaccines

As displayed in Table 4 above:
subjects in Group 1 were to receive 3 doses of CYD dengue vaccine, administered at 0, 6, and 12 months,
subjects in Groups 2 and 3 were to receive 3 doses of CYD dengue vaccine, administered 0, 2, and 6 months. Subjects in Group 3 were to additionally receive YF vaccine concomitantly with CYD dengue vaccine at M00,
subjects in Group 4 were to receive YF vaccine only at M00.

CYD Dengue Vaccine

Vaccine: CYD dengue vaccine (live, attenuated, tetravalent chimeric yellow fever-dengue vaccine, Sanofi Pasteur S.A., France). The four strains of serotypes 1 to 4 in the vaccine were each constructed using a YF17D genomic backbone into which the YF prM-E sequence was replaced with a prM-E sequence as set out in one of SEQ ID NOs 1-4.

Form: Powder and solvent for suspension for injection,
Dose: 0.5 mL of the reconstituted vaccine,
Route: Subcutaneous (SC).
Composition:
Each 0.5 mL dose of reconstituted vaccine contains the following components:
5±1 log 10 cell culture infectious dose 50% (CCID50) of each live, attenuated, recombinant dengue serotype 1, 2, 3, 4 virus,
Excipients: essential amino acids, non-essential amino acids, L-arginine chlorhydrate, saccharose, D-trehalose dihydrate, D-sorbitol, tris (hydroxymethyl) aminomethane, and urea,
Solvent: NaCl 0.4%.
Preparation and Administration:
Sanofi Pasteur's CYD dengue vaccine consists of a powder and solvent for suspension for injection and must be stored between +2° C. and +8° C. The vaccine was to be removed from the refrigerator, reconstituted with the solvent supplied for this purpose, and used immediately after reconstitution. The vaccine was to be administered SC in the deltoid region of the upper arm in a volume of 0.5 mL.

Yellow Fever Vaccine

YF-VAX® vaccine is a licensed product, manufactured by Sanofi Pasteur Inc. Swiftwater, Pa. 18370, USA.
Composition:
YF-VAX® vaccine is prepared by culturing the 17D-204 strain of YF virus in living avian leucosis virus-free chicken embryos. The vaccine contains sorbitol and gelatin as a stabilizer, is lyophilized, and is hermetically sealed under nitrogen. No preservative is added. YF-VAX® is formulated to contain not less than 4.74 log 10 plaque forming units per 0.5 mL dose throughout the life of the product. YF-VAX® vaccine is a slight pink-brown suspension after reconstitution. The diluent used with the vaccine is a sodium chloride solution.

Preparation and Administration:
The vaccine was to be reconstituted immediately before use with the sterile diluent provided (Sodium Chloride Injection USP—contains no preservative). As a licensed vaccine, a 0.5 mL dose of YF-VAX® was to be administered on one occasion.

A.3. Immunogenicity

Dengue Neutralizing Ab Levels

Dengue neutralizing Ab levels were measured by $PRNT_{50}$ at Sanofi Pasteur GCI, Swiftwater, USA (Timiryasova T M, Am. J. Trop. Med. Hyg. 2013 May; 88(5):962-70).

Method: Serial, 2-fold dilutions of serum to be tested (previously heat-inactivated) were mixed with a constant challenge-dose of each dengue virus serotype dengue-1, -2, -3 or -4 (expressed as plaque-forming units [PFU]/mL). The mixtures were inoculated into wells of a microplate with confluent Vero cell monolayers. After adsorption, cell monolayers were incubated for a few days.

The presence of dengue virus infected cells was indicated by formation of plaques. A reduction in virus infectivity due to neutralization by Ab present in serum samples was detected. The reported value (end point neutralization titer) represented the highest dilution of serum at which ≥50% of dengue challenge virus (in plaque counts) was neutralized when compared to the mean viral plaque count in the negative control wells which represented the 100% virus load. The end point neutralization titers were presented as continuous values. The lower level of quantitation (LLOQ) of the assay was 10 (l/dilution [dil]).

YF Neutralizing Ab Levels

YF neutralizing Ab levels were measured by $PRNT_{50}$ by GCI outsourced laboratory (Focus Diagnostics Inc., Cypress, Calif., USA). YF virus neutralizing Ab measurements were assessed by $PRNT_{50}$. Briefly, serial 2-fold dilutions of serum to be tested (previously heat-inactivated) were mixed with a constant challenge dose of the YF vaccinal strain 17D (expressed as PFU/mL). The mixtures were inoculated in duplicate into wells of a plate of confluent Vero cells. After adsorption, cell monolayers were overlaid, incubated for few days, and then stained. Neutralizing Ab titer was calculated and expressed as the reciprocal dilution reducing the mean plaque count by 50% when compared to the mean viral plaque count in the negative control wells which represented the 100% virus load. The end point neutralization titers were presented as discontinuous values. The LLOQ of the assay was 10 (l/dil). The $PRNT_{80}$ method is the same as the $PRNT_{50}$ method described above, except that neutralizing Ab titer was calculated and expressed as the reciprocal dilution reducing the mean plaque count by 80% when compared to the mean viral plaque count in the negative control wells. No new testing was performed for this re-calculation.

Results

Dengue Immune Response in Groups 1 and 2

The considered objective was to describe the humoral immune response to each of the 4 parental dengue virus serotypes at baseline and 28 days after CYD dengue vaccine Dose 3 in Group 1 (M13) and Group 2 (M07).

The table 5 hereinafter presents the GMTs and the GMTRs of Ab against each serotype of dengue in the Full Analysis Set (FAS).

TABLE 5

| Component | Timepoint/Ratio | Group 1 (N = 117) | | | Group 2 (N = 119) | | |
|---|---|---|---|---|---|---|---|
| | | M | GM | (95% CI) | M | GM | (95% CI) |
| Serotype 1 | Pre-Inj 1 | 117 | 5.38 | (4.85; 5.96) | 119 | 5.13 | (4.98; 5.28) |
| | Post-Inj 3 | 93 | 14.8 | (11.3; 19.4) | 108 | 15.9 | (12.6; 20.0) |
| | 6 months Post-Inj 3 | 88 | 13.3 | (10.2; 17.4) | 104 | 9.01 | (7.54; 10.8) |
| | Post-Inj 3/Pre-Inj 1 | 93 | 1.42 | (1.12; 1.79) | 108 | 1.58 | (1.26; 1.98) |
| | 6 months Post-Inj 3/Post-Inj 3 | 86 | 0.597 | (0.495; 0.720) | 104 | 0.440 | (0.364; 0.532) |
| Serotype 2 | Pre-Inj 1 | 117 | 5.19 | (4.82; 5.58) | 119 | 5.22 | (4.96; 5.50) |
| | Post-Inj 3 | 94 | 51.2 | (38.2; 68.6) | 108 | 59.9 | (45.8; 78.4) |
| | 6 months Post-Inj 3 | 88 | 45.6 | (31.6; 65.6) | 104 | 38.7 | (29.5; 50.8) |
| | Post-Inj 3/Pre-Inj 1 | 94 | 4.93 | (3.71; 6.55) | 108 | 5.91 | (4.52; 7.73) |
| | 6 months Post-Inj 3/Post-Inj 3 | 87 | 0.762 | (0.591; 0.982) | 104 | 0.596 | (0.488; 0.727) |
| Serotype 3 | Pre-Inj 1 | 117 | 5.32 | (4.94; 5.73) | 119 | 5.28 | (5.03; 5.55) |
| | Post-Inj 3 | 94 | 45.7 | (35.0; 59.8) | 107 | 59.3 | (47.0; 74.7) |
| | 6 months Post-Inj 3 | 88 | 30.2 | (22.8; 40.2) | 104 | 34.5 | (27.5; 43.3) |
| | Post-Inj 3/Pre-Inj 1 | 94 | 4.38 | (3.38; 5.68) | 107 | 5.79 | (4.61; 7.26) |
| | 6 months Post-Inj 3/Post-Inj 3 | 87 | 0.552 | (0.462; 0.661) | 103 | 0.561 | (0.465; 0.678) |
| Serotype 4 | Pre-Inj 1 | 117 | 5.78 | (5.16; 6.48) | 119 | 5.11 | (4.90; 5.33) |
| | Post-Inj 3 | 94 | 66.8 | (50.9; 87.8) | 107 | 83.1 | (61.4; 112) |
| | 6 months Post-Inj 3 | 88 | 74.8 | (54.9; 102) | 104 | 41.7 | (31.2; 55.9) |
| | Post-Inj 3/Pre-Inj 1 | 94 | 6.02 | (4.61; 7.87) | 107 | 8.17 | (6.04; 11.0) |
| | 6 months Post-Inj 3/Post-Inj 3 | 87 | 0.988 | (0.834; 1.17) | 103 | 0.469 | (0.404; 0.544) |

N: number of subjects analyzed according to the Full Analysis Set
M: number of subjects with available data for the endpoint At Baseline Baseline GMTs were low and similar in both treatment groups and for each serotype: GMTs ranged from 5.11 (l/dil) to 5.78 (l/dil).

Post-Injection 3 (M13 for Group 1 and M07 for Group 2

Serotype 1: the GMTs for serotype 1 increased 28 days after the third dengue injection compared to baseline and were similar in Groups 1 and 2 (14.8 [l/dil] and 15.9 [l/dil], in Groups 1 and 2, respectively).

Serotype 2: the GMTs for serotype 2 increased 28 days after the third dengue injection compared to baseline and were similar in Groups 1 and 2 (51.2 [l/dil] and 59.9 [l/dil], in Groups 1 and 2, respectively).

Serotype 3: the GMTs for serotype 3 increased 28 days after the third dengue injection compared to baseline and were similar in Groups 1 and 2 (45.7 [l/dil] and 59.3 [l/dil], in Groups 1 and 2, respectively).

Serotype 4: the GMTs for serotype 4 increased 28 days after the third dengue injection compared to baseline and were similar in Groups 1 and 2 (66.8 [l/dil] and 83.1 [l/dil], in Groups 1 and 2, respectively).

Whatever the group, levels of GMTs that were reached post-dose 3 were the lowest for serotype 1 and the highest for serotype 4; the levels of GMTs for serotypes 2 and 3 were similar.

At Baseline

Overall, the number and percentage of seropositive subjects at baseline was low and similar across serotypes for both groups: the percentage of seropositive subjects ranged from 0.8% to 6.8%.

Post-Injection 3 (M13 for Group 1 and M07 for Group 2)

In both groups, the percentage of seropositive subjects for each serotype increased 28 days after the third dengue injection compared to baseline.

As observed for GMTs, the percentage of seropositive subjects for each serotype was similar in both groups, and was respectively in Group 1 and Group 2:

52.7% and 56.5% for serotype 1
84.0% and 88.0% for serotype 2
85.1% and 90.7% for serotype 3
88.3% and 86.0% for serotype 4

Whatever the group, the percentage of seropositive subjects was above 80% for serotypes 2, 3, and 4 and was lower for serotype 1.

The percentage of seropositive subjects against at least 3 serotypes and against all 4 serotypes was also similar post-injection 3 in both groups and was respectively in Group 1 and Group 2:

73.4% and 82.4% against at least 3 serotypes
50.0% and 42.6% against all 4 serotypes.

Conclusions

In a non-endemic adult population:

Whatever the schedule (standard [0-6-12 months] or compressed [0-2-6 months]), the GMTs and the percentage of seropositive subjects for each serotype increased 28 days after the third dengue injection compared to baseline.

Post-injection 3, the results were comparable in terms of GMTs and in terms of percentage of seropositive subjects, between the 2 schedules for each serotype.

Post-injection 3, the levels of GMTs and the percentage of seropositive subjects were the lowest for serotype 1. GMTs for serotype 4 were the highest.

Impact of Concomitant CYD and YF Vaccination on YF Immune Response

The considered objective was to describe the YF humoral immune response at baseline and 1, 3, and 7 months after injection of the YF vaccine at M00 in Groups 3 and 4.

Definitions

PRNT: Plaque Reduction Neutralization Test,
GMTs: Geometric mean titers,
GMTRs: Geometric mean of individual titers ratios,
Ab: neutralizing antibody,
FAS: Full Analysis Set.
FV (Flavivirus) Baseline Status Based on Laboratory Confirmation (Dengue $PRNT_{50}$+YF $PRNT_{50}$)
GMTs The hereinafter table 6 presents the summary of GMTs and GMTR of Ab against YF (laboratory confirmation—YF $PRNT_{50}$) in the FAS.

TABLE 6

| Timepoint/Ratio | Group 3 (N = 114) | | | Group 4 (N = 28) | | |
|---|---|---|---|---|---|---|
| | M | GM | (95% CI) | M | GM | (95% CI) |
| Pre-Inj 1 | 114 | 9.82 | (7.92; 12.2) | 28 | 10.5 | (6.30; 17.5) |
| 1 month Post-Inj 1 | 114 | 5782 | (4420; 7563) | 28 | 6398 | (4175; 9804) |
| 3 month Post-Inj 1 | 100 | 3355 | (2557; 4401) | 27 | 2695 | (1558; 4662) |
| 7 month Post-Inj 1 | 93 | 2078 | (1514; 2851) | 25 | 1835 | (1054; 3197) |
| 1 month Post-Inj 1/Pre-Inj 1 | 114 | 362 | (263; 498) | 28 | 380 | (222; 653) |
| 3 month Post-Inj 1/Pre-Inj 1 | 100 | 208 | (152; 284) | 27 | 161 | (83.8; 310) |
| 7 month Post-Inj 1/Pre-Inj 1 | 93 | 126 | (87.1; 183) | 25 | 105 | (56.7; 196) |

N: number of subjects analyzed according to the Full Analysis Set
M: number of subjects with available data for the endpoint At baseline, YF GMTs were similar in Groups 3 and 4 9.82 (l/dil) and 10.5 (l/dil) respectively.

One month after injection of the YF vaccine, YF GMTs were similar in subjects who received YF and CYD dengue vaccines concomitantly at M00 (Group 3) and in subjects who received YF vaccine only at M00 (Group 4): 5782 (l/dil) and 6398 (l/dil) respectively.

Three and seven months after injection of the YF vaccine, YF GMTs were also similar in Groups 3 and 4, and were respectively:
3355 (l/dil) and 2695 (l/dil) at M03,
2078 (l/dil) and 1835 (l/dil) at M07.

Seropositivity

Table 7 below presents the number and percentage of subjects with Ab titer ≥10 l/dil against YF (laboratory confirmation—YF $PRNT_{50}$) in the FAS.

comitantly at M00 (Group 3) and in subjects who received YF vaccine only at M00 (Group 4): 98.2% and 100.0%, respectively.

Three and seven months after injection of the YF vaccine, the percentage of seropositive subjects for YF remained high and similar in the two groups (≥98.9%).

FV Baseline Status Based on Laboratory Confirmation (Dengue $PRNT_{50}$+YF $PRNT_{80}$)

GMTs

The hereinafter table 8 presents the summary of GMTs and GMTR of Ab against YF (laboratory confirmation—YF $PRNT_{80}$) in the FAS.

TABLE 7

| Timepoint | Criteria | Group 3 (N = 114) | | | Group 4 (N = 28) | | |
|---|---|---|---|---|---|---|---|
| | | n/M | % | (95% CI) | n/M | % | (95% CI) |
| Pre-Inj 1 | >=10 l/dil | 34/114 | 29.8 | (21.6; 39.1) | 9/28 | 32.1 | (15.9; 52.4) |
| 1 month Post-Inj 1 | >=10 l/dil | 112/114 | 98.2 | (93.8; 99.8) | 28/28 | 100.0 | (87.7; 100.0) |
| 3 months Post-Inj 1 | >=10 l/dil | 99/100 | 99.0 | (94.6; 100.0) | 27/27 | 100.0 | (87.2; 100.0) |
| 7 months Post-Inj 1 | >=10 l/dil | 92/93 | 98.9 | (94.2; 100.0) | 25/25 | 100.0 | (86.3; 100.0) |

N: number of subjects analyzed according to the Full Analysis Set
M: number of subjects with available data for the endpoint At baseline, the percentage of seropositive subjects for YF was similar in Groups 3 and 4: 29.8% and 32.1%, respectively.

One month after injection of the YF vaccine, the percentage of seropositive subjects for YF was high and similar in subjects who received YF and CYD dengue vaccines con-

TABLE 8

| Timepoint/Ratio | Group 3 (N = 114) | | | Group 4 (N = 28) | | |
|---|---|---|---|---|---|---|
| | M | GM | (95% CI) | M | GM | (95% CI) |
| Pre-Inj 1 | 114 | 5.68 | (5.12; 6.31) | 28 | 6.25 | (4.54; 8.60) |
| 1 month Post-Inj 1 | 114 | 464 | (343; 628) | 28 | 525 | (280; 984) |
| 3 month Post-Inj 1 | 100 | 343 | (267; 441) | 27 | 223 | (134; 373) |
| 7 month Post-Inj 1 | 93 | 256 | (196; 335) | 25 | 164 | (99.2; 273) |
| 1 month Post-Inj 1/Pre-Inj 1 | 114 | 42.3 | (31.2; 57.4) | 28 | 44.1 | (23.1; 84.4) |
| 3 month Post-Inj 1/Pre-Inj 1 | 100 | 31.3 | (24.2; 40.5) | 27 | 18.7 | (10.9; 32.0) |
| 7 month Post-Inj 1/Pre-Inj 1 | 93 | 23.2 | (17.5; 30.8) | 25 | 13.5 | (7.92; 23.2) |

N: number of subjects analyzed according to the Full Analysis Set
M: number of subjects with available data for the endpoint At baseline, YF GMTs were similar in Groups 3 and 4: 5.68 (l/dil) and 6.25 (l/dil), respectively.

One month after injection of the YF vaccine, YF GMTs were similar in subjects who received YF and CYD dengue vaccines concomitantly at M00 (Group 3) and in subjects who received YF vaccine only at M00 (Group 4): 464 (l/dil) and 525 (l/dil), respectively.

Three and seven months after injection of the YF vaccine, YF GMTs were also similar in Groups 3 and 4, and were respectively:
- 343 (l/dil) and 223 (l/dil) at M03,
- 256 (l/dil) and 164 (l/dil) at M07.

YF GMTs were numerically lower with the YF $PRNT_{80}$ assay than with the YF $PRNT_{50}$.

Seropositivity

The hereinafter table 9 presents the number and percentage of subjects with Ab titer ≥10 l/dil against YF (laboratory confirmation—YF PRNT80) in the FAS.

TABLE 9

Number and percentage of subjects with Ab titer >=10 l/dil against YF - YF $PRNT_{80}$ - Full Analysis Set

| Timepoint | Criteria | Group 3 (N = 114) | | | Group 4 (N = 28) | | |
| --- | --- | --- | --- | --- | --- | --- | --- |
| | | n/M | % | (95% CI) | n/M | % | (95% CI) |
| Pre-Inj 1 | >=10 l/dil | 6/114 | 5.3 | (2.0; 11.1) | 2/28 | 7.1 | (0.9; 23.5) |
| 1 month Post-Inj 1 | >=10 l/dil | 112/114 | 98.2 | (93.8; 99.8) | 28/28 | 100.0 | (87.7; 100.0) |
| 3 months Post-Inj 1 | >=10 l/dil | 99/100 | 99.0 | (94.6; 100.0) | 27/27 | 100.0 | (87.2; 100.0) |
| 7 months Post-Inj 1 | >= 10 l/dil | 92/93 | 98.9 | (94.2; 100.0) | 24/25 | 96.0 | (79.6; 99.9) |

N: number of subjects analyzed according to the Full Analysis Set
M: number of subjects with available data for the endpoint At baseline, the percentage of seropositive subjects for YF was similar in Groups 3 and 4: 5.3% and 7.1%, respectively.

One month after injection of the YF vaccine, the percentage of seropositive subjects for YF was high and similar in subjects who received YF and CYD dengue vaccines concomitantly at M00 (Group 3) and in subjects who received YF vaccine only at M00 (Group 4): 98.2% and 100.0%, respectively.

Three and seven months after injection of the YF vaccine, the percentage of seropositive subjects for YF remained high and similar in the two groups (≥96.0%).

Impact of Concomitant CYD and YF Vaccination on Dengue Immune Response

Comparison of dengue immune response in flavivirus non-immune subjects (i.e. subjects with <10 l/dil for all serotypes with parental dengue virus strains and for YF virus at baseline; FV baseline status based on dengue $PRNT_{50}$ and YF $PRNT_{50}$) from Groups 2 and 3 after a completed vaccination schedule (PD3):

For serotypes 1-4, GMTs (l/dil) were similar in Groups 2 and 3 respectively:
- Serotype 1: 13.7 and 18.8
- Serotype 2: 60.1 and 50.7
- Serotype 3: 44.7 and 27.3
- Serotype 4: 85.0 and 65.9

Comparison of dengue immune response in flavivirus immune subjects (i.e. subjects with ≥10 l/dil for at least one serotype with parental dengue virus strains or for YF virus; FV baseline status based on dengue $PRNT_{50}$ and YF $PRNT_{50}$) from Groups 2 and 3 after a completed vaccination schedule (PD3):

For serotypes 1-4, GMTs (l/dil) were similar in Groups 2 and 3 respectively:
- Serotype 1: 17.1 and 26.8
- Serotype 2: 59.9 and 52.7
- Serotype 3: 67.2 and 55.1
- Serotype 4: 82.3 and 107

Comparison of dengue immune response in flavivirus non-immune subjects (i.e. subjects with <10 l/dil for all serotypes with parental dengue virus strains and for YF virus at baseline; FV baseline status based on dengue $PRNT_{50}$ and YF $PRNT_{80}$) from Groups 2 and 3 after a completed vaccination schedule (PD3):

For serotypes 1-4, GMTs (l/dil) were similar in Groups 2 and 3 respectively:
- Serotype 1: 14.4 and 18.5
- Serotype 2: 51.4 and 46.4
- Serotype 3: 47.3 and 30.2
- Serotype 4: 89.2 and 71.2

Comparison of dengue immune response in flavivirus immune subjects (i.e. subjects with ≥10 l/dil for at least one serotype with parental dengue virus strains or for YF virus; FV baseline status based on dengue $PRNT_{50}$ and YF $PRNT_{80}$) from Groups 2 and 3 respectively after a completed vaccination schedule (PD3):
- Serotype 1: 17.2 and 79.0
- Serotype 2: 68.1 and 133
- Serotype 3: 71.2 and 130
- Serotype 4: 78.5 and 182

Safety

Assessment Methods

Post-Vaccination Observation Period

Subjects were kept under observation for 30 minutes after each CYD dengue and/or YF vaccination to ensure their safety. Any adverse events (AEs) were that occurred during this period was noted on the source document and identified as an immediate event/reaction; and was additionally recorded in an electronic case report form (eCRF), as follows:

Any unsolicited systemic AE observed to occur during the first 30 minutes post-vaccination was also recorded on the eCRF, i.e., as immediate unsolicited systemic AE, Solicited and unsolicited injection site reactions and solicited systemic reactions were not actively solicited during the 30 minute-period. If they occur within 30 minutes of vaccination, they were recorded and analyzed as starting on the day of vaccination, Any Serious adverse events (SAEs) occurred during the first 30 minutes post-vaccination was reported in the same way as any other SAE and to the Sponsor.

Reactogenicity (Solicited Reactions from D00 to Day 07 or Day 00 to Day 14 After Each Vaccination)

After each vaccination with CYD dengue or YF vaccine, subjects were provided with a safety diary card (DC), a digital thermometer, and a flexible ruler, and were instructed how to use them. The following items were recorded by the subjects in the DC on the day of vaccination and for the next 7 days (i.e., D00 to D07) until resolution:

Daily temperature, with the route by which it was taken,
Daily measurement or intensity grade of all other solicited injection site and systemic reactions,
Action taken for each event, if any (e.g., medication).
Unsolicited Adverse Events From Day 00 to Day 28 After Each Administration of CYD Dengue or YF Vaccine In addition to recording solicited reactions, subjects were instructed to record any other medical events that could occur during the 28-day period after each administration of CYD dengue or YF vaccine. Space was provided in the DC for this purpose. For each AE, the following information was to be recorded:

Start and stop dates,
Intensity of the event:
For measurable unsolicited AEs, the size of the AE was collected and analyzed based on the corresponding scale used for solicited reactions.
Other AEs were classified according to the following scale:
Grade 1: No interference with activity,
Grade 2: Some interference with activity,
Grade 3: Significant; prevents daily activity,
Action taken for each AE, if any (medication, etc.)

AEs likely to be related to the product, whether serious or not, that persisted at the end of the trial were to be followed up by the Investigator until their complete disappearance or the stabilization of the subject's condition. The Investigator informed the Sponsor of the date of final disappearance of the event.

The safety profile of CYD dengue vaccine was similar for the considered schedule of administration was consistent to what was observed in previous clinical trials. After each injection of CYD dengue vaccine, the most frequently reported solicited injection site reaction was injection site pain, and the most frequently reported solicited systemic reactions were headache, malaise, and myalgia. The solicited reactions were usually of mild intensity and of short duration (0-3 days). The occurrence of solicited systemic reactions tended to decrease after the second and the third injections of the dengue vaccine as compared to the first injection. Unsolicited non-serious adverse reactions were reported by less than 10% of the subjects after the first CYD injection. This proportion tended to decrease post-injection 2 and post-injection 3. During the entire study, only 1 SAE was assessed as related to vaccination as per the Investigator (blighted ovum). No serious AESIs were reported.

Three non-serious AESIs were reported post-injection 1: flushing of the face, asthma, and rash on the neck, by subjects with a relevant medical history. Two of these events were assessed as related to vaccination. All three subjects recovered and did not experience similar events after the second and the third injections. No safety concern was raised regarding inadvertent exposure to CYD dengue vaccine before or during pregnancy.

Overall, no safety concerns emerged in the present study after the administration of the CYD dengue vaccine, confirming that the safety profile of the CYD dengue vaccine is satisfactory.

As regards to YF and CYD dengue vaccines co-administration at the first injection, an increase in the overall reactogenicity (reactogenicity of both vaccines combined) was observed. However, the overall safety profile of YF and CYD dengue vaccines remained satisfactory when co-administered.

The safety profile of CYD dengue vaccine was consistent with the good safety profile of CYD dengue vaccine observed in previous clinical trials.

The co-administration of YF and CYD dengue vaccines did not have a major impact on the safety profile of each vaccine: the safety profiles of YF and CYD dengue vaccines remained satisfactory when co-administered.

Conclusions

Comparison of the Two Dengue Vaccine Administration Schedules (Standard [0-6-12 Months] and Compressed [0-2-6 Months]) in Groups 1 and 2 (No Concomitant Administration with YF)

In a non-endemic adult population and for the 2 schedules:

The GMTs and the percentage of seropositive subjects increased 28 days after each injection compared to each pre-injection timepoint, and this for each serotype but to a lower extent for serotype 1,
PD2 GMTs were higher than PD1 for all serotypes. PD3 GMTs were similar to PD2 GMTs (serotypes 1, 2, and 3) or lower (serotype 4). The percentage of seropositive subjects PD2 was higher than PD1 and similar to PD3, for each serotype,
The results were comparable in terms of GMTs and in terms of percentage of seropositive subjects between the 2 schedules, for each serotype, post-injection 2 and post-injection 3.

Impact on YF Immune Response of Concomitant YF and Dengue Vaccination

No impact of dengue and YF concomitant vaccination was observed on the YF immune response, in terms of YF GMTs and percentage of YF seropositive subjects, as measured at 1, 3, and 7 months post YF vaccination, whatever the PRNT assay used. Although there were differences in terms of GMT levels according to the method used ($PRNT_{50}$ or $PRNT_{80}$), the same conclusions in terms of impact on the YF immune response could be drawn from both methods.

Impact on Dengue Immune Response of Concomitant YF and Dengue Vaccination

Concomitant YF and CYD vaccination reduced the dengue immune response post-dose 1, in terms of GMTs for serotypes 3 and 4, and in terms of percentage of seropositive subjects for serotypes 2, 3 and 4. This effect was much less marked PD3 and for certain serotypes the effect had disappeared altogether.

As regards to YF and CYD dengue vaccines co-administration at the first injection, an increase in the overall reactogenicity (reactogenicity of both vaccines combined) was observed. However, the overall safety profile of YF and CYD dengue vaccines remained satisfactory when concomitantly administered.

Sequence Listing

| SEQ ID N° | Corresponding definitions |
|---|---|
| 1 | prM + E nucleotide sequence of a serotype 1 dengue fever strain |
| 2 | prM + E nucleotide sequence of a serotype 2 dengue fever strain |
| 3 | prM + E nucleotide sequence of a serotype 3 dengue fever strain |
| 4 | prM + E nucleotide sequence of a serotype 4 dengue fever strain |
| 5 | prM + E nucleotide sequence of a serotype 2 dengue fever strain (CYD-2V) |
| 6 | Entire nucleotide sequence of VDV1 |
| 7 | Entire nucleotide sequence of VDV2 |

The invention claimed is:

1. A method for inducing in an immunocompetent, dengue immune human subject a protective immune response against yellow fever and a neutralizing antibody response against each of the four serotypes of dengue, wherein:
   said method comprises concomitantly administering a yellow fever (YF) vaccine to the immunocompetent, dengue immune human subject together with a tetravalent dengue vaccine which comprises a live attenuated dengue virus of each of serotypes 1 to 4, wherein said live attenuated dengue viruses of each of serotypes 1 to 4 comprise nucleic acid sequences encoding pre-membrane (prM) and envelope (E) proteins from a dengue virus;
   the dengue vaccine is either a separate composition from the yellow fever vaccine or is mixed together with the yellow fever vaccine before administration;
   the live attenuated dengue virus of serotype 1, the live attenuated dengue virus of serotype 3 and the live attenuated dengue virus of serotype 4 are each a live attenuated chimeric dengue virus; and
   the live attenuated dengue virus of serotype 2 is selected from the group consisting of a live attenuated dengue virus and a live attenuated chimeric dengue virus.

2. The method according to claim 1, wherein the live attenuated tetravalent dengue vaccine is administered according to a three-dose dengue vaccination schedule, the first dose of said dengue vaccine being concomitantly administered with the YF vaccine.

3. The method according to claim 1, wherein:
   the live attenuated dengue virus of serotype 1, the live attenuated dengue virus of serotype 2, the live attenuated dengue virus of serotype 3 and the live attenuated dengue virus of serotype 4 are each a live attenuated chimeric dengue virus.

4. The method according to claim 3, wherein the live attenuated chimeric dengue virus comprises one or more proteins from an attenuated yellow fever virus.

5. The method according to claim 3, wherein the live attenuated chimeric dengue virus comprises a genome of an attenuated yellow fever virus whose prM-E sequence has been substituted with the prM-E sequence of a dengue virus.

6. The method according to claim 1, wherein the immunocompetent human subject resides in a dengue endemic area.

7. A method for inducing in an immunocompetent, dengue immune human subject a protective immune response against yellow fever and a neutralizing antibody response against each of the four serotypes of dengue, wherein said method comprises:
   concomitantly administering a tetravalent dengue vaccine which comprises a live attenuated dengue antigen of each of serotypes 1 to 4 to the immunocompetent, dengue immune human subject together with a yellow fever (YF) vaccine, wherein said live attenuated dengue viruses of each of serotypes 1 to 4 comprise nucleic acid sequences encoding pre-membrane (prM) and envelope (E) proteins from a dengue virus;
   the live attenuated tetravalent dengue vaccine being administered according to a multi-dose dengue vaccination schedule, the first dose of said dengue vaccine being concomitantly administered with the YF vaccine;
   the first dose of the dengue vaccine being either a separate composition from the yellow fever vaccine or being mixed together with the yellow fever vaccine before administration;
   wherein
   i) the live attenuated dengue virus of serotype 1, the live attenuated dengue virus of serotype 3 and the live attenuated dengue virus of serotype 4 are each a live attenuated chimeric dengue virus, and
   ii) the live attenuated dengue virus of serotype 2 is selected from the group consisting of a live attenuated dengue virus and a live attenuated chimeric dengue virus.

8. The method according to claim 7, wherein the live attenuated tetravalent dengue vaccine is administered according to a two dose or three-dose dengue vaccination schedule, the first dose of said dengue vaccine being concomitantly administered with the YF vaccine.

9. The method according to claim 7, wherein the live attenuated chimeric dengue virus comprises one or more proteins from an attenuated yellow fever virus.

10. The method according to claim 7, wherein the live attenuated chimeric dengue virus comprises a genome of an attenuated yellow fever virus whose prM-E sequence has been substituted with the prM-E sequence of a dengue virus.

11. The method according to claim 7, wherein the subject resides in a dengue endemic area.

12. The method according to claim 1, wherein the yellow fever vaccine comprises at least one yellow fever virus of strain YF17D.

13. The method according to claim 7, wherein the yellow fever vaccine comprises at least one yellow fever virus of strain YF17D.

14. The method according to claim 1, wherein:
a second dose of said dengue vaccine is administered to the subject 2 months after the administration of a first dose and a third dose of said dengue vaccine is administered to the subject 6 months after the administration of the first dose; or
a second dose of said dengue vaccine is administered to the subject 6 months after the administration of a first dose and a third dose of said dengue vaccine is administered to the subject 12 months after the administration of a first dose.

15. The method according to claim 7, wherein:
a second dose of said dengue vaccine is administered to the subject 2 months after the administration of the first dose and a third dose of said dengue vaccine is administered to the subject 6 months after the administration of the first dose; or
a second dose of said dengue vaccine is administered to the subject 6 months after the administration of the first dose and a third dose of said dengue vaccine is administered to the subject 12 months after the administration of the first dose.

16. The method according to claim 1, wherein the live attenuated tetravalent dengue vaccine is administered according to a two-dose dengue vaccination schedule, the first dose of said dengue vaccine being concomitantly administered with the YF vaccine.

17. The method according to claim 7, wherein:
the live attenuated dengue virus of serotype 1, the live attenuated dengue virus of serotype 2, the live attenuated dengue virus of serotype 3 and the live attenuated dengue virus of serotype 4 are each live attenuated chimeric dengue virus.

18. The method according to claim 8, wherein the live attenuated tetravalent dengue vaccine is administered according to a two dose dengue vaccination schedule, the first dose of said dengue vaccine being concomitantly administered with the YF vaccine.

19. The method according to claim 1, wherein the human subject is aged between 9 and 60 years old.

20. The method according to claim 7, wherein the human subject is aged between 9 and 60 years old.

21. The method according to claim 1, wherein the live attenuated dengue virus of serotype 1 comprises a prM-E nucleic acid sequence having at least 90% sequence identity to SEQ ID NO. 1; the live attenuated dengue virus of serotype 2 comprises a prM-E nucleic acid sequence having at least 90% sequence identity to SEQ ID NO. 2; the live attenuated dengue virus of serotype 3 comprises a prM-E nucleic acid sequence having at least 90% sequence identity to SEQ ID NO. 3 and the live attenuated dengue virus of serotype 4 comprises a prM-E nucleic acid sequence having at least 90% sequence identity to SEQ ID NO. 4.

22. The method according to claim 7, wherein the live attenuated dengue virus of serotype 1 comprises a prM-E nucleic acid sequence having at least 90% sequence identity to SEQ ID NO. 1; the live attenuated dengue virus of serotype 2 comprises a prM-E nucleic acid sequence having at least 90% sequence identity to SEQ ID NO. 2; the live attenuated dengue virus of serotype 3 comprises a prM-E nucleic acid sequence having at least 90% sequence identity to SEQ ID NO. 3 and the live attenuated dengue virus of serotype 4 comprises a prM-E nucleic acid sequence having at least 90% sequence identity to SEQ ID NO. 4.

23. The method according to claim 1, wherein the live attenuated dengue virus of serotype 1 comprises a prM-E nucleic acid sequence having 100% sequence identity to SEQ ID NO. 1; the live attenuated dengue virus of serotype 2 comprises a prM-E nucleic acid sequence having 100% sequence identity to SEQ ID NO. 2; the live attenuated dengue virus of serotype 3 comprises a prM-E nucleic acid sequence having 100% sequence identity to SEQ ID NO. 3 and the live attenuated dengue virus of serotype 4 comprises a prM-E nucleic acid sequence having 100% sequence identity to SEQ ID NO. 4.

24. The method according to claim 1, wherein the live attenuated dengue virus of serotype 1 comprises a prM-E nucleic acid sequence having 100% sequence identity to SEQ ID NO. 1; the live attenuated dengue virus of serotype 2 comprises a prM-E nucleic acid sequence having 100% sequence identity to SEQ ID NO. 2; the live attenuated dengue virus of serotype 3 comprises a prM-E nucleic acid sequence having 100% sequence identity to SEQ ID NO. 3 and the live attenuated dengue virus of serotype 4 comprises a prM-E nucleic acid sequence having 100% sequence identity to SEQ ID NO. 4.

* * * * *

SEQUENCE LISTING

<160> NUMBER OF SEQ ID NOS: 7

<210> SEQ ID NO 1
<211> LENGTH: 1983
<212> TYPE: RNA
<213> ORGANISM: artificial sequences
<223> OTHER INFORMATION: "CYD1 prmE"
<220> FEATURE:
<223> OTHER INFORMATION: CYD1 prmE

<400> SEQUENCE: 1

| | | | | | |
|---|---|---|---|---|---|
| uuucaucuga | ccacacgagg | gggagagccg | cauaugauag | uuaccaagca | ggaaagagga | 60 |
| aagucacuuu | uguuuaagac | cucagcuggu | gucaacaugu | gcacccuuau | ugcgauggau | 120 |
| uugggagagu | auugugagga | acaaugacu | uacaaauguc | cucgaaucac | ugaggcggaa | 180 |
| ccagaugacg | uugauuguug | gugcaaugcc | acagacacau | gggugaccua | uggaacugu | 240 |
| ucccaaacug | gcgagcaccg | acgagacaaa | cguuccgucg | cacugccccc | acacgugggga | 300 |
| cuuggucuag | aaacaagaac | cgaaacgugg | auguccucug | aaggcgcuug | gaaacaaaua | 360 |
| caaagagugg | agacuugggc | ccugagacac | ccaggauuca | cagugauagc | ccuuuucua | 420 |
| gcacaugcca | uaggaacauc | caucacccag | aaagggauua | uuucauuu | guugaugcug | 480 |
| guaacaccau | ccauggccau | gcgaugugug | ggaauaggca | acaggacuu | cguggaagga | 540 |
| cugucaggag | caacgugggu | agaugugua | cuggaacaug | gaaguugcgu | caccaccaug | 600 |
| gcaaaagaua | aaccaacauu | ggacauugaa | ucucuugaaga | cggaagcac | aaacccugcc | 660 |
| guccuucgaa | aacugugcau | cgaagcuaaa | auaucaaaca | ccaccaccga | uucaagaugc | 720 |
| ccaacacaag | gagaagccac | acuggugaa | gagcaagacg | cgaauuuugu | gugucgacga | 780 |
| acguuugugu | acagaggcug | gggcaauggc | uguggggcucu | ucggaaaagg | uagccuaaua | 840 |
| acgugugcua | aguucaagug | ugacaaaa | cuggaaggaa | agauaguuca | auaugaaaac | 900 |
| uugaaauauu | caguaauagu | caccgucca | acuggagacc | agcaccaggu | gggaaaugaa | 960 |
| agcacagaac | augggacaac | agcaacuaua | acaccucaag | cucccacguc | ggaaauacag | 1020 |
| cugaccgacu | acgagcucu | aacauuggau | ugcuccaccua | gaacaggacu | agacuucaau | 1080 |
| gaaauggugu | uguugacaau | gaaagaaaga | ucauggcuag | uccacaaaca | augguuucua | 1140 |
| gaccuaccac | ugccuuggac | ucgggagcu | acaacgucac | aagagacuug | gaacagacaa | 1200 |
| gauuugcugg | uaacauuuaa | gacagcucau | gcaaagaagc | aggaaguagu | cguacuagga | 1260 |
| ucacaagaag | gagcaaugca | cacugcguug | accggagcga | cagaauccaa | acgucugga | 1320 |
| acgacaacaa | uuuuugcagg | cacuugaaa | uguagacuaa | aauggacaa | acugacucua | 1380 |
| aaagggaugu | cauaugugau | gugcacaggc | ucauucaagc | uagagaaaga | gguggcugag | 1440 |
| acccagcaug | gaaccguucu | agugcagguu | aaauacgaag | gaacagaugc | accaugcaag | 1500 |
| aucccuuuuu | cgacccaaga | ugaaaaagga | guaaccccaga | augggagagu | gauaacagcc | 1560 |
| aacccuauag | ucacugacaa | ggaaaaacca | gucaacauug | aggcagaacc | accuuuuggu | 1620 |
| gagaguuaca | ucguguagg | agcaggugaa | aaagcuuuga | acuaagcug | guucaagaaa | 1680 |
| ggaagcacca | uagggaaaau | guuugaggca | acugcccgag | gagcacgaag | gauggccaua | 1740 |
| cuggagaca | ccgcauggga | cuuugguucu | uaggaggag | uguucacauc | uguuggaaaa | 1800 |
| cuaguacacc | agauuuuugg | aacugcauau | ggaguuuugu | ucagcggugu | uccuggacc | 1860 |
| augaaaauag | gaauagggu | ucugcugaca | uggcuaggau | uaaacucaag | gagcacguce | 1920 |
| cuuucgauga | cgugcauugc | aguuggccug | guaacacugu | accuaggagu | caugguugc | 1980 |

| gcc | 1983 |

<210> SEQ ID NO 2
<211> LENGTH: 1983
<212> TYPE: RNA
<213> ORGANISM: artificial sequences
<223> OTHER INFORMATION: "CYD2 prmE"
<220> FEATURE:
<223> OTHER INFORMATION: CYD2 prmE

<400> SEQUENCE: 2

| uuccaucuaa ccacacguaa cggagaacca cacaugaucg ucaguagaca agagaaaggg | 60 |
| aaaagucuug uguuuaaaac agaggauggc gugaacaugu gcacccucau ggccauggac | 120 |
| cuuggugaau ugugugaaga cacaaucacg uacaaguguc cccuucucag gcagaaugag | 180 |
| ccagaagaca uagacugcug gugcaacucc acguccacgu ggguaaccua ugggacuugu | 240 |
| accaccacgg gagaacauag aagagaaaaa agaucagugg cacucguucc acauguggga | 300 |
| augggacugg agacgcgaac ugaaacaugg augucaucag aagggcuug gaaacaugcc | 360 |
| cagagaauug aaauuuggau ccugagacau ccaggcuuca ccauaauggc agcaauccug | 420 |
| gcauacacca uagggacgac acauuuccag agagcacuga uuuucaucuu acugacagcu | 480 |
| gucgcuccuu caaugacaau gcguugcaua ggaauaucaa auagagacuu uguagaaggg | 540 |
| guuucaggag gaagcugggu ugacauaguc uuagaacaug gaagcugugu gacgacgaug | 600 |
| gcaaaaaaca aaccaacauu ggauuuugaa cugauaaaaa cagaagccaa acagccugcc | 660 |
| acccuaagga aguacuguau agaggcaaag cuaaccaaca caacaacaga aucucguugc | 720 |
| ccaacacaag gggaacccag ccuaaaugaa gagcaggaua aaagguucgu cugcaaacac | 780 |
| uccaugguag acagaggaug gggaaauuga uguggauuau uuggaaaggg aggcauugug | 840 |
| accugugcua uguucacaug caaaaagaac auggagggaa aaguugugca gccagaaaac | 900 |
| uuggaauaca ccauugugguu aacaccccac ucagggaag agcaugcggu cggaaaugac | 960 |
| acaggaaaac auggcaagga aaucaaagua acaccacaga guuccaucac agaagcagaa | 1020 |
| uugacagguu auggcacugu cacgauggag ugcucuccga gaacaggccu cgacuucaau | 1080 |
| gagauggugu ugcugcagau ggaaaauaaa gcuuggcugg ugcauaggca augguuccua | 1140 |
| gaccugccgu uaccauggcu gcccggagcg gacacacaag ggucaaauug gaucaaaaaa | 1200 |
| gaaacauugg ucacuuucaa aaauccucau gcgaagaaac aggauguuuu uguuuuagga | 1260 |
| ucccaagaag gggccaugca cacagcacuc acaggggcca cagaaaucca aaugucauca | 1320 |
| ggaaacuuac ucuucacagg acaucucaag ugcaggcuga aauggacaa gcuacagcuc | 1380 |
| aaaggaaugu cauacucuau gugcacagga aaguuuaaag uugugaagga auagcagaa | 1440 |
| acacaacaug gaacaauagu uaucaggguug caguaugaag gggacggcuc uccauguaaa | 1500 |
| aucccuuuug agauaaugga uuuggaaaaa agacaugucu uaggucgccu gaucacaguc | 1560 |
| aacccaauug ugacagaaaa agauagccca gucaacauag aagcagaacc uccauucgga | 1620 |
| gacagcuaca ucaucauagg aguagagccg ggacaacuga agcucaacug guuuaagaaa | 1680 |
| ggaaguucua ucggccaaau guuugagaca acaaugaggg gggcgaagag aauggccauu | 1740 |
| uugggugaca cagccuggga uuuuggauc cuggaggag uguuuacauc uauaggaaaa | 1800 |
| gcccuccacc aagucuuugg agcaaucuau ggagcugccu ucagugggu cucauggacu | 1860 |
| augaaaaucc ucauaggagu cauuaucaca uggauaggaa ugaauucacg cagcaccuca | 1920 |
| cugucugugu cacuaguauu ggugggaguc gugacgcugu auuggggagu augguggggc | 1980 |

| | |
|---|---:|
| gcc | 1983 |

<210> SEQ ID NO 3
<211> LENGTH: 1977
<212> TYPE: RNA
<213> ORGANISM: artificial sequences
<223> OTHER INFORMATION: "CYD3 prmE"
<220> FEATURE:
<223> OTHER INFORMATION: CYD3 prmE

<400> SEQUENCE: 3

| | |
|---|---:|
| uuccacuuaa cuucacgaga uggagagccg cgcaugauug ggggaagaa ugaaagaggg | 60 |
| aaaucccuac uuuuuaagac agcuucugga aucaacaugu gcacacucau agccauggac | 120 |
| uugggagaga ugugugauga cacggucacu acaaaugcc cccucauugc cgaaguggaa | 180 |
| ccugaagaca uugacugcug gugcaaccuu acaucgacau gggugacuua uggaacgugc | 240 |
| aaucaagcug gggagcauag acgcgacaag agaucagugg cguuagcucc ccaugucggc | 300 |
| auggacugg acacacgcac ccaaaccugg augucggcug aaggagccuug agacaaguc | 360 |
| gagaagguag agacauggc ucuuaggcac ccagggucca ccauacuagc ucauuucuu | 420 |
| gcucauuaca uaggcacuuc ccugacccag aaagugguua uuuuauacu acuaaugcug | 480 |
| gucacuccau ccauggcaau gagaugcgug ggaguaggaa acagagauuu guggaaggu | 540 |
| cugucgggag cuacguggu ugauguggu cuggagcacg gugggugugu gaccaccaug | 600 |
| gcuaagaaca agccuacgcu ggacauagag cuucagaaga ccgaggccac ccaacuggcg | 660 |
| acccuucgaa aguuaugcau ugagggaaaa auuaccaaca uaacaacuga cucaaggugu | 720 |
| ccuacccagg gggaagcgau uuaccugag gagcaggacc agaacuacgu auguaagcac | 780 |
| acauaugugg auagaggcug gggaaacggu guggguuugu uggaaaaagg aagcuuggug | 840 |
| acaugcgcga aauucaaug ucuagaauca auagagggaa aagugguca acaugagaac | 900 |
| cucaaauaca cugucaucau uacagugcac acaggaaacc aacaccaggu gggaaaugac | 960 |
| acgcagggag ucacggcuga auaacacccc caggcaucaa ccguugaagc caucuugccu | 1020 |
| gaauauggaa cccuugggcu agaaugcuca ccacggacag guuggauuu caaugaaaug | 1080 |
| auuuuauuga caaugaaaaa caaagcaugg augguacaua ggcaaugguu cuugaccua | 1140 |
| ccccuaccau ggacaucagg agcuacaaca gagacaccaa cuuggaacag gaaagagcuu | 1200 |
| cuugugacau ucaaaaugc acaugcaaaa agcaagaag uaguguccu ugggaucgcaa | 1260 |
| gagggagcaa ugcacacagc gcugacagga gcuacagaga uccaaaacuc aggaguaca | 1320 |
| agcauuuuug cggggcacuu gaauguaga cuuaagaugg acaaauugga acucaagggg | 1380 |
| augagcuaug caaugugcuu gaauaccuuu guguugaaga agaagucuc cgaaacgcag | 1440 |
| cauggggacaa uacucauuaa gguugaguac aaagggaag augcaccuug caagauuccu | 1500 |
| uucuccacag aggauggaca agggaaagcu cacaaugua gacugaucac agccaaccca | 1560 |
| gugguagacca agaaggagga gccgucaac auugaggcug aaccccuuu uggggaaagu | 1620 |
| aacauaguga uuggaauugg agacaaagcc uugaaaauua acugguacaa gaaggaagc | 1680 |
| ucgauuggga agauguucga ggccacugcc agaggugcaa ggcgcauggc caucuuggga | 1740 |
| gacacagccu gggacuuugg aucagugggu gguguucuaa auucauuagg gaaaauggug | 1800 |
| caccaaauau ucggaagugc uuacacagcc cuguuagug gagcucaug gauaaugaaa | 1860 |
| auuggaauag guguccucuu aaccuggaua ggguugaauu caaaaaacac uuccaugucea | 1920 |
| uuuucaugcg uugcgauagg aauuaucaca cucuaucugg gagccguggu acaggcc | 1977 |

<210> SEQ ID NO 4
<211> LENGTH: 1983
<212> TYPE: RNA
<213> ORGANISM: artificial sequences
<223> OTHER INFORMATION: "CYD4 prmE"
<220> FEATURE:
<223> OTHER INFORMATION: CYD4 prmE

<400> SEQUENCE: 4

| | | | | | |
|---|---|---|---|---|---|
| uuucaccugu | caacaagaga | cggcgaaccc | cucaugauag | uggcaaaaca | cgaaaggggg | 60 |
| agaccucucu | uguuuaagac | aacagaggga | aucaacaaau | gcacucuuau | ugccauggac | 120 |
| cugggugaaa | ugugugaaga | cacuguuacg | uauaaaugcc | cucuacuggu | uaacaccgaa | 180 |
| ccugaagaca | uugauugcug | gugcaaucuc | acguccaccu | gggucaugua | cgggacaugu | 240 |
| acccagagcg | gagaacggag | acgagagaag | cgcucaguag | cuuuaacacc | acauucagga | 300 |
| augggauugg | aaacaagagc | ugagacaugg | augucaucgg | aagggcuug | gaaacaugcu | 360 |
| caaagaguag | aaagcuggau | acucagaaac | ccaggauucg | cgcucuuggc | aggauuuaug | 420 |
| gcuuacauga | uugggcaaac | aggaauucag | cgaacugucu | ucuuugccu | aaugaugcug | 480 |
| gucgccccau | ccuacggaau | gcgaugcgua | ggaguaggga | acagagacuu | uguggaagga | 540 |
| gucucggug | gagcaugggu | cgaccuggug | cuggaacaug | gaggaugcgu | cacaaccaug | 600 |
| gcccagggaa | aaccaaccuu | ggauuuugaa | cugaccaaga | caacagccaa | ggaaguggcu | 660 |
| cuacuucgaa | ccuauugcau | ugaagccucg | auaucaaaca | uaaccacggc | aacaagaugu | 720 |
| ccaacgcaag | gagagccuua | ucucaaagag | gaacaagacc | aacaguacau | uugccggaga | 780 |
| gaugugguag | acagagggug | gggcaauggc | uguggcuuau | uggaaaagg | aggaguugug | 840 |
| acaugugcga | aguuuuuaug | ucgggggaag | auaacaggca | aucggucca | aauugaaaac | 900 |
| cuugaauaua | cagugguugu | gacaguccac | aauggagaca | cccaugcagu | aggaaaugac | 960 |
| acaucuaauc | auggagugac | agccacgaua | acucccaggu | caccaucggu | agaaguuaaa | 1020 |
| uugccggacu | auggagaacu | aacacucgau | ugugaaccca | ggucggaau | ugauuucaau | 1080 |
| gagaugauuc | ugaugaaaau | gaaaagaaa | acguggcuug | ugcauaagca | augguuuug | 1140 |
| gaccuaccuc | uaccauggac | agcaggagca | gacacaucag | aaguccauug | gaauuacaaa | 1200 |
| gagagaaugg | ugacauucaa | gguuccucau | gccaagagac | aggaugugac | agucuagga | 1260 |
| ucucaggagg | gagcuaugca | uucugcccuc | gccgagcca | cagaagugga | uuccggugau | 1320 |
| ggaaaucaca | uguuugcagg | acaucucaag | ugcaaaaguc | cguaggagaa | auugagaauu | 1380 |
| aaaggaaugu | cauacacaau | guguucagga | aaguucucaa | uugacaaaga | gauggcagaa | 1440 |
| acacagcaug | ggacaacagu | ggugaaaguc | aaguaugaag | gcgcuggagc | uccguguaaa | 1500 |
| gucccccauag | agauaagaga | ugugaacaag | gaaaagugg | uugggcgcau | caucucaucu | 1560 |
| accccuuuug | cugagaauac | caacagcgua | accaacauag | aauuagaacc | cccuuuuggg | 1620 |
| gacaguuaca | uagugauagg | uguuggagau | agugcauuaa | cacuccauug | guucaggaaa | 1680 |
| gggagcucca | uuggcaagau | guuugagucc | acauacagag | gugcaaaacg | aauggccauu | 1740 |
| cuaggugaaa | cagcuuggga | uuuugguucu | guggugggaa | uguucacauc | acugggaaag | 1800 |
| gcuguacacc | agguuuuugg | aagugugauu | acaaccaugu | uggaggggu | cucauggaug | 1860 |
| guuagaaucc | uaauugggu | cuuaguauug | uggauuggca | cgaauucaag | aaacacuuca | 1920 |
| auggcaauga | cgugcauagc | uguuggagga | aucacucugu | uucuagguuu | cacaguuggc | 1980 |
| gcc | | | | | | 1983 |

<210> SEQ ID NO 5
<211> LENGTH: 1983
<212> TYPE: RNA
<213> ORGANISM: artificial sequences
<223> OTHER INFORMATION: "CYD2V prmE"
<220> FEATURE:
<223> OTHER INFORMATION: CYD2V prmE

<400> SEQUENCE: 5

| | | | | | | |
|---|---|---|---|---|---|---|
| uuccauuuaa | ccacacgaaa | uggagaacca | cacaugaucg | uuggcagaca | agagaaaggg | 60 |
| aaaagccuuc | uguuuaaaac | agaggauggu | gugaacaugu | guacccucau | ggccauugau | 120 |
| cuuggugaau | ugugugaaga | uacaaucacg | uacaagugcc | cccuccucag | gcagaaugaa | 180 |
| ccagaagaua | uagauuguug | gugcaacucc | acguccacau | ggguaacuua | ugggacugu | 240 |
| accaccacag | gagaacacag | aagagaaaaa | agaucagugg | cacucguucc | acauguggu | 300 |
| augggacugg | agacacgaac | ugaaacaugg | augucgucag | aagggccug | gaaacacgcu | 360 |
| cagagaauug | aaacuuggau | cuugagacau | ccaggcuuua | ccauaauggc | agcaauccug | 420 |
| gcauauaccg | uaggaacgac | acauuccaa | agggcccuga | uuucaucuu | acuggcagcu | 480 |
| gucgcuccuu | caaugacaau | gcguugcaua | ggaauaucaa | auagagacuu | uguagaaggg | 540 |
| guuucaggag | gaagcugggu | ugacauaguc | uuagaacaug | gaaguugugu | gacgacaaug | 600 |
| gcaaaaaaua | aaccaacacu | ggauuuugaa | cugauaaaaa | cagaagccaa | acaaccugcc | 660 |
| acucuaagga | aguacuguau | agaggcaaag | cugaccaaua | caacaacaga | aucucguugc | 720 |
| ccaacacaag | gggaacccag | ucuaaaugaa | gagcaggaca | aaagguucgu | cugcaaacac | 780 |
| uccauggauag | acagaggaug | gggaaaugga | uguggauuau | uggaaagggg | aggcauugug | 840 |
| accugugcua | uguucacaug | caaaaagaac | auggaaggaa | aaaucgugca | accagaaaau | 900 |
| uuggaauaca | ccaucgugau | aacaccucac | ucaggagaag | agcacgcugu | agguaaugac | 960 |
| acaggaaaac | augauaagga | aauuaaaaua | acaccacaga | guuccaucac | agaagcagaa | 1020 |
| cugacaggcu | auggcacagu | cacgauggag | ugcucuccga | gaacgggccu | ugacuucaau | 1080 |
| gagauggugc | ugcugcagau | ggaagauaaa | gcuggcugg | ugcacaggca | augguccua | 1140 |
| gaccugccgu | uaccauggcu | acccggagcg | gacacacaag | gaucaaauug | gauacagaaa | 1200 |
| gagacauugg | ucacuuucaa | aaaucccac | gcgaagaagc | aggaugucgu | uguuuagga | 1260 |
| ucucaagaag | gagccaugca | cacggcacuc | acagggggcca | cagaauccca | gaugucauca | 1320 |
| ggaaacuuac | uauucacagg | acaucucaaa | ugcaggcuga | aauggacaa | acuacagcuc | 1380 |
| aaaggaaugu | cauacucuau | guguacagga | aaguuuaaaa | uugugaagga | aauagcagaa | 1440 |
| acacaacaug | gaacaauagu | uaucagagua | caauaugaag | gagacggcuc | uccauguaag | 1500 |
| aucccuuuug | aaauaaugga | uuuggaaaaa | agacauguccu | uaggucgccu | gauuacaguu | 1560 |
| aauccgaucg | uaacagaaaa | agauagccca | gucaacauag | aagcagaacc | uccauucgga | 1620 |
| gacagcuaca | ucauuauagg | aguagagccg | gacaauuga | aacucaacug | guucaagaaa | 1680 |
| ggaaguucca | ucggccaaau | guuugagacg | acaaugagag | gagcaaagag | aauggccauu | 1740 |
| uuagguugaca | cagccuggga | uuuuggaucu | cugggaggag | uguuuacauc | uauaggaaag | 1800 |
| gcucuccacc | aaguuucgg | agcaaucuau | ggggcugccu | uuaguggggu | ucauggacu | 1860 |
| augaaaaucc | ucauaggagu | caucaucaca | uggauaggaa | ugaauucacg | uagcaccuca | 1920 |
| cugucugugu | cacuaguauu | ggugggaauc | auaacacugu | acuuggagc | uaugggucag | 1980 |
| gcu | | | | | | 1983 |

<210> SEQ ID NO 6
<211> LENGTH: 10735
<212> TYPE: RNA
<213> ORGANISM: artificial sequences
<223> OTHER INFORMATION: "VDV1"
<220> FEATURE:
<223> OTHER INFORMATION: VDV1

<400> SEQUENCE: 6
aguuguuagu cuacguggac cgacaagaac aguuucgaau cggaagcuug cuuaacguag 60
uucuaacagu uuuuuauuag agagcagauc ucugaugauc aaccaacgaa aaaagacggg 120
ucgaccgucu uucaauaugc ugaaacgcgc gagaaaccgc gugucaacug uuucacaguu 180
ggcgaagaga uucucaaaag gauugcucuc aggccaagga cccaugaaau uggugauggc 240
uuucauagca uucuuaagau uucuagccau acccccaaca gcaggaauuu uggcuagaug 300
gggcucauuc aagaagaaug gagcgauuaa aguguuacgg gguuucaaga gagaaaucuc 360
aaacaugcua aacauaauga acaggaggaa aagauccgug accaugcucc uuaugcugcu 420
gcccacagcc cuggcguucc aucugacgac acgagggga gagccgcaua ugauaguuag 480
caagcaggaa agaggaaagu cacuuuuguu caagaccucu gcaggguguca acaugugcac 540 ccucauugcg auggauuugg gagaguugug ugaggacacg augaccuaca aaugcccccg 600
gaucacugag gcggaaccag augacguuga cuguuggugc aaugccacgg acacaugggu 660
gaccuaugga acgugcucuc aaacuggcga acaccgacga gacaaacguu ccgucgcauu 720
ggccccacac guggggcuug gccuagaaac aagagccgaa acguggaugu ccucugaagg 780
ugcuuggaaa cagauacaaa aaguagagac uugggcucug agacauccag gauucacggu 840
gauagcccuu uuucuagcac augccauagg aacauccauc acccagaaag ggaucauuuu 900
cauuuugcug augcugguaa caccaucuau ggccaugcga ugcguggga uaggcaacag 960 agacuucgug gaaggacugu caggagcaac augggugau gugguacugg agcauggaag 1020
uugcgucacc accauggcaa aaaacaaacc aacacuggac auugaacucu ugaagacgga 1080
ggucacaaac ccugcaguuc ugcguaaauu gugcauugaa gcuaaaaauau caaacaccac 1140 caccgauucg agauguccaa cacaaggaga agccacacug guggaagaac aagacgcgaa 1200
cuuugugugc cgacgaacgu ucguggacag aggcuggggc aauggcugug ggcuauucgg 1260
aaaagguagu cuaauaacgu gugccaaguu uaagugugug acaaaacuag aaggaaagau 1320
agcucaauau gaaaaccuaa aauauucagu gauagucacc guccacacug gagaucagca 1380 ccaggugga aaugagacua cagaacaugg aacaacugca accauaacac cucaagcucc 1440
uacgucggaa auacagcuga ccgacuacgg aacccuuaca uuagauuguu caccuaggac 1500
agggcuagau uuuaacgaga uggguguugcu gacaaugaaa aagaaaucau ggcuugucca 1560
caaacagugg uuucuagacu uaccacugcc uuggaccucu ggggcuuuaa caucccaaga 1620
gacuuggaac agacaagauu uacuggucac auuuaagaca gcucaugcaa agaagcagga 1680
aguagucgua cuaggaucac aagaaggagc aaugcacacu gcgcugacug gagcgacaga 1740
aauccaaacg ucaggaacga caacaauuuu cgcaggacac cuaaaaugca gacuaaaaau 1800
ggacaaacua acuuuaaaag ggaugucaua ugugaugugc acaggcucau ucaaguuaga 1860
gaaagaagug gcugagaccc agcauggaac uguucuggug cagguuaaau augaaggaac 1920
agacgcacca ugcaagauuc ccuuuucgac ccaagaugag aaaggagcaa cccagaaugg 1980
gagauuaaua acagccaacc ccauagucac ugacaaagaa aaaccaguca auauugaggc 2040

-continued

```
agaaccaccc uuuggugaga gcuacaucgu gguaggagca ggugaaaaag cuugaaacu      2100 aagcugguuc aagaaaggaa gcagcauagg gaaaauguuu gaagcaacug cccgaggagc     2160
acgaaggaug gccauucugg gagacaccgc augggacuuc gguucuauag gaggaguguu     2220
cacgucuaug ggaaaacugg uacaccaggu uuuuggaacu gcauauggag uuuuguuuag     2280
cggaguuucu uggaccauga aaauaggaau agggauucug cugacauggc uaggauuaaa     2340
uucaaggaac acgucccuuu cggugaugug caucgcaguu ggcauggucA cacuguaccu     2400
aggagucaug guucaggcag auucgggaug uguaaucaac uggaaaggca gagaacuuaa     2460 augugggaagc ggcauuuuug ucacuaauga aguucacacu uggacagagc aaucaaaauu    2520
ccaggcugac uccccaaga gacuaucagc agccauggg aaggcauggg aggagggugu      2580
guguggaauc cgaucagcca cucgucucga gaacaucaug uggaaacaaa uaucaaauga    2640
auugaaccac auccuacuug aaaaugacau gaaauuuaca gggucgugg gagacguuag    2700 uggaaucuug gcccaaggaa aaaaaaugau uaggccacaa cccauggaac acaaauacuc    2760
guggaaaagc uggggaaaag cuaaaaucau aggagcggau uacagaaaca ccaccuucau    2820
caucgacggc ccaaacaccc cagaaugccc ugacaaucaa agagcaugga uauuuggga    2880 aguagaggac uauggauuug ggauuuucac gacaaacaua uugaauu gcgugacuc      2940 cuacacccaa guaugugacc accggcugau gucagcugcc auuaaggaca gcaaggcagu   3000
ccaugcugac auggguacu ggauagaaag ugaaagaac gagacaugga aguuggcgag    3060
agccuccuuu auagaaguua agacaugcau cuggccaaaa ucccacacuc uauggagcaa   3120
uggaguucug gaaagugaaa ugauaauucc aaagauauau ggaggaccaa uaucucagca   3180
caacuacaga ccaggauauu ucacacaaac agcagggccg uggcaccuag gcaaguugga   3240
acuagauuuc gauuuuugug aagguaccac aguguugug gaugaacauu uggaaaucg    3300 aggaccaucu cucagaacca acagucac aggaaagaua auccaugaau ggugcugcag    3360
aucuuguacg cuaccccccc uacguuucaa aggggaagac ggguguuggu acggcaugga   3420
aaucagacca gugaaggaca aggaagagaa ccuggucaag ucaauggucu cugcagggu c  3480 aggagaagug gacagcuuuu cacuaggacu gcuaugcaua ucaauaauga uugaagaagu   3540
gaugagaucc agauggagca aaaaaaaugcu gaugacugga acacuggcug uguuccuccu   3600
ucuuauaaug ggacaauuga cauggaguga ucugaucagg uuauguauua ugguggagc    3660 caacgcuuca gacaagauga ggaugggaac aacguaccua gcuuuaaugg ccacuuucaa   3720
aaugagacca auguucgccg ucgggcuauu auuucgcaga cuaacaucua gagaaguucu   3780
ucuucuuaca auuggcuuga gccuggugc auccguggag cuaccaaguu cccuagagga   3840 gcuggggau ggacuugcaa uaggcaucau gaugugaaaau uauugacug auuuucaguc    3900 acaccagcua ugggcuacuc ugcuauccuu gacauuuauu aaaacaacuu uucauugca    3960 cuaugcaugg aagacaaugg cuaugguacu gcaauuguua ucuucuuccc cuuuaugccu   4020
guccacgacc ucucaaaaaa caacauggcu uccggugcug uugggaucuc uuggaugcaa   4080
accacuaccc auguucuuua acagaaaa caaaaucugg ggaaggaaga guuggcccu    4140 caaugaagga auuauggcug uuggaauagu uaguauucua cuaaguucac uuuuaaaaaa   4200
ugaugugccg cuagccggcc cauuaauagc uggaggcaug cuaauagcau guuaugucau   4260
auccggaagc ucagcugauu uaucacugga gaaagcggcu gaggucuccu ggaggaaga   4320 agcagaacac ucaggcgccu cacacaacau acuaguagag guucaagaug auggaaccau   4380
gaagauaaaa gaugaagaga gagaugacac gcucaccauu cuccuuaaag caacucugcu   4440
```

```
ggcagucuca gggguguacc caaugucaau accagcgacc cuuuugugu gguauuuuug    4500 gcagaaaaag aaacagagau caggagugcu augggacaca cccagccccc cagaagugga    4560
aagagcaguu cuugaugaug gcaucuauag aauuuugcaa agaggacugu ugggcagguc    4620
ccaaguagga guaggaguuu uccaagaagg cguguccac acaaugugg acgucacuag      4680 gggagcuguc cucauguauc aaggaaaaag gcuggaacca agcugggcca gugucaaaaa    4740
agacuugauc ucauauggag gagguugag guuucaagga uccuggaaca cgggagaaga    4800
aguacaggug auugcuguug aaccgggaaa aaaccccaaa aaugua caaa caacgccggg    4860 uaccuucaag accccugaag gcgaaguugg agccauagcc uuagacuuua aaccuggcac    4920
aucuggaucu cccaucguaa acagagaggg aaaaauagua ggucuuuaug gaauggagu     4980 ggugacaaca agcggaacuu acguuagugc cauagcucaa gcuaaggcau acaagaagg     5040 gccucuacca gagauugagg acaaggguu uaggaaaaga aacuuaacaa uaauggaccu     5100
acauccagga ucgggaaaaa caagaagaua ccuuccagcc auaguccgug aggccauaaa    5160
aaggaagcug cgcacgcuaa uccagcucc cacaagaguu gucgcuucug aaauggcaga    5220
ggcacucaag ggagugccaa uaagguauca gacaacagca gugaagagug aacacacagg    5280
aaaggagaua guugaccuua ugugccacgc cacuuucacc augcgccucc ugucucccgu    5340
gagaguuccc aauuauaaca ugauuaucau ggaugaagca cacuucaccg auccagccag    5400
cauagcagcc agagggaca ucucaaccocg agugggua ugggugaagcag cugcgaucuu    5460 uaugacagcc acuccccag gaucggugga ggccuuucca cagagcaaug caauuauccc     5520
agaugaggaa agagacauuc cugagagauc auggaacuca ggcuaugacu ggaucacuga    5580
uuuuccaggu aaaacagucu gguuugucc aagcaucaaa ucaggaaaug acauugccaa     5640
cuguuuaaga aaaaacggga acgggugau ccaauugagc agaaaaaccu uugacacuga     5700
guaccagaaa acaaaaaaca acgacuggga cuaugucguc acaacagaca uuuccgaaau     5760
gggagcaaau uucgggccg acagggua au agacccaagg cggugucuga aaccgguaau    5820
acuaaaagau ggucagagc gcgucauucu agcggaccg augccaguga cugugggccag    5880 ugccgcccag aggagagagaa gaauuggaag gaaccaaaac aaggaggug aucaguauau    5940 uuacauggga cagccuuuaa aaaugauga ggaccacgcu cauggacag aagcaaagau     6000 gcuccuugac aauauaaaca caccagaagg gauuauccca gcccucuuug agccggagag    6060
agaaaagagu gcagcuauag acggggaaua cagacugcgg ggugaagcaa ggaaaacguu    6120 cgggagcuc augagaagag gggaucuacc agucuggcua uccacaaag uugccucaga     6180 aggcuuccag uacuccgaca aaggugguug cuucgauggg aaaggaaca accaggugu     6240 ggaggagaac auggacgugg agaucuggac aaaagaagga gaaagaaga acuacgacc     6300 ucgcugguug gacgccagaa cauacucuga cccacuggcu cugcgcgagu uuaagaguu     6360 ugcagcagga agaagagcg ucucaggua ccuaauauua gaauaggga acuuccaca      6420 acauuugacg caaagggccc agaaugcuuu ggacaacuug ucauguugc acaauuccga    6480 acaaggagga aaagccuaua gacaugcuau ggaagaacug ccagacacaa uagaaacguu    6540
gaugcuccua gccuugauag cuguuugac uggguggagu acgcguucu ccuaucagg      6600 aagaggucua ggaaaaacau cuaucggcuu acucugcgug auggccucaa gcgcacuguu    6660 auggaugcc agugugga gc cccauuggau agcggccucc aucauacug g aguucuuucu    6720 gaugguacug cuuauuccag agccagacag acagcgcacu ccacaggaca accagcuagc    6780
```

-continued

```
auauguggug auaggucugu uauucgugau auugacagug gcagccaaug agaugggauu   6840
auuggaaacc acaaagaaag accuggggau uggccaugua gcugcugaaa accaccacca   6900
ugcuacaaug cuggacguag accuacaucc agcuucagcc uggacccucu augcaguggc   6960
cacaacaauc aucacuccua ugaugagaca cacaauugaa aacacaacgg caaauauuuc   7020
ccugacagcc aucgcaaacc aagcagcuau auugaugggg cuugacaagg gauggccaau   7080
aucgaagaug gacauaggag uuccacuucu cgccuugggg ugcuauuccc aagugaaucc   7140
gcugacacug auagcggcag uauugaugcu aguagcucau uacgccauaa uuggaccugg   7200
acugcaagca aaagcuacua gagaagcuca aaaagaaca gcggcuggaa uaaugaaaaa   7260
uccaacuguc gacgggauug uugcaauaga cuuagauccc gugguuuacg augcaaaauu   7320
ugaaaaacag cuaggccaaa uaauguuguu gauacuuugc acaucacaga uucuuuugau   7380
gcggacuaca ugggccuugu gugaauccau cacauuggcu acuggaccuc ugaccacucu   7440 uugggagggga ucccaggaa aauucuggaa caccacaaua gcgguaucca uggcaaacau   7500 uuucagggggg aguuaucuag caggagcagg ucuggccuuc ucauuaauga aaucucuagg   7560
aggagguagg agaggcacgg gagcccaagg ggaaacacug ggagaaaaau ggaaaagaca   7620
acuaaaccaa cugagcaagu cagaauuucaa uacuuacaag aggagugggga uuauggaggu   7680 ggauagaucc gaagccaaag agggacugaa agaggagaa acaaccaaac acgcaguauc   7740
gagaggaacg gccaaacuga ggugguucgu ggagaggaac cuugugaaac cagaagggaa   7800
agucauagac cucgguugug aagaggugg cuggucauau uauugcgcug ggcugaagaa   7860
agucacagaa gugaaaggau acacaaaagg aggaccugga caugaggaac caauccaaau   7920
ggcgaccuau ggauggaacc uaguaaggcu gcacuccgga aaagauguau uuuuauacc   7980 accugagaaa ugugacaccc uuugugguga uauuggugag uccucuccga acccaacuau   8040
agaggaagga agaacguuac guguucugaa auggguggaa ccauggcuca gaggaaacca   8100
auuuugcaua aaaauucaa aucccuauau gccgagcgug uagaaaacuc uggaacaaau   8160
gcaaagaaaa cauggaggaa ugcuagugcg aaacccacuc ucaagaaauu ccacccauga   8220
aauguacugg guucaugug gaacaggaaa cauugugca gcaguaaaca ugacaucuag   8280
aauguugcua aaucgguuca caauggcuca caggaagcca acauaugaaa gagacguggga   8340 cuuaggcgcu ggaacaagac auggccagu agaaccagag guagccaacc uagauaucau   8400
uggccagagg auagagaaua uaaaaaauga acauaaguca acauggcauu augaugagga   8460 caaucccauac aaaacauggg ccuaucaugg aucauaugag guuaagccau caggaucggc   8520
cucauccaug gucaauggcg uggugagauu gcucaccaaa ccaugggaug uuaucccau   8580 ggucacacaa auagccauga cugauaccac accccuuuga caacagagggg uguuuaaaga   8640 gaaaguugac acgcgcacac caaaagcaaa acguggcaca gcacaaauua uggaagugac   8700
agccaggugg uuauggggguu uccuuucuag aaacaaaaaa cccagaauuu gcacaagaga   8760
ggaguuuaca agaaaaguua ggucaaacgc agcuauugga gcaguuucg uugaugaaaa   8820 ucaauggaac ucggcaaaag aagcagugga agacgaacgg uucuggaac uuguccacag   8880 agagagggag cuucauaaac aggggaaaug ugccacugu gucuacaaua ugaugggaa   8940 gagagagaaa aaauuaggag aguucggaaa ggcaaaagga agucgugcaa uagguacau   9000 guguuuggga gcacgcuucc uagaguuuga agcccuuggu ucaugaaug aagaucacug   9060 guucaguaga gagaauucac ucaguggagu ggaaggagaa ggacuccaca aacuuggaua   9120
cauacucaga gacauaucaa ggauuccagg ggggaacaug uaugcagaug acacagccgg   9180
```

-continued

```
augggacaca agaauaacag aggaugaucu ccagaaugag gcuaaaauca cugacaucau   9240
ggagcccgaa caugcccugc uggcuacguc aaucuuuaag cugaccuacc aaaauaaggu   9300
gguaagggug cagagaccag caaaaaaugg aaccgugaug gauguuauau ccagacguga   9360
ccagagaggc aguggacagg uuggaacuua uggcuuaaac acuuucacca acauggaggc   9420
ccaacugaua agacaaaugg agucugaggg aaucuuuuua cccagcgaau uggaaacccc   9480
aaaucuagcc ggaagaguuc ucgacugguu ggaaaaauau ggugucgaaa ggcugaaaag   9540
aauggcaauc agcggagaug acugugugu gaaaccaauu gaugacaggu ucgcaacagc   9600
cuuaacagcu uugaaugaca ugggaaaagu aagaaaagac auaccacaau gggaaccuuc   9660
aaaaggaugg aaugauuggc aacaagugcc uuucuguuca caccacuucc accagcuaau   9720
uaugaaggau gggagggaga uaguggugcc augccgcaac caagaugaac uuguggggag   9780
ggccagagua ucacaaggcg ccggauggag ccugagagaa accgcaugcc uaggcaaguc   9840
auaugcacaa auguggcagc ugauguauuu ccacaggaga gaccugagac uggcggcuaa   9900
cgcuauuugu ucagccguuc caguugauug gguccaaacc agccgcacca ccuggucgau   9960
ccaugcccau caccaaugga ugacaacaga agacauguua ucaguaugga auagggucug  10020
gauagaggaa aacccaugga uggaggauaa gacucaugug uccaguuggg aagaaguucc  10080
auaccuagga aagagggaag aucaguggug uggaucccug auaggcuuaa cagcaagggc  10140
caccugggcc acuaauauac aaguggccau aaaccaagug agaaggcuca uugggaauga  10200
gaauuaucua gauuacauga caucaaugaa gagauucaag aaugagagug aucccgaagg  10260
ggcacucugg uaagucaaca cauucacaaa auaaaggaaa auaaaaaauc aaaugaggca  10320
agaagucagg ccagauuaag ccauaguacg guaagagcua ugcugccugu gagccccguc  10380
caaggacgua aaaugaaguc aggccgaaag ccacgguuug agcaagccgu gcugccugug  10440
gcuccaucgu ggggauguaa aaacccggga ggcugcaacc cauggaagcu guacgcaugg  10500
gguagcagac uagugguuag aggagacccc ucccaagaca caacgcagca gcggggccca  10560
acaccagggg aagcuguacc cugguggua ggacuagagg uuagaggaga cccccgcgu   10620 aacaauaaac agcauauuga cgcugggaga gaccagagau ccugcugucu cuacagcauc  10680
auuccaggca cagaacgcca gaaaauggaa uggugcuguu gaaucaacag guucu       10735
```

<210> SEQ ID NO 7
<211> LENGTH: 10723
<212> TYPE: RNA
<213> ORGANISM: artificial sequences
<223> OTHER INFORMATION: "VDV2"
<220> FEATURE:
<223> OTHER INFORMATION: VDV2

<400> SEQUENCE: 7

```
aguuguuagu cuacguggac cgacaaagac agauucuuug agggagcuaa gcucaaugua     60
guucuaacag uuuuuuaauu agagagcaga ucucugauga auaaccaacg gaaaaaggcg    120
aaaaacacgc cuuucaauau gcugaaacgc gagagaaacc gcgugucgac ugugcaacag    180
cugacaaaga gauucucacu uggaaugcug cagggacgag gaccauuaaa acuguucaug    240
gcccuggugg cguuccuucg uuuccuaaca aucccaccaa cagcagggau auugaagaga    300
uggggaacaa uuaaaaaauc aaaagcuauu aauguuuuga gaggguucag gaaagagauu    360
ggaaggaugc ugaacaucuu gaauaggaga cgcagaucug caggcaugau cauuaugcug    420
auuccaacag ugauggcguu ccauuuaacc acacguaacg gagaaccaca caugaucguc    480
```

```
agcagacaag agaaagggaa aagucuucug uuuaaaacag agguuggcgu gaacaugugu    540
acccucaugg ccauggaccu uggugaauug ugugaagaca caaucacgua caagugsccc    600
cuucucaggc agaaugagcc agaagacaua gacuguuggu gcaacucuac guccacgugg    660
guaacuuaug ggacguguac caccauggga gaacauagaa gagaaaaaag aucaguggca    720
cucguuccac augugcgaau gggacuggag acacgaacug aaacauggau gucaucagaa    780
ggggccugga aacaugucca gagaauugaa acuggaucu ugagcaucc aggcuucacc     840 augauggcag caauccuggc auacaccaua ggaacgacac auuccaaag agcccugauu    900 uucaucuuac ugcagcugu cacuccuuca augacaaugc guugcauagg aaugucaaau    960
agagacuuug uggaaggggu ucaggagga agcuggguug acauagucuu agaacaugga    1020
agcuguguga cgacgauggc aaaaaacaaa ccaacauugg auuugaacu gauaaaaaca    1080 gaagccaaac agccugccac ccuaaggaag uacuguauag aggcaaagcu aaccaacaca    1140
acaacagaau cucgcugccc aacacaaggg gaacccagcc uaaaugaaga gcaggacaaa    1200
agguucgucu gcaaacacuc caugguagac agaggauggg gaaauggaug uggacuauuu    1260
ggaaagggag gcauugugac cugugcuaug uucagaugca aaaagaacau ggaaggaaaa    1320
guugugcaac cagaaaacuu ggaauacacc auugugauaa caccucacuc aggggaagag    1380
caugcagucg aaaugacac aggaaaacau ggcaaggaaa ucaaaauaac accacagagu    1440
uccaucacag aagcagaauu gacagguuau ggcacuguca caaggagug cucuccaaga    1500 acgggccucg acuucaauga gaugguguug cugcagaugg aaaauaaagc uuggcuggug    1560
cacaggcaau gguccuaga ccugccguua ccaugguugc ccggagcgga cacacaagag    1620
ucaaauugga uacagaagga gacauugguc acuuucaaaa auccccaugc gaagaaacag    1680
gauguuguug uuuuaggauc ccaagaaggg gccaugcaca cagcacuuac aggggccaca    1740
gaaauccaaa ugucaucagg aaacuuacuc uucacaggac aucucaagug caggcugaga    1800
auggacaagc uacagcucaa aggaaugcca uacucuaugu gcacaggaaa guuuaaaguu    1860
gugaaggaaa uagcagaaac acaacaugga acaauaguua ucagagugca auaugaaggg    1920
gacggcucuc caugcaagau cccuuuugag auaauggauu uggaaaaaag acaugucuua    1980
ggucgccuga uuacagucaa cccaauugug acagaaaaag auagcccagu caacauagaa    2040
gcagaaccuc cauuuggaga cagcuacauc aucauagaga uagagccggg acaacugaag    2100
cucaacuggu uuaagaaagg aageueuauc ggecaaaugu uuagacaac aaugagggg    2160 gcgaagagaa uggccauuuu aggugacaca gccuggauu uggauccuu ggaggagug    2220 uuuacaucua aggaaggc ucuccaccaa gucuuggag caaucuaugg agcugccuuc    2280
agugggguuu caugacuau gaaaauccuc auaggaguca uuaucacaug gauaggaaug    2340
aauucacgca gcaccucacu gucugugaca cuaguauugg ugggaauugu gacacuguau    2400
uugggaguca uggugcaggc cgauaguggu ugcguuguga gcugaaaaaa caaagaacug    2460 aaaugugcgca gugggauuuu caucacagac aacgugcaca caugggacaga acaauacaaa    2520 uccaaccag aauccccuuc aaaacuagcu ucagcuaucc agaaagccca ugaagaggac    2580
auuuguggaa uccgcucagu aacaagacug gagaaucuga uguggaaaca aauaaccaca    2640
gaauugaauc acauucuauc agaaaaugag gugaaguaa cuauuaugac aggagacauc    2700
aaaggaauca ugcaggcagg aaaacgaucu cucggccuc agcccacuga gcugaaguau    2760
ucauggaaaa caugggcaa agcaaaaaug cucucuacag agucucauaa ccagaccuuu    2820
```

```
cucauugaug gccccgaaac agcagaaugc cccaacacaa auagagcuug gaauucguug   2880
gaaguugaag acuauggcuu uggaguauuc accaccaaua uauggcuaaa auugaaagaa   2940
aaacaggaug uauucugcga cucaaaacuc augucagcgg ccauaaaaga caacagagcc   3000
guccaugccg auaugggulua uuggauagaa agugcacuca augacacaug gaagauagag   3060
aaagccucuu ucauugaagu uaaaaacugc cacuggccaa aaucacacac ccucuggagc   3120
aauggagugc uagaaaguga gaugauaauu ccaaagaauc ucgcuggacc agugucucaa   3180
cacaacuaua gaccaggcua ccauacacaa auaacaggac cauggcaucu agguaagcuu   3240
gagauggacu uugauuucug ugauggaaca acaguggulag ugacuagga cugcggaaau    3300 agaggacccu cuuugagaac aaccacugcc ucggaaaac ucauaacaga auggugcugc     3360
cgaucuugca cauuaccacc gcuaagauac agaggugagg augggugcug guacgggaug   3420
gaaaucagac cauugaagga gaaagaagag aauuugguca acuccuuggu cacagcugga   3480
cauggcaggu cgacaacuuu ucacuaagga gucuugggaa uggcauuguu ccuggaggaa   3540
augcuuagga cccgaguagg aacgaaacau gcaauacuac uaguugcagu ucuuuugug    3600 acauugauca cagggaacau guccuuuaga gaccugggaa gagugauggu uaugguaggc   3660 gccacauga cggaugacau agguaugggc gugacuuauc uugcccuacu agcagccuuc     3720
aaagucagac caacuuuugc agcuggacua cucuugagaa agcugaccuc caaggaauug   3780
augaugacua cuauaggaau uguacuccuc ucccagagca ccauaccaga gaccauucuu   3840
gaguugacug augcguuagc cuuaggcaug augguccuca aaauggugag aaauauggaa   3900
aaguaucaau uggcagugac uaucauggcu aucuugugcg ucccaaacgc agugauauua   3960
caaaacgcau ggaaagugag uugcacaaua uuggcagugg uguccguuuc cccacuguuc   4020
uuaacauccu cacagcaaaa aacagauugg auaccauuag cauugacgau caaaggcuc    4080 aauccaacag cuauuuuucu aacaaccccuc ucaagaacca gcaagaaaag gagcuggcca   4140
uuaaaugagg cuaucauggc agucggggaug gugagcauuu uagccaguuc ucuccuaaaa   4200
aaugauauuc ccaugacagg accauuagug gcuggagggc uccucacugu gugcuacgug   4260
cucacuggac gaucggccga uuuggaacug gagagagcag ccgaugucaa augggaagac   4320
caggcagaga uaucaggaag caguccaauc cugucaauaa caauaucaga gaugguagc    4380 augucgauaa aaaugaaga ggaagaacaa acacugacca uacucauuag aacaggauug    4440
cuggugaucu caggacuuuu uccuguauca auaccaauca cggcagcagc augguaccug   4500
ugggaaguga gaaacaacg ggccggagua uugugggaug uuccuucacc cccacccaug     4560
ggaaaggcug aacuggaaga uggagccuau agaauuaagc aaaaagggau ucuuggauau   4620
ucccagaucg gagccggagu uuacaaagaa ggaacauucc auacaaugug gcaugucaca   4680
cguggcgcug uucuaaugca uaaaggaaag aggauugaac caacauggggc ggacgucaag   4740 aaagaccuaa uaucauaugg aggaggcugg aaguuagaag gagaauggaa ggaaggagaa   4800 gaguccagg uauggcacu ggagccugga aaaaauccaa gagccgucca aacgaaaccu     4860
ggucuuuuca aaccaacgc cggaacaaua ggugcuguau cucuggacuu uucuccugga   4920
acgucaggau cuccaauuau cgacaaaaaa ggaaaaguug ugggucuuua gguaauggu   4980 guuguuacaa ggaguggagc auaugugagu gcuauagccc agacugaaaa aagcauugaa   5040
gacaacccag agaucgaaga ucacauuuuc cgaaagagaa gacugaccau cauggaccuc   5100
cacccaggag cgggaaagac gaagagauac cuuccggcca uagucagaga agcuauaaaa   5160 cggggguuuga gaacauuaau cuuggcccccc acuagaguug uggcagcuga aauggaggaa   5220
```

```
gcccuuagag gacuuccaau aagauaccag accccagcca ucagagcuga gcacaccggg    5280
cgggagauug uggaccuaau gugucaugcc acauuuacca ugaggcugcu aucaccaguu    5340
agagugccaa acuacaaccu gauuaucaug gacgaagccc auuucacaga cccagcaagu    5400
auagcagcua gaggauacau cucaacucga guggagaugg gugaggcagc ugggauuuuu    5460
augacagcca ucccccgggg aagcagagac ccauuuccuc agagcaaugc accaaucaua    5520
gaugaagaaa gagaaauccc ugaacgcucg uggaauuccg gacaugaaug ggucacggau    5580
uuuaaaggga agacuguuug guucguucca aguauaaaag caggaaauga uauagcagcu    5640
ugccugagga aaaauggaaa gaaagugaua caacucagua ggaagaccuu ugauucugag    5700
uaugucaaga cuagaaccaa ugauugggac uucgugguua caacugacau uucagaaaug    5760
ggugccaauu ucaaggcuga gagguuuaua daccccagac gcugcaugaa accagucaua    5820
cuaacagaug gugaagagcg ggugauucug gcaggaccua ugccagugac ccacucuagu    5880
gcagcacaaa aagagggag aauaggaaga aauccaaaaa augagaauga ccaguacaua    5940
uacauggggg aaccucugga aaaugaugaa gacugugcac acuggaaaga agcuaaaaug    6000
cuccuagaua acaucaacac gccagaagga aucauuccua gcauguucga accagagcgu    6060
gaaaaggugg augccauuga uggcgaauac cgcuugagag agaagcaag gaaaaccuuu    6120 guagacuuaa ugagaagagg agaccuacca gucugguugg ccuacagagu ggcagcugaa    6180
ggcaucaacu acgcagacag aaggugugu uuugauggag ucaagaacaa ccaaauccua    6240
gaagaaaacg uggaaguuga aaucggaca aaagaagggg aaaggaagaa auugaaaccc    6300
agaugguugg augcuaggau cuauucugac ccacuggcgc uaaaagaauu uaaggaauuu    6360
gcagccggaa gaaagucucu gacccugaac cuaaucacag aaaugggaug gcucccaacc    6420
uucaugacuc agaaggcaag agacgcacug gacaacuuag cagugcugca cacggcugag    6480
gcaggaggaa gggcguacaa ccaugcucuc agugaacugc cggagacccu ggagacauug    6540
cuuuuacuga cacuucuggc uacagucacg ggagggaucu uuuauucuu gaugagcgca    6600 aggggcauag ggaagaugac ccugggaaug ugcugcauaa ucacggcuag cauccuccua    6660
ugguacgcac aaauacagcc acacuggaua gcagcuucaa uaauacugga guuuuucuc    6720 auaguuugc uuauuccaga accugaaaaa cagagaacac cccaagacaa ccaacugacc    6780
uacguuguca uagccauccu cacaguggug gccgcaacca uggcaaacga uggguuuc    6840 cuagaaaaaa cgaagaaaga ucucggauug ggaagcauug caaccccagca acccgagagc    6900 aacauccugg acauugaucu acguccugca ucagcaugga cgcuguaugc cguggccaca    6960
acauuuguua caccaaguguu gagacauagc auugaaaauu ccucagugaa ugucccuua    7020 acagcuauag ccaaccaagc cacaguguua augggucucg gaaaggaug gccauuguca    7080 aagauggaca ucggaguucc ccuucucgcc auggaugcu acucacaagu caaccccaua    7140
acucucacag cagcucuuuu cuuauugga gcacauaug ccaucauagg gccaggacuc    7200
caagcaaaag caaccagaga agcucagaaa agagcagcgg cgggcaucau gaaaaaccca    7260
acugucgaug gaauaacagu gauugaccua gauccaauac cuuaugaucc aaaguuugaa    7320
aagcaguugg acaaguaau gcccuaguc cucgcguga cucaaguauu gaugaugagg    7380
acuacauggg cucuguguga ggcuuuaacc uuagcuaccg ggcccaucuc cacauugugg    7440
gaaggaaauc cagggagguu uuggaacacu accauucgg ugucaauggc uaacauuuuu    7500
agagggaguu acuuggccgg agcuggacuu cucuuuucua uuaugaagaa cacaaccaac    7560
```

```
acaagaaggg gaacuggcaa cauaggagag acgcuuggag agaaauggaa aagccgauug    7620
aacgcauugg gaaaaaguga auuccagauc uacaagaaaa guggaaucca ggaaguggau    7680
agaaccuuag caaaagaagg cauuaaaaga ggagaaacgg accaucacgc ugugucgcga    7740
ggcucagcaa aacugagaug guucguugag agaaacaugg ucacaccaga agggaaagua    7800
guggaccucg guuguggcag aggaggcugg ucauacuauu guggaggacu aaagaaugua    7860
agagaaguca aaggccuaac aaaaggagga ccaggacacg aagaacccau ccccaugucaa   7920 acauaugggu ggaaucuagu gcgucuucaa aguggaguug acguuucuu caucccgcca    7980 gaaaagugug acacauuauu gugugacaua ggggagucau caccaaaucc cacaguggaa    8040
gcaggacgaa cacucagagu ccuuaacuua guagaaaauu gguugaacaa caacacucaa    8100
uuuugcauaa agguucucaa cccauauaug cccucaguca uagaaaaaau ggaagcacua    8160
caaaggaaau auggaggagc cuuagugagg aauccacucu cacgaaacuc cacacaugag    8220
auguacuggg uauccaaugc uuccggaacc auagugucau caguçaacau gauuucaagg    8280 auguugauca acagauuuac aaugagauac aagaaagcca cuuacgagcc ggauguugac    8340
cucggaagcg gaaccgcuaa caucgggauu gaaagugaga uaccaaaccu agauauaauu    8400
gggaaaagaa uagaaaaaau aaagcaagag caugaaacau cauggcacua ugaccaagac    8460 caccccauaca aaacgugggc auaccauggu agcuaugaaa caaaacagac uggaucagca    8520
ucauccaugg ucaacggagu ggucaggcug cugacaaaac cuugggacgu uguccccaug    8580
gugacacaga uggcaaugac agacacgacu ccauuuggac aacagcgcgu uuuuaaagag    8640
aaaguggaca cgagaaccca agaaccgaaa gaaggcacga agaaacuaau gaaaauaaca    8700
gcagaguggc uuuggaaaga auugggaaag aaaagacac ccaggaugug caccagagaa    8760
gaauucacaa gaaaggugag aagcaaugca gccuugggg ccauauucac ugaugagaac    8820
aaguggaagu cggcacguga ggcuguugaa gauagaggu uugggagcu gguugacaag    8880 gaaaggaauc uccaucuuga aggaaagugu gaaacaugug uguacaacau gaugggaaaa    8940
agagagaaga agcuagggga auucggcaag gcaaaaggca gcagagccau aaguacaug    9000 uggcuuggag cacgcuucuu agaguuugaa gcccuaggau ucuuaaauga agaucacugg    9060
uucuccagag agaacucccu gaguggagug gaaggagaag ggcugcacaa gcuagguuac    9120
auucuaagag acgugagcaa gaaagaggga ggagcaaugu augccgauga caccgcagga    9180
ugggauacaa aaaucacacu agaagaccua aaaaaugaag agauggugaac aaaccacaug    9240 gaaggagaac acaagaaacu agccgaggcc auuuucaaac uaacguacca aaacaaggug    9300
gugcgcgugc aaagaccaac accaagaggc acaguaaugg acaucauauc gagaagagac    9360
caaagaggua guggacaagu uggcaccuau ggacucaaua cuuucaccaa uauggaagcc    9420
caacuaauca gacagaugga gggagaagga gucuuuaaa gcauucagca ccuaacaauc    9480
acagaagaaa ucgcugugca aacugguua gcaagaguggg gcgcgaaag guuaucaaga    9540 auggccauca guggagauga uugguuguq aaaccuuuag augacaggu cgcaagcgcu    9600 uuaacagcuc uaaaugacau gggaaagauu aggaaagaca uacaacaaug gaaccuuca    9660 agaggaugga augauuggac acaagugccc uucuguucac accauuucca ugaguuaauc    9720
augaaagacg gucgcguacu cguguuccca gugaaaaccc aagaugaacu gauuggcaga    9780
gcccgaaucu cccaaggagc aggguggucu ugcggagaaa cggccuguuu ggggaagucu    9840
uacgcccaaa uguggagcuu gauguacuuc cacagacgcg accucaggcu ggcggcaaau    9900
gcuauuugcu cggcaguacc aucacauugg guuccaacaa gucgaacaac cugguccaua    9960
```

```
caugcuaaac augaauggau gacaacggaa gacaugcuga cagucuggaa caggguguqg    10020 auucaagaaa acccauggau ggaagacaaa acuccagugg aaacauggga ggaaauccca    10080
uacuugggga aaagagaaga ccaauggugc ggcucauuga uuggguuaac aagcagggcc    10140
accugggcaa agaacaucca agcagcaaua aaucaaguua gaucccuuau aggcaaugaa    10200
gaauacacag auuacaugcc auccaugaaa agauucagaa gagaagagga agaagcagga    10260
guucuguggu agaaagcaaa acuaacauga aacaaggcua gaagucaggu cggauuaagc    10320
cauaguacgg aaaaaacuau gcuaccugug agccccgucc aaggacguua aaagaaguca    10380
ggccaucaua aaugccauag cuugaguaaa cuaugcagcc uguagcucca ccugagaagg    10440
uguaaaaaau ccgggaggcc acaaaccaug gaagcuguac gcauggcgua guggacuagc    10500
gguuagggga gaccccuccc uuacaaaucg cagcaacaau ggggccaa ggcgagauga     10560 agcuguaguc ucgcuggaag gacuagaggu uagaggagac cccccgaaa caaaaaacag    10620 cauauugacg cugggaaaga ccagagaucc ugcugucucc ucagcaucau uccaggcaca    10680
gaacgccaga aaauggaaug gugcuguuga aucaacaggu ucu                     10723
```